(12) United States Patent
Lim et al.

(10) Patent No.: US 9,487,504 B2
(45) Date of Patent: Nov. 8, 2016

(54) IMIDAZOLYL ANALOGS AS SYK INHIBITORS

(71) Applicants:Merck Sharp & Dohme Corp., Rahway, NJ (US); Merck Canada Inc., Kirkland, Quebec (CA)

(72) Inventors: Jongwon Lim, Lexington, MA (US); Michael H. Reutershan, Brookline, MA (US); John Michael Ellis, Needham, MA (US); Kaleen Konrad Childers, Medfield, MA (US); Anthony Donofrio, Cambridge, MA (US); Michael D. Altman, Needham, MA (US); Andrew M. Haidle, Cambridge, MA (US); Anna Zabierek, Watertown, MA (US); Matthew Christopher, Brookline, MA (US); Jonathan Grimm, Ashburn, VA (US); Jason Burch, Redwood City, CA (US); Maria Emilia Di Francesco, Houston, TX (US); Alessia Petrocchi, Houston, TX (US); Christian Beaulieu, Laval (CA); Vouy Linh Truong, Pierrefonds (CA); Alan B. Northrup, Reading, MA (US); Marc Blouin, Saint-Lazare (CA)

(73) Assignees: Merck Sharp & Dohme Corp., Rahway, NJ (US); Merck Canada Inc., Kirkland, Quebec (CA)

( * ) Notice: Subject to any disclaimer, the term of this patent is extended or adjusted under 35 U.S.C. 154(b) by 0 days.

(21) Appl. No.: 14/409,147

(22) PCT Filed: Jun. 18, 2013

(86) PCT No.: PCT/US2013/046223
§ 371 (c)(1),
(2) Date: Dec. 18, 2014

(87) PCT Pub. No.: WO2013/192128
PCT Pub. Date: Dec. 27, 2013

(65) Prior Publication Data
US 2015/0175575 A1   Jun. 25, 2015

Related U.S. Application Data

(60) Provisional application No. 61/662,196, filed on Jun. 20, 2012.

(51) Int. Cl.
*C07D 403/12* (2006.01)
*C07D 403/14* (2006.01)
*C07D 401/14* (2006.01)

(52) U.S. Cl.
CPC ......... *C07D 403/12* (2013.01); *C07D 401/14* (2013.01); *C07D 403/14* (2013.01)

(58) Field of Classification Search
CPC . C07D 471/04; C07D 403/12; C07D 401/14

USPC ............ 546/256; 544/122, 331; 514/212.08, 514/275, 235.8
See application file for complete search history.

(56) References Cited

U.S. PATENT DOCUMENTS

| | | | |
|---|---|---|---|
| 5,064,963 A | 11/1991 | Dean | |
| 5,710,129 A | 1/1998 | Lynch et al. | |
| 6,248,790 B1 | 6/2001 | Uckun et al. | |
| 6,432,963 B1 | 8/2002 | Hisamichi et al. | |
| 6,589,950 B1 | 7/2003 | Collingswood et al. | |
| 6,770,643 B2 | 8/2004 | Cox et al. | |
| 6,797,706 B1 | 9/2004 | Hisamichi et al. | |
| 6,897,207 B2 | 5/2005 | Cox et al. | |
| 6,897,208 B2 | 5/2005 | Edwards et al. | |
| 6,911,443 B2 | 6/2005 | Yura et al. | |
| 7,060,827 B2 | 6/2006 | Singh et al. | |
| 7,122,542 B2 | 10/2006 | Singh et al. | |
| 7,227,020 B2 | 6/2007 | Cox et al. | |
| 7,259,154 B2 | 8/2007 | Cox et al. | |
| 7,803,801 B2 | 9/2010 | Kodama et al. | |
| 8,138,339 B2 | 3/2012 | Bauer et al. | |
| 8,551,984 B2 | 10/2013 | Altman et al. | |
| 8,735,417 B2 | 5/2014 | Altman et al. | |
| 8,759,366 B2 | 6/2014 | Childers et al. | |
| 8,796,310 B2 | 8/2014 | Romeo et al. | |
| 8,987,456 B2 | 3/2015 | Altman et al. | |
| 9,006,444 B2 | 4/2015 | Altman et al. | |
| 9,120,785 B2 | 9/2015 | Altman et al. | |
| 2004/0029902 A1 | 2/2004 | Singh et al. | |
| 2004/0054179 A1 | 3/2004 | Yura et al. | |

(Continued)

FOREIGN PATENT DOCUMENTS

JP      2004203748      12/2002
WO      01/60816 A1     8/2001

(Continued)

OTHER PUBLICATIONS

International Search Report and Written Opinion for PCT/US13/46223 mailed on Nov. 1, 2013.

(Continued)

*Primary Examiner* — Rita Desai
(74) *Attorney, Agent, or Firm* — Eric A. Meade; Anna L. Cocuzzo

(57) ABSTRACT

The present invention provides novel imidazole analogs of Formula I which are potent inhibitors of spleen tyrosine kinase, and are useful in the treatment and prevention of diseases mediated by said enzyme, such as asthma, COPD, rheumatoid arthritis, and cancer.

7 Claims, No Drawings

(56) References Cited

U.S. PATENT DOCUMENTS

| | | |
|---|---|---|
| 2006/0135543 A1 | 6/2006 | Singh et al. |
| 2006/0178407 A1 | 8/2006 | Argade et al. |
| 2006/0205731 A1 | 9/2006 | Kodama et al. |
| 2006/0211657 A1 | 9/2006 | Singh et al. |
| 2006/0234483 A1 | 10/2006 | Araki et al. |
| 2006/0247262 A1 | 11/2006 | Baenteli et al. |
| 2007/0004626 A1 | 1/2007 | Masuda et al. |
| 2007/0129362 A1 | 6/2007 | Bhamidipati et al. |
| 2007/0197782 A1 | 8/2007 | Clough et al. |
| 2014/0148474 A1 | 5/2014 | Altman et al. |
| 2014/0243336 A1 | 8/2014 | Altman et al. |
| 2014/0249130 A1 | 9/2014 | Deschenes et al. |
| 2015/0148327 A1 | 5/2015 | Haidle et al. |
| 2015/0166486 A1 | 6/2015 | Haidle et al. |
| 2015/0191461 A1* | 7/2015 | Machacek ............ C07D 403/12 514/210.18 |
| 2015/0239866 A1 | 8/2015 | Machacek et al. |

FOREIGN PATENT DOCUMENTS

| | | |
|---|---|---|
| WO | WO03057659 A1 | 7/2003 |
| WO | WO03078404 A1 | 9/2003 |
| WO | WO2004080463 A1 | 9/2004 |
| WO | WO2005013996 A2 | 2/2005 |
| WO | WO2006093247 A1 | 2/2005 |
| WO | WO2005026158 A1 | 3/2005 |
| WO | WO2005033103 A1 | 4/2005 |
| WO | WO2006004865 A1 | 1/2006 |
| WO | WO2006028833 A1 | 3/2006 |
| WO | WO2006050480 A2 | 5/2006 |
| WO | WO2006068770 A1 | 6/2006 |
| WO | WO2006078846 A1 | 7/2006 |
| WO | WO2006129100 A1 | 12/2006 |
| WO | WO2006133426 A2 | 12/2006 |
| WO | WO2006135915 A2 | 12/2006 |
| WO | WO2007009681 A1 | 1/2007 |
| WO | WO2007009773 A1 | 1/2007 |
| WO | WO2007028445 A1 | 3/2007 |
| WO | WO2007042298 A1 | 4/2007 |
| WO | WO2007042299 A1 | 4/2007 |
| WO | WO2007070872 A1 | 6/2007 |
| WO | WO2007085540 A1 | 8/2007 |
| WO | WO2007107469 A1 | 9/2007 |
| WO | WO2007120980 A2 | 10/2007 |
| WO | WO2009084695 A1 | 12/2007 |
| WO | WO2009031011 A2 | 3/2009 |
| WO | WO2009097287 A1 | 8/2009 |
| WO | WO2009102468 A1 | 8/2009 |
| WO | WO2009131687 A2 | 10/2009 |
| WO | WO2009136995 A2 | 11/2009 |
| WO | WO2009145856 A1 | 12/2009 |
| WO | WO2010027500 A1 | 3/2010 |
| WO | WO2010068257 A1 | 6/2010 |
| WO | WO2010068258 A1 | 6/2010 |
| WO | WO2010129802 A1 | 11/2010 |
| WO | WO2014031438 A2 | 2/2014 |

OTHER PUBLICATIONS

Pubchem, 1-((4((1-Imidazoly)methyl)cyclohexyl)imidazole succinate, 2011.

Rathore, et al., Steric hindrance as a mechanistic probe for olefin reactivity: variability of the hydrogenic canopy over the isomeric adamantylideneadamantane/sesquihomoada mantene pair, Journal of Organic Chemistry, 2002, 5106-5016, 67-15.

* cited by examiner

IMIDAZOLYL ANALOGS AS SYK INHIBITORS

CROSS REFERENCE TO RELATED APPLICATIONS

This application is a U.S. National Phase application under 35 U.S.C. §371 of PCT Application No. PCT/US2013/046223, filed Jun. 18, 2013, which claims priority under 35 U.S.C. §119(e) from U.S. Provisional Application No. 61/662,196, filed Jun. 20, 2012.

BACKGROUND OF THE INVENTION

Spleen Tyrosine Kinase (Syk) is a protein tyrosine kinase which has been described as a key mediator of immunoreceptor signalling in a host of inflammatory cells including mast cells, B-cells, macrophages and neutrophils. These immunoreceptors, including Fc receptors and the B-cell receptor, are important for both allergic diseases and antibody-mediated autoimmune diseases and thus pharmacologically interfering with Syk could conceivably treat these disorders.

Allergic rhinitis and asthma are diseases associated with hypersensitivity reactions and inflammatory events involving a multitude of cell types including mast cells, eosinophils, T cells and dendritic cells. Following exposure to allergen, high affinity immunoglobulin receptors for IgE and IgG become cross-linked and activate downstream processes in mast cells and other cell types leading to the release of pro-inflammatory mediators and airway spasmogens. In the mast cell, for example, IgE receptor cross-linking by allergen leads to release of mediators including histamine from pre-formed granules, as well as the synthesis and release of newly synthesized lipid mediators including prostaglandins and leukotrienes.

Syk kinase is a non-receptor linked tyrosine kinase which is important in transducing the downstream cellular signals associated with cross-linking Fc$_{epsilon}$R1 and or Fc$_{epsilon}$R1 receptors, and is positioned early in the signaling cascade. In mast cells, for example, the early sequence of Fc$_{epsilon}$R1 signalling following allergen cross-linking of receptor-IgE complexes involves first Lyn (a Src family tyrosine kinase) and then Syk. Inhibitors of Syk activity would therefore be expected to inhibit all downstream signalling cascades thereby alleviating the immediate allergic response and adverse events initiated by the release of pro-inflammatory mediators and spasmogens (Wong et al. 2004, Expert Opin. Investig. Drugs (2004) 13 (7) 743-762).

Recently, it has been shown that the Syk kinase inhibitor R112 (Rigel), dosed intranasally in a phase I/II study for the treatment of allergic rhinitis, gave a statistically significant decrease in PGD$_2$, a key immune mediator that is highly correlated with improvements in allergic rhinorrhea, as well as being safe across a range of indicators, thus providing the first evidence for the clinical safety and efficacy of a topical Syk kinase inhibitor. (Meltzer, Eli O.; Berkowitz, Robert B.; Grossbard, Elliott B, Journal of Allergy and Clinical Immunology (2005), 115(4), 791-796). In a more recent phase II clinical trial for allergic rhinitis (Clinical Trials.gov Identifier NCT0015089), R112 was shown as having a lack of efficacy versus placebo.

Rheumatoid Arthritis (RA) is an auto-immune disease affecting approximately 1% of the population. It is characterised by inflammation of articular joints leading to debilitating destruction of bone and cartilage. Recent clinical studies with Rituximab, which causes a reversible B cell depletion, (J. C. W. Edwards et al. 2004, New Eng. J. Med. 350: 2572-2581) have shown that targeting B cell function is an appropriate therapeutic strategy in auto-immune diseases such as RA. Clinical benefit correlates with a reduction in auto-reactive antibodies (or Rheumatoid Factor) and these studies suggest that B cell function and indeed auto-antibody production are central to the ongoing pathology in the disease.

Studies using cells from mice deficient in the Spleen Tyrosine Kinase (Syk) have demonstrated a non-redundant role of this kinase in B cell function. The deficiency in Syk is characterised by a block in B cell development (M. Turner et al. 1995 Nature 379: 298-302 and Cheng et al. 1995, Nature 378: 303-306). These studies, along with studies on mature B cells deficient in Syk (Kurasaki et al. 2000, Immunol. Rev. 176:19-29), demonstrate that Syk is required for the differentiation and activation of B cells. Hence, inhibition of Syk in RA patients is likely to block B cell function and thereby reduce Rheumatoid Factor production. In addition to the role of Syk in B cell function, and of further relevance to the treatment of RA, is the requirement for Syk activity in Fc receptor (FcR) signalling. FcR activation by immune complexes in RA has been suggested to contribute to the release of multiple pro-inflammatory mediators.

U.S. Pat. No. 7,803,801 discloses Syk inhibitors having the formula:

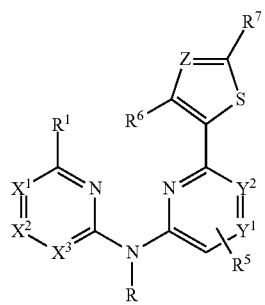

wherein the variables are as defined therein.

The present invention relates to novel compounds, which are inhibitors of Syk kinase activity. These compounds therefore have potential therapeutic benefit in the treatment of disorders associated with inappropriate Syk activity, in particular in the treatment and prevention of disease states mediated by Syk. Such disease states may include inflammatory, allergic and autoimmune diseases, for example, asthma, chronic obstructive pulmonary disease (COPD), adult respiratory distress syndrome (ARDS), ulcerative colitis, Crohns disease, bronchitis, dermatitis, allergic rhinitis, psoriasis, scleroderma, urticaria, rheumatoid arthritis, idiopathic thrombocytopenic purpura (ITP), multiple sclerosis, cancer, HIV and lupus.

SUMMARY OF THE INVENTION

The present invention provides novel compounds that are potent inhibitors of Syk as well as pharmaceutical compositions containing them. As Syk inhibitors compounds of the present invention are useful in the treatment and prevention of diseases and disorders mediated by the Syk protein; such diseases and disorders include, but are not limited to, asthma, COPD, rheumatoid arthritis, cancer and idiopathic thrombocytopenic purpura.

DETAILED DESCRIPTION OF THE INVENTION

In embodiment no. 1, the present invention provides compounds of Formula I:

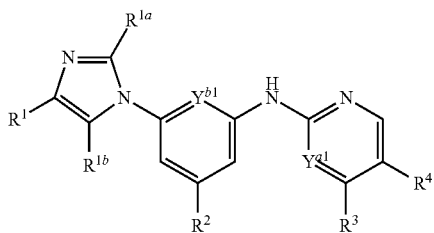

I or a pharmaceutically acceptable salt thereof, wherein:
$Y^{a1}$ is CH or N;
$Y^{b1}$ is CH or N, such that $Y^{b1}$ and $Y^{a1}$ cannot both simultaneously be C or N;
$R^{1a}$ and $R^{1b}$ are independently H or $C_1$-$C_3$-alkyl;
$R^1$ is:
  H;
  halogen;
  $C_1$-$C_6$-alkyl or $C_2$-$C_6$-alkenyl, optionally with one or more substituent selected from the group consisting of: CN, OH, oxo, $NH_2$, $CF_3$, $C_1$-$C_3$-alkyl, or $C_1$-$C_3$-alkoxyl;
  $(CR^aR^b)_n CO_2R^c$;
  $(CR^aR^b)_n CONR^dR^e$;
  $(CHR^a)_n NHCONR^dR^e$;
  $(CHR^a)_n CONHSO_2R^d$;
  $(CHR^a)_n SO_2R^d$;
  $(CHR^a)_n SO_2NR^dR^e$;
  $(CR^aR^b)_n$-heterocyclyl; wherein heterocyclyl is as defined below;
  $(CHR^a)_p$—C(O)-heterocyclyl; wherein heterocyclyl is as defined below;
  $(CR^aR^b)_n$-carbocyclyl; wherein carbocyclyl is as defined below;
  $CR^a$(carbocyclyl)$_2$; wherein carbocyclyl is as defined below;
  $(CR^aR^b)_n$-aryl; wherein aryl is as defined below;
  $(CR^aR^b)_n$—O-carbocyclyl; wherein carbocyclyl is as defined below;
  $(CR^aR^b)_n$—O-aryl; wherein aryl is as defined below;
heterocyclyl is a 4-, 5-, 6-, or 7-membered monocyclic ring or 8-, 9-, 10-membered bicyclic ring, or 13- or 14-membered tricyclic ring; the monocyclic, bicyclic or tricyclic ring can be saturated, unsaturated or aromatic, containing 1, 2, 3 or 4 heteroatoms selected from O, N. or S, the heterocyclyl may optionally be substituted with one to four substituents selected from oxo, halo, hydroxyl, $C_1$-$C_3$-alkyl, $C_2$-$C_6$-alkenyl, $C_1$-$C_3$-alkoxyl, $(CR^aR^b)_n CO_2R^c$, $(CR^aR^b)_n CONR^dR^e$, $(CHR^a)_n NHCONR^dR^e$, and $(CHR^a)_p$—C(O)-heterocyclyl;
carbocyclyl is a 4-, 5-, 6-, 7- or 8-membered monocyclic ring or 8-, 9-, 10-membered bicyclic ring, or 13- or 14-membered tricyclic ring, in which all ring atoms are carbon, at least one ring is saturated or partially unsaturated and that ring being isolated or fused to one or two such rings or to a benzene ring; the carbocyclyl may optionally be substituted with one to four substituents selected from hydroxyl, $C_1$-$C_3$-alkyl, $C_1$-$C_3$-alkoxyl, $(CR^aR^b)_n CO_2R^c$, $(CR^aR^b)_n CONR^dR^e$, and a spiro-linked —$OCH_2CH_2O$—;
aryl is a 6-membered monocyclic or 10-membered bicyclic aromatic carbon ring, the aryl may optionally be substituted with one to four substituents selected from hydroxyl, $C_1$-$C_3$-alkyl, $C_1$-$C_3$-alkoxyl, $(CR^aR^b)_n CO_2R^c$, and $(CR^aR^b)_n CONR^dR^e$;
$R^a$ and $R^b$ are independently: H, OH, or $C_1$-$C_3$-alkyl optionally substituted with 1-3 hydroxyl;
$R^c$ is: H; $C_{1-6}$alkyl, -M-$R^{CH}$, —$(CH_2)_{1-2}$—$R^f$, —$(CH_2)_2$—O—$(CH_2)_2$—$R^f$, —$(CH_2)_2$—$R^g$, —$CHR^hOCO_2R^i$, or —$(CHR^h)_{1-2}OC(O)R^i$;
$R^d$ and $R^e$ are independently: H, $C_1$-$C_3$-alkoxyl or $C_1$-$C_6$-alkyl, optionally substituted with 1-4 substituents selected from: CN, OH, oxo, $NH_2$; halogen, $CO_2R^c$, $CONH_2$, $C_1$-$C_3$-alkoxyl, $CO_2R^c$, aryl, carbocyclyl, and heterocyclyl, as defined above;
$R^d$ and $R^e$ taken together with the nitrogen to which they are attached form a heterocyclic 3- to 7-membered monocyclic ring, a 10-, 11-, or 12-membered bicyclic ring or a 13-membered tricyclic ring, containing 0-4 additional heteroatoms selected from O, N, or S, one or more of the rings may be saturated, unsaturated or aromatic; the heterocyclic ring is optionally substituted with 1-4 substituents selected from CN, OH, oxo, $NH_2$; halogen, $COCH_3$, $CO_2R^c$, $CONH_2$, $C_1$-$C_3$-alkyl, $C_1$-$C_3$-haloalkyl, $C_1$-$C_3$-alkoxyl optionally substituted with OH; aryl optionally substituted with $C_1$-$C_3$-alkoxyl; $CH_2$aryl; Oaryl optionally substituted with halogen; and heterocyclyl, wherein aryl and heterocyclyl are as defined above;
$R^f$ is $CO_2R^{f1}$, $C(O)N(R^{f2})_2$, —$OC(O)R^{f1}$, or $C_{1-2}$alkoxyl;
$R^{f1}$ is $C_{1-4}$alkyl;
$R^{f2}$ is H or $C_{1-4}$alkyl;
$R^g$ is OH, $C_{1-4}$alkoxyl, $NH_2$, $NH(C_{1-4}$alkyl) or $N(C_{1-4}$alkyl)$_2$;
$R^h$ is H or $C_{1-4}$alkyl;
$R^i$ is $C_{1-6}$alkyl, $C_{3-6}$cycloalkyl, or phenyl;
M is a bond or —$(CH_2)_{1-2}$—;
$R^{CH}$ is (a) aryl, aryl is phenyl or naphthalyl, optionally substituted with 1-3 groups independently selected from halo, $C_{1-4}$alkyl, or $C_{1-4}$alkoxy; (b) carbocyclyl, carbocyclyl is a 5-, 6- or 7-membered monocyclic carbon ring, that is saturated or partially unsaturated and the carbocyclyl is optionally substituted with 1-3 substituents independently selected from halo, $C_{1-4}$alkyl, or $C_{1-4}$alkoxy; or (c) a 5- to 6-membered monocyclic heterocyclyl containing 1 or 2 heteroatoms independently selected from the group consisting of N and O, and the heterocyclyl is optionally substituted with 1 or 2 substituents independently selected from the group consisting of: oxo and $C_{1-3}$alkyl;
n is 0, 1, 2, 3 or 4;
p is 0 or 1;
$R^2$ is H, halogen, $C_1$-$C_3$-alkyl, $C_1$-$C_3$-haloalkyl, $C_3$-$C_7$-cycloalkyl, heterocyclyl, $NR^dR^e$, $CONR^dR^e$, or $NHCONR^dR^e$;
$R^3$ is H; halogen; $C_1$-$C_4$-alkyl, optionally substituted with $C_1$-$C_3$-alkoxyl; $C_1$-$C_3$-alkoxyl; $C_1$-$C_3$-haloalkyl; $C_1$-$C_3$-alkoxyl, optionally substituted with hydroxyl; or $C_3$-$C_6$-cycloalkyl; and
$R^4$ is H, halogen, or $C_1$-$C_3$-alkyl.

In embodiment no. 2, the compound of the Formula I has the Formula Ia

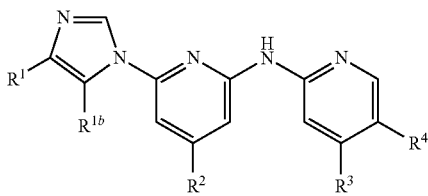

and all other substituents are as defined in embodiment no. 1.

In embodiment no. 3, the compound of the Formula I has the Formula Ib

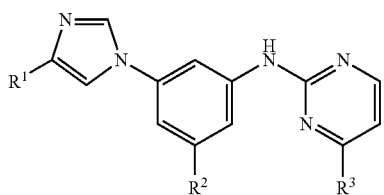

and all other substituents are as defined in embodiment no. 1.

In embodiment no. 4, the compound has Formula I, wherein:

$R^{1a}$ and $R^{1b}$ are H;

$R^1$ is:
H;
halogen;
$C_1$-$C_6$-alkyl or $C_2$-$C_6$-alkenyl, optionally with one or more substituent selected from the group consisting of: CN, OH, oxo, $NH_2$, $CF_3$, $C_1$-$C_3$-alkyl, and $C_1$-$C_3$-alkoxyl;
$(CR^aR^b)_n CO_2R^c$;
$(CR^aR^b)_n CONR^dR^e$;
$(CHR^a)_n NHCONR^dR^e$;
$(CHR^a)_n CONHSO_2R^d$;
$(CHR^a)_n SO_2R^d$;
$(CHR^a)_n SO_2NR^dR^e$;
$(CR^aR^b)_n$-heterocyclyl;
$(CHR^a)_p$—C(O)-heterocyclyl;
$(CR^aR^b)_n$-carbocyclyl;
$CR^a(carbocyclyl)_2$;
$(CR^aR^b)_n$-aryl;
$(CR^aR^b)_n$—O-carbocyclyl;
$(CR^aR^b)_n$—O-aryl;

$R^a$ and $R^b$ are independently: H, OH, or $C_1$-$C_3$-alkyl optionally substituted with 1-3 hydroxyl;

$R^c$ is: H; or $C_{1-4}$alkyl;

$R^d$ and $R^e$ are independently: H, $C_1$-$C_3$-alkoxyl or $C_1$-$C_6$-alkyl, optionally substituted with 1-4 substituents selected from: CN, OH, oxo, $NH_2$, halogen, $CO_2R^c$, $CONH_2$, $C_1$-$C_3$-alkoxyl, $CO_2R^c$, aryl, carbocyclyl, or heterocyclyl, as defined above;

$R^d$ and $R^e$ taken together with the nitrogen to which they are attached form a heterocyclic 5- to 6-membered monocyclic ring, containing 0-2 additional heteroatoms selected from O, N, or S, the ring maybe saturated, unsaturated or aromatic; and optionally substituted with 1-2 substituents selected from CN; OH; oxo; $NH_2$; halogen; $COCH_3$; $CO_2R^c$; $CONH_2$; $C_1$-$C_3$-alkyl; $C_1$-$C_3$-haloalkyl; $C_1$-$C_3$-alkoxyl optionally substituted with OH; aryl optionally substituted with $C_1$-$C_3$-alkoxyl; $CH_2$aryl; Oaryl optionally substituted with halogen; and heterocyclyl, wherein aryl and heterocyclyl are as defined above;

n is 0, 1, 2, 3 or 4;
p is 0 or 1;
$R^2$ is H, or $CH_3$;
$R^3$ is H, $CF_3$, $CH_3$, or $CF_2H$;
$R^4$ is H, Cl or F;
and all other variables are as defined in embodiment no. 1.

In embodiment no. 5, the compound has Formula I, wherein:

$R^{1a}$ and $R^{1b}$ are H;

$R^1$ is —C(H)($R^b$)-cyclohexyl, wherein said cyclohexyl is optionally substituted with 1 to 3 groups independently selected from the group consisting of hydroxyl, methyl, $CO_2H$, $CH_2CO_2H$, and $C(O)NH_2$;

$R^b$ is H or hydroxyl;
$R^2$ is H or methyl;
$R^3$ is methyl or $CF_3$; and
$R^4$ is H.

In embodiment no. 6, the compound of Formula I has the Formula Ia as set forth in embodiment no. 2, and $R^1$, $R^{1b}$, $R^2$, $R^3$, and $R^4$ are as set forth in embodiment no. 5.

In embodiment no. 7, the compound of Formula I has the Formula Ib as set forth in embodiment no. 3, and $R^1$, $R^2$, and $R^3$, and $R^4$ are as set forth in embodiment no. 5.

In embodiment no. 8, the compound of Formula I is as described in any one of embodiments no. 1-7, wherein $R^3$ is $CF_3$ and $R^2$ is methyl.

Representative compounds of the present invention are as follows, where each named compound is intended to encompass its individual isomers, mixtures thereof (including racemates and diastereomeric mixtures), as well as pharmaceutically acceptable salts thereof:

In another embodiment, the compounds (including pharmaceutically acceptable salts thereof) are selected from the following compounds:

Cis-4-hydroxy-N-methyl-4-[1-(3-methyl-5-{[4-(trifluoromethyl)pyrimidin-2-yl]amino}phenyl)-1H-imidazol-4-yl]cyclohexanecarboxamide;

Trans-4-[1-(3-methyl-5-{[4-(trifluoromethyl)pyrimidin-2-yl]amino}phenyl)-1H-imidazol-4-yl]cyclohexanecarboxylic acid;

Cis-4-[1-(3-methyl-5-{[4-(trifluoromethyl)pyrimidin-2-yl]amino}phenyl)-1H-imidazol-4-yl]cyclohexanecarboxylic acid;

4-[1-(3-Methyl-5-{[4-(trifluoromethyl)pyrimidin-2-yl]amino}phenyl)-1H-imidazol-4-yl]cyclohex-3-ene-1-carboxylic acid;

6,6-Dimethyl-4-[1-(3-methyl-5-{[4-(trifluoromethyl)pyrimidin-2-yl]amino}phenyl)-1H-imidazol-4-yl]cyclohex-3-ene-1-carboxylic acid;

Rac-(1R,3S,4S)-3,4-dihydroxy-1-methyl-4-[1-(3-methyl-5-{[4-(trifluoromethyl)pyrimidin-2-yl]amino}phenyl)-1H-imidazol-4-yl]cyclohexanecarboxylic acid;

Rac-(1R,3R,4R)-3,4-dihydroxy-1-methyl-4-[1-(3-methyl-5-{[4-(trifluoromethyl)pyrimidin-2-yl]amino}phenyl)-1H-imidazol-4-yl]cyclohexanecarboxylic acid;

2-{Cis-4-hydroxy-4-[1-(3-methyl-5-{[4-(trifluoromethyl)pyrimidin-2-yl]amino}phenyl)-1H-imidazol-4-yl]cyclohexyl}acetamide;

Trans-4-{1-hydroxy-1-[1-(3-methyl-5-{[4-(trifluoromethyl)pyrimidin-2-yl]amino}phenyl)-1H-imidazol-4-yl]ethyl}cyclohexanecarboxamide;

(2S)-3-(1-{3-[(4-Cyclopropylpyrimidin-2-yl)amino]-5-methylphenyl}-1H-imidazol-4-yl)-2-hydroxypropanoic acid;

Trans-4-[1-hydroxy-1-(1-{3-methyl-5-[(4-methyl-pyrimidin-2-yl)amino]-phenyl}-1H-imidazol-4-yl)ethyl]cyclohexane-carboxylic acid;

Trans-4-{1-hydroxy-1-[1-(3-methyl-5-{[4-(trifluoromethyl)pyrimidin-2-yl]amino}phenyl)-1H-imidazol-4-yl]ethyl}-cyclohexanecarboxylic acid;

Butyl Trans-4-[1-hydroxy-1-(1-{3-methyl-5-[(4-methylpyrimidin-2-yl)amino]phenyl}-1H-imidazol-4-yl)ethyl]-cyclohexanecarboxylate;

Butyl Trans-4-{1-hydroxy-1-[1-(3-methyl-5-{[4-(trifluoromethyl)pyrimidin-2-yl]amino}phenyl)-1H-imidazol-4-yl]ethyl}cyclohexanecarboxylate;

{Trans-4-hydroxy-4-[1-(4-methyl-6-{[4-(trifluoromethyl)pyridin-2-yl]amino}pyridin-2-yl)-1H-imidazol-4-yl]cyclohexyl}acetic acid;

{Cis-4-hydroxy-4-[1-(4-methyl-6-{[4-(trifluoromethyl)pyridin-2-yl]amino}pyridin-2-yl)-1H-imidazol-4-yl]cyclohexyl}acetic acid;

{Trans-4-hydroxy-4-[1-(3-methyl-5-{[4-(trifluoromethyl)pyrimidin-2-yl]amino}phenyl)-1H-imidazol-4-yl]cyclohexyl}acetic acid;

{Cis-4-hydroxy-4-[1-(3-methyl-5-{[4-(trifluoromethyl)pyrimidin-2-yl]amino}phenyl)-1H-imidazol-4-yl]cyclohexyl}acetic acid;

Methyl {Trans-4-hydroxy-4-[1-(3-methyl-5-{[4-(trifluoromethyl)pyrimidin-2-yl]amino}phenyl)-1H-imidazol-4-yl]cyclohexyl}acetate;

Methyl {Cis-4-hydroxy-4-[1-(3-methyl-5-{[4-(trifluoromethyl)pyrimidin-2-yl]amino}phenyl)-1H-imidazol-4-yl]cyclohexyl}acetate;

Ethyl 1-methyl-4-[1-(3-methyl-5-{[4-(trifluoromethyl)pyrimidin-2-yl]amino}phenyl)-1H-imidazol-4-yl]cyclohex-3-ene-1-carboxylate;

Trans-4-hydroxy-1-methyl-4-[1-(3-methyl-5-{[4-(trifluoromethyl)pyrimidin-2-yl]amino}phenyl)-1H-imidazol-4-yl]cyclohexanecarboxylic acid;

1-Methyl-4-[1-(3-methyl-5-{[4-(trifluoromethyl)pyrimidin-2-yl]amino}phenyl)-1H-imidazol-4-yl]cyclohex-3-ene-1-carboxylic acid;

Ethyl Trans-4-hydroxy-1-methyl-4-[1-(3-methyl-5-{[4-(trifluoromethyl)pyrimidin-2-yl]amino}phenyl)-1H-imidazol-4-yl]cyclohexanecarboxylate;

Ethyl 2-{Cis-4-hydroxy-4-[1-(4-methyl-6-{[4-(trifluoromethyl)pyridin-2-yl]amino}pyridin-2-yl)-1H-imidazol-4-yl]cyclohexyl}-2-methylpropanoate;

Ethyl 2-{Trans-4-hydroxy-4-[1-(4-methyl-6-{[4-(trifluoromethyl)pyridin-2-yl]amino}pyridin-2-yl)-1H-imidazol-4-yl]cyclohexyl}-2-methylpropanoate;

4-Hydroxy-2,2-dimethyl-4-[1-(3-methyl-5-{[4-(trifluoromethyl)pyrimidin-2-yl]amino}phenyl)-1H-imidazol-4-yl]cyclohexanecarboxylic acid;

Trans-4-hydroxy-4-[1-(4-methyl-6-{[4-(trifluoromethyl)pyridin-2-yl]amino}pyridin-2-yl)-1H-imidazol-4-yl]cyclohexanecarboxylic acid;

Cis-4-hydroxy-4-[1-(4-methyl-6-{[4-(trifluoromethyl)pyridin-2-yl]amino}pyridin-2-yl)-1H-imidazol-4-yl]cyclohexanecarboxylic acid;

Ethyl Trans-4-hydroxy-4-[1-(4-methyl-6-{[4-(trifluoromethyl)pyridin-2-yl]amino}pyridin-2-yl)-1H-imidazol-4-yl]cyclohexanecarboxylate;

Ethyl Cis-4-hydroxy-4-[1-(4-methyl-6-{[4-(trifluoromethyl)pyridin-2-yl]amino}pyridin-2-yl)-1H-imidazol-4-yl]cyclohexanecarboxylate;

Cis-1-[1-(3-methyl-5-{[4-(trifluoromethyl)pyrimidin-2-yl]amino}phenyl)-1H-imidazol-4-yl]-4-(morpholin-4-ylcarbonyl)cyclohexanol;

Cis-1-[1-(3-methyl-5-{[4-(trifluoromethyl)pyrimidin-2-yl]amino}phenyl)-1H-imidazol-4-yl]-4-(pyrrolidin-1-ylcarbonyl)cyclohexanol;

Cis-4-hydroxy-N,N-dimethyl-4-[1-(3-methyl-5-{[4-(trifluoromethyl)pyrimidin-2-yl]amino}phenyl)-1H-imidazol-4-yl]cyclohexanecarboxamide;

Trans-4-hydroxy-4-[1-(3-methyl-5-{[4-(trifluoromethyl)pyrimidin-2-yl]amino}phenyl)-1H-imidazol-4-yl]cyclohexanecarboxamide;

Cis-4-hydroxy-4-[1-(3-methyl-5-{[4-(trifluoromethyl)pyrimidin-2-yl]amino}phenyl)-1H-imidazol-4-yl]cyclohexanecarboxamide;

Trans-4-hydroxy-4-[1-(3-methyl-5-{[4-(trifluoromethyl)pyrimidin-2-yl]amino}phenyl)-1H-imidazol-4-yl]cyclohexanecarboxylic acid;

Ethyl Trans-4-hydroxy-4-[1-(3-methyl-5-{[4-(trifluoromethyl)pyrimidin-2-yl]amino}phenyl)-1H-imidazol-4-yl]cyclohexanecarboxylate;

Cis-1-[1-(3-methyl-5-{[4-(trifluoromethyl)pyrimidin-2-yl]amino}phenyl)-1H-imidazol-4-yl]cyclohexane-1,4-diol;

Cis-1-(1-{3-methyl-5-[(4-methylpyrimidin-2-yl)amino]phenyl}-1H-imidazol-4-yl)cyclohexane-1,4-diol;

Cis-1-(1-{3-[(4-methoxypyrimidin-2-yl)amino]-5-methylphenyl}-1H-imidazol-4-yl)cyclohexane-1,4-diol;

Cis-1-(1-{3-[(4-cyclopropylpyrimidin-2-yl)amino]-5-methylphenyl}-1H-imidazol-4-yl)cyclohexane-1,4-diol;

Cis-4-hydroxy-4-(1-{3-[(4-methoxypyrimidin-2-yl)amino]-5-methylphenyl}-1H-imidazol-4-yl)cyclohexyl benzoate;

Cis-4-(1-{3-[(4-cyclopropylpyrimidin-2-yl)amino]-5-methylphenyl}-1H-imidazol-4-yl)-4-hydroxycyclohexyl benzoate;

Cis-1-(1-{6-[(5-fluoro-4-methylpyridin-2-yl)amino]-4-methylpyridin-2-yl}-1H-imidazol-4-yl)cyclohexane-1,4-diol;

Cis-1-(1-{6-[(5-chloro-4-methylpyridin-2-yl)amino]-4-methylpyridin-2-yl}-1H-imidazol-4-yl)cyclohexane-1,4-diol;

Cis-1-(1-{6-[(4-cyclopropylpyridin-2-yl)amino]-4-methylpyridin-2-yl}-1H-imidazol-4-yl)cyclohexane-1,4-diol;

Cis-1-(1-{4-methyl-6-[(4-methylpyridin-2-yl)amino]pyridin-2-yl}-1H-imidazol-4-yl)cyclohexane-1,4-diol;

Cis-1-(1-{6-[(4-tert-butylpyridin-2-yl)amino]-4-methylpyridin-2-yl}-1H-imidazol-4-yl)cyclohexane-1,4-diol;

Cis-4-(1-{6-[(5-fluoro-4-methylpyridin-2-yl)amino]-4-methylpyridin-2-yl}-1H-imidazol-4-yl)-4-hydroxycyclohexyl benzoate;

Cis-4-(1-{6-[(5-chloro-4-methylpyridin-2-yl)amino]-4-methylpyridin-2-yl}-1H-imidazol-4-yl)-4-hydroxycyclohexyl benzoate;

Cis-4-(1-{6-[(4-cyclopropylpyridin-2-yl)amino]-4-methylpyridin-2-yl}-1H-imidazol-4-yl)-4-hydroxycyclohexyl benzoate;

Cis-4-hydroxy-4-(1-{4-methyl-6-[(4-methylpyridin-2-yl)amino]pyridin-2-yl}-1H-imidazol-4-yl)cyclohexyl benzoate;

Cis-4-(1-{6-[(4-tert-butylpyridin-2-yl)amino]-4-methylpyridin-2-yl}-1H-imidazol-4-yl)-4-hydroxycyclohexyl benzoate;

4-Hydroxy-4-[1-(3-methyl-5-{[4-(trifluoromethyl)pyrimidin-2-yl]amino}phenyl)-1H-imidazol-4-yl]cyclohexanone;

(1S,3S,4S)-3-Methyl-1-[1-(3-methyl-5-{[4-(trifluoromethyl)pyrimidin-2-yl]amino}phenyl)-1H-imidazol-4-yl]cyclohexane-1,4-diol;

(1R,3S,4S)-3-Methyl-1-[1-(3-methyl-5-{[4-(trifluoromethyl)pyrimidin-2-yl]amino}phenyl)-1H-imidazol-4-yl]cyclohexane-1,4-diol;

(1S,3S,4R)-3-Methyl-1-[1-(3-methyl-5-{[4-(trifluoromethyl)pyrimidin-2-yl]amino}phenyl)-1H-imidazol-4-yl]cyclohexane-1,4-diol;

Cis-1-(1-{3-[(5-fluoro-4-methylpyrimidin-2-yl)amino]-5-methylphenyl}-1H-imidazol-4-yl)cyclohexane-1,4-diol;

Cis-4-(1-{3-[(5-fluoro-4-methylpyrimidin-2-yl)amino]-5-methylphenyl}-1H-imidazol-4-yl)-4-hydroxycyclohexyl benzoate;

Cis-1-(1-{3-[(4-cyclopropyl-5-fluoropyrimidin-2-yl)amino]-5-methylphenyl}-1H-imidazol-4-yl)cyclohexane-1,4-diol;

Cis-4-(1-{3-[(4-cyclopropyl-5-fluoropyrimidin-2-yl)amino]-5-methylphenyl}-1H-imidazol-4-yl)-4-hydroxycyclohexyl benzoate;

Trans-1-[1-(4-methyl-6-{[4-(trifluoromethyl)pyridin-2-yl]amino}pyridin-2-yl)-1H-imidazol-4-yl]cyclohexane-1,4-diol;

Cis-1-[1-(4-methyl-6-{[4-(trifluoromethyl)pyridin-2-yl]amino}pyridin-2-yl)-1H-imidazol-4-yl]cyclohexane-1,4-diol;

Trans-4-hydroxy-4-[1-(4-methyl-6-{[4-(trifluoromethyl)pyridin-2-yl]amino}pyridin-2-yl)-1H-imidazol-4-yl]cyclohexyl benzoate;

Cis-4-hydroxy-4-[1-(4-methyl-6-{[4-(trifluoromethyl)pyridin-2-yl]amino}pyridin-2-yl)-1H-imidazol-4-yl]cyclohexyl benzoate;

Trans-1-[1-(3-methyl-5-{[4-(trifluoromethyl)pyrimidin-2-yl]amino}phenyl)-1H-imidazol-4-yl]cyclohexane-1,4-diol;

Trans-4-hydroxy-4-[1-(3-methyl-5-{[4-(trifluoromethyl)pyrimidin-2-yl]amino}phenyl)-1H-imidazol-4-yl]cyclohexyl benzoate;

2-Methyl-1-(3-methyl-5-{[4-(trifluoromethyl)pyrimidin-2-yl]amino}phenyl)-1H-imidazole-4-carboxylic acid;

2-[2-Methyl-1-(3-methyl-5-{[4-(trifluoromethyl)pyrimidin-2-yl]amino}phenyl)-1H-imidazol-4-yl]propan-2-ol;

Methyl 1-{6[(4-chloropyridin-2-yl)amino]pyridin-2-yl}-1H-imidazole-4-carboxylate;

Pyrrolidin-1-yl[1-(3-{[4-(trifluoromethyl)pyrimidin-2-yl]amino}phenyl)-1H-imidazol-4-yl]methanone;

4-[1-(3-Methyl-5-{[4-(trifluoromethyl)pyrimidin-2-yl]amino}phenyl)-1H-imidazol-4-yl]benzoic acid;

1-{3-Methyl-5-[(4-methylpyrimidin-2-yl)amino]phenyl}-1H-benzimidazole-5-carboxylic acid;

Methyl 1-{3-methyl-5-[(4-methylpyrimidin-2-yl)amino]phenyl}-1H-benzimidazole-5-carboxylate;

3-[1-(4-Methyl-6-{[4-(trifluoromethyl)pyridin-2-yl]amino}pyridin-2-yl)-1H-imidazol-4-yl]propanoic acid;

3-(1-{3-[(4-Cyclopropylpyrimidin-2-yl)amino]-5-methylphenyl}-1H-imidazol-4-yl)propanoic acid;

3-[1-(3-Methyl-5-{[4-(trifluoromethyl)pyrimidin-2-yl]amino}phenyl)-1H-imidazol-4-yl]propanoic acid;

[1-(3-Methyl-5-{[4-(trifluoromethyl)pyrimidin-2-yl]amino}phenyl)-1H-imidazol-4-yl]acetonitrile;

1-(3-Methyl-5-{[4-(trifluoromethyl)pyrimidin-2-yl]amino}phenyl)-1H-imidazole-4-carboxylic acid;

(1-{4-Amino-6-[(4-chloropyridin-2-yl)amino]pyridin-2-yl}-1H-imidazol-4-yl)(dicyclopropyl)methanol;

(1-{6-[(4-Chloropyridin-2-yl)amino]-4-methylpyridin-2-yl}-1H-imidazol-4-yl)(dicyclopropyl)methanol;

(1-{6-[(4-Chloropyridin-2-yl)amino]pyridin-2-yl}-1H-imidazol-4-yl)(dicyclopropyl)methanol;

Dicyclopropyl[1-(3-{[4-(trifluoromethyl)pyrimidin-2-yl]amino}phenyl)-1H-imidazol-4-yl]methanol;

Dicyclopropyl[1-(6-{[4-(trifluoromethyl)pyridin-2-yl]amino}pyridin-2-yl)-1H-imidazol-4-yl]methanol;

[1-(4-Amino-6-{[4-(trifluoromethyl)pyridin-2-yl]amino}pyridin-2-yl)-1H-imidazol-4-yl](dicyclopropyl)methanol;

Methyl 1-(4-amino-6-{[4-(trifluoromethyl)pyridin-2-yl]amino}pyridin-2-yl)-1H-imidazole-4-carboxylate;

Dicyclopropyl(1-{4-methyl-6-[(4-methylpyridin-2-yl)amino]pyridin-2-yl}-1H-imidazol-4-yl)methanol;

2-(1-{4-Methyl-6-[(4-methylpyridin-2-yl)amino]pyridin-2-yl}-1H-imidazol-4-yl)propan-2-ol;

N-{3-Methyl-5-[4-(pyrrolidin-1-ylcarbonyl)-1H-imidazol-1-yl]phenyl}-4-(trifluoromethyl)pyrimidin-2-amine;

N-(1-Methylethyl)-1-(3-methyl-5-{[4-(trifluoromethyl)pyrimidin-2-yl]amino}phenyl)-1H-imidazole-4-carboxamide;

2-[1-(4-Chloro-6-{[4-(trifluoromethyl)pyridin-2-yl]amino}pyridin-2-yl)-1H-imidazol-4-yl]propan-2-ol;

2-{1-[4-(Trifluoromethyl)-6-{[4-(trifluoromethyl)pyridin-2-yl]amino}pyridin-2-yl]-1H-imidazol-4-yl}propan-2-ol;

2-[1-(4-Methyl-6-{[4-(trifluoromethyl)pyridin-2-yl]amino}pyridin-2-yl)-1H-imidazol-4-yl]propan-2-ol;

Methyl 1-(4-methyl-6-{[4-(trifluoromethyl)pyridin-2-yl]amino}pyridin-2-yl)-1H-imidazole-4-carboxylate;

2-[1-(6-{(Trifluoromethyl)pyridin-2-yl]amino}pyridin-2-yl)-1H-imidazol-4-yl]propan-2-ol;

2-(1-{6-[(4-Chloropyridin-2-yl)amino]-4-methylpyridin-2-yl}-1H-imidazol-4-yl)propan-2-ol;

Methyl 1-(6-{[4-(trifluoromethyl)pyridin-2-yl]amino}pyridin-2-yl)-1H-imidazole-4-carboxylate;

Methyl 1-{6[(4-chloropyridin-2-yl)amino]-4-methylpyridin-2-yl}-1H-imidazole-4-carboxylate;

Methyl 1-(3-methyl-5-{[4-(trifluoromethyl)pyrimidin-2-yl]amino}phenyl)-1H-imidazole-4-carboxylate;

2-[1-(3-Methyl-5-{[4-(trifluoromethyl)pyrimidin-2-yl]amino}pyridin)-1H-imidazol-4-yl]propan-2-ol;

2-(1-{6-[(4-Methylpyridin-2-yl)amino]pyridin-2-yl}-1H-imidazol-4-yl)propan-2-ol;

2-(1-{6-[(4-Chloropyridin-2-yl)amino]pyridin-2-yl}-1H-imidazol-4-yl)propan-2-ol;

Methyl 1-{6[(4-methylpyridin-2-yl)amino]pyridin-2-yl}-1H-imidazole-4-carboxylate;

N-(1-methylethyl)-1-(3-{[4-(trifluoromethyl)pyrimidin-2-yl]amino}pyridin)-1H-imidazole-4-carboxamide;

2-[1-(3-{[4-(Trifluoromethyl)pyrimidin-2-yl]amino}phenyl)-1H-imidazol-4-yl]propan-2-ol;

2-mMethyl-4-[1-(3-morpholin-4-yl-5-{[4-(trifluoromethyl)pyrimidin-2-yl]amino}phenyl)-1H-imidazol-4-yl]butan-2-ol;

Methyl 3-[1-(3-morpholin-4-yl-5-{[4-(trifluoromethyl)pyrimidin-2-yl]amino}pyridin)-1H-imidazol-4-yl]propanoate;

2-[1-(3-Morpholin-4-yl-5-{[4-(trifluoromethyl)pyrimidin-2-yl]amino}pyridin)-1H-imidazol-4-yl]propan-2-ol;

Methyl 1-(3-morpholin-4-yl-5-{[4-(trifluoromethyl)pyrimidin-2-yl]amino}phenyl)-1H-imidazole-4-carboxylate;

5-hydroxy-5-[1-(3-methyl-5-{[4-(trifluoromethyl)pyrimidin-2-yl]amino}phenyl)-1H-imidazol-4-yl]azepan-2-one;

2-Methyl-2-[1-(3-methyl-5-{[4-(trifluoromethyl)pyrimidin-2-yl]amino}phenyl)-1H-imidazol-4-yl]propanenitrile;

2-Methyl-2-[1-(3-methyl-5-{[4-(trifluoromethyl)pyrimidin-2-yl]amino}phenyl)-1H-imidazol-4-yl]propanoic acid;

N-{3-Methyl-5-[4-(prop-1-en-2-yl)-1H-imidazol-1-yl]phenyl}-4-(trifluoromethyl)pyrimidin-2-amine;

2-[1-(3-Methyl-5-{[4-(trifluoromethyl)pyrimidin-2-yl]amino}phenyl)-1H-imidazol-4-yl]propane-1,2-diol;

3-(1-(6-((4-(Trifluoromethyl)pyridin-2-yl)amino)pyridin-2-yl)-1H-imidazol-4-yl)propanoic acid;

3-(1-(6-((4-Cyclopropylpyridin-2-yl)amino)-4-methylpyridin-2-yl)-1H-imidazol-4-yl)propanoic acid;
4-Hydroxy-4-[1-(4-methyl-6-{[4-(trifluoromethyl)pyridin-2-yl]amino}pyridin-2-yl)-1H-imidazol-4-yl]piperidine-1-carboxamide;
4-Hydroxy-4-[1-(3-methyl-5-{[4-(trifluoromethyl)pyrimidin-2-yl]amino}phenyl)-1H-imidazol-4-yl]piperidine-1-carboxamide;
Ethyl cis-4-hydroxy-4-[1-(3-methyl-5-{[4-(trifluoromethyl)pyrimidin-2-yl]amino}phenyl)-1H-imidazol-4-yl]cyclohexanecarboxylate; and
Cis-4-hydroxy-4-[1-(3-methyl-5-{[4-(trifluoromethyl)pyrimidin-2-yl]amino}phenyl)-1H-imidazol-4-yl]cyclohexanecarboxylic acid.

Another embodiment of the invention is a compound (including pharmaceutically acceptable salts thereof) selected from:
Cis-4-hydroxy-N-methyl-4-[1-(3-methyl-5-{[4-(trifluoromethyl)pyrimidin-2-yl]amino}phenyl)-1H-imidazol-4-yl]cyclohexanecarboxamide;
Trans-4-[1-(3-methyl-5-{[4-(trifluoromethyl)pyrimidin-2-yl]amino}phenyl)-1H-imidazol-4-yl]cyclohexanecarboxylic acid;
Cis-4-[1-(3-methyl-5-{[4-(trifluoromethyl)pyrimidin-2-yl]amino}phenyl)-1H-imidazol-4-yl]cyclohexanecarboxylic acid;
6,6-Dimethyl-4-[1-(3-methyl-5-{[4-(trifluoromethyl)pyrimidin-2-yl]amino}phenyl)-1H-imidazol-4-yl]cyclohex-3-ene-1-carboxylic acid;
Trans-4-[1-hydroxy-1-(1-{3-methyl-5-[(4-methyl-pyrimidin-2-yl)amino]-phenyl}-1H-imidazol-4-yl)ethyl]cyclohexane-carboxylic acid;
Trans-4-{1-hydroxy-1-[1-(3-methyl-5-{[4-(trifluoromethyl)pyrimidin-2-yl]amino}phenyl)-1H-imidazol-4-yl]ethyl}-cyclohexanecarboxylic acid;
{Cis-4-hydroxy-4-[1-(4-methyl-6-{[4-(trifluoromethyl)pyridin-2-yl]amino}pyridin-2-yl)-1H-imidazol-4-yl]cyclohexyl}acetic acid;
{Cis-4-hydroxy-4-[1-(3-methyl-5-{[4-(trifluoromethyl)pyrimidin-2-yl]amino}phenyl)-1H-imidazol-4-yl]cyclohexyl}acetic acid;
Cis-4-hydroxy-4-[1-(4-methyl-6-{[4-(trifluoromethyl)pyridin-2-yl]amino}pyridin-2-yl)-1H-imidazol-4-yl]cyclohexanecarboxylic acid;
Cis-1-[1-(3-methyl-5-{[4-(trifluoromethyl)pyrimidin-2-yl]amino}phenyl)-1H-imidazol-4-yl]cyclohexane-1,4-diol;
Cis-1-(1-{6-[(4-cyclopropylpyridin-2-yl)amino]-4-methylpyridin-2-yl}-1H-imidazol-4-yl)cyclohexane-1,4-diol;
Cis-1-[1-(4-methyl-6-{[4-(trifluoromethyl)pyridin-2-yl]amino}pyridin-2-yl)-1H-imidazol-4-yl]cyclohexane-1,4-diol;
4-[1-(3-Methyl-5-{[4-(trifluoromethyl)pyrimidin-2-yl]amino}phenyl)-1H-imidazol-4-yl]benzoic acid;
5-Hydroxy-5-[1-(3-methyl-5-{[4-(trifluoromethyl)pyrimidin-2-yl]amino}phenyl)-1H-imidazol-4-yl]azepan-2-one;
4-Hydroxy-4-[1-(4-methyl-6-{[4-(trifluoromethyl)pyridin-2-yl]amino}pyridin-2-yl)-1H-imidazol-4-yl]piperidine-1-carboxamide;
4-Hydroxy-4-[1-(3-methyl-5-{[4-(trifluoromethyl)pyrimidin-2-yl]amino}phenyl)-1H-imidazol-4-yl]piperidine-1-carboxamide; and
Cis-4-hydroxy-4-[1-(3-methyl-5-{[4-(trifluoromethyl)pyrimidin-2-yl]amino}phenyl)-1H-imidazol-4-yl]cyclohexanecarboxylic acid.

In the application various terms are as defined below, unless otherwise specified:

"Alkyl" refers to a straight- or branched-chain hydrocarbon radical having the specified number of carbon atoms. Examples of "alkyl" include, but are not limited to, methyl, ethyl, n-propyl, isopropyl, n-butyl, isobutyl, t-butyl, n-pentyl, isopentyl, and the like.

"Carbocycle" refers to a non-aromatic saturated or partially unsaturated monocyclic ring in which all ring atoms are carbon, and the ring being isolated or fused (including ortho-fused, spiro-fused and bridged) to one or two such ring or to a benzene ring. In the case of a polycyclic carbocycle, the attachment point may be on any ring. Examples of carbocycles include, but are not limited to, cyclopropyl, cyclobutyl, cyclopentyl, cyclohexyl, cyclohexenyl, cycloheptyl, cycloheptenyl, bicyclo[3.3.0]octane, indane, bicyclo[3.3.1]nonane, decalin, tetrahydronaphthalene, spiro[3.3]heptane, bicyclo[3.1.0]hexane, adamantane, tricyclo[2.2.1.0$^{2,6}$]heptane, dispiro[2.1.2.3]decane.

"Cycloalkyl" refers to a saturated ring containing the specified number of ring carbon atoms, and no heteroatom. In a like manner the term "$C_{3-6}$ cycloalkyl" refers to a saturated ring having from 3 to 6 ring carbon atoms. Exemplary "cycloalkyl" groups useful in the present invention include, but are not limited to, cyclopropyl, cyclobutyl, cyclopentyl and cyclohexyl.

"Halogen" or "halo" refers to fluorine, chlorine, bromine, or iodine.

"Haloalkyl" refers to an alkyl group as defined above in which one and up to all hydrogen atoms are replaced by a halogen; halogen is as defined herein. Examples of such branched or straight chained haloalkyl groups useful in the present invention include, but are not limited to, methyl, ethyl, propyl, isopropyl, isobutyl and n-butyl substituted independently with one or more halos, e.g., fluoro, chloro, bromo and iodo. Examples of "haloalkyl" include, but are not limited to, fluoromethyl, difluoromethyl, trifluoromethyl, 1-fluoroethyl, 2-fluoroethyl, 2,2-difluoroethyl, 2,2,2-trifluoroethyl, and perfluoro-n-propyl.

"Hydroxyalkyl" refers to an alkyl group as defined above in which one hydrogen on each carbon atom may be replaced by a hydroxy group. Examples of "hydroxyalkyl" include, but are not limited to, hydroxymethyl, hydroxyethyl, propane-1,2-diol.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, and pharmaceutically acceptable excipients.

As used herein, the term "optionally" means that the subsequently described event(s) may or may not occur, and includes both event(s), which occur, and events that do not occur.

As used herein, the term "substituted with one or more groups" refers to substitution with the named substituent or substituents, multiple degrees of substitution, up to replacing all hydrogen atoms with the same or different substituents, being allowed unless the number of substituents is explicitly stated. Where the number of substituents is not explicitly stated, one or more is intended.

Each variable is independently defined each time it occurs within the generic structural formula definitions. For example, when there is more than one $R^7$ substituents on the "A" ring, each substituent is independently selected at each occurrence, and each substituent can be the same or different from the other(s).

The term "Syk inhibitor", is used to mean a compound which inhibits the Syk enzyme.

The term "Syk mediated disease" or a "disorder or disease or condition mediated by inappropriate Syk activity" is used to mean any disease state mediated or modulated by Syk kinase mechanisms. Such disease states may include inflammatory, allergic and autoimmune diseases, for example, asthma, chronic obstructive pulmonary disease (COPD), adult respiratory distress syndrome (ARDs), ulcerative colitis, Crohns disease, bronchitis, dermatitis, allergic rhinitis, psoriasis, scleroderma, urticaria, rheumatoid arthritis, multiple sclerosis, cancer, HIV and lupus, in particular, asthma, chronic obstructive pulmonary disease (COPD), adult respiratory distress syndrome (ARDs), allergic rhinitis and rheumatoid arthritis.

As used herein, "a compound of the invention" means a compound of Formula I or a salt, solvate or physiologically functional derivative thereof.

As used herein, the term "solvate" refers to a complex of variable stoichiometry formed by a solute (in this invention, a compound of Formula I, or a salt thereof) and a solvent. Such solvents for the purpose of the invention may not interfere with the biological activity of the solute. Examples of suitable solvents include, but are not limited to, water, acetone, methanol, ethanol and acetic acid. Preferably the solvent used is a pharmaceutically acceptable solvent. Examples of suitable pharmaceutically acceptable solvents include water, ethanol and acetic acid. Most preferably the solvent is water.

As used herein, the term "physiologically functional derivative" refers to a compound (e.g., a drug precursor) that is transformed in vivo to yield a compound of Formula I or a pharmaceutically acceptable salt, hydrate or solvate of the compound. The transformation may occur by various mechanisms (e.g., by metabolic or chemical processes), such as, for example, through hydrolysis in blood. Prodrugs are such derivatives, and a discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The compounds of formula I may have the ability to crystallize in more than one form, a characteristic known as polymorphism, and it is understood that such polymorphic forms ("polymorphs") are within the scope of Formula I. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

The compounds of Formula I may contain asymmetric or chiral centers, and, therefore, exist in different stereoisomeric forms. It is intended that all stereoisomeric forms of the compounds of Formula I as well as mixtures thereof, including racemic mixtures, form part of the present invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by chromatography employing columns with a chiral stationary phase. Also, some of the compounds of Formula I may be atropisomers (e.g., substituted biaryls) and are considered as part of this invention.

It is also noted that the compounds of Formula I may form tautomers. It is understood that all tautomers and mixtures of tautomers of the compounds of the present invention are included within the scope of the compounds of the present invention. Some of the compounds described herein contain olefinic double bonds, and unless specified otherwise, are meant to include both E and Z geometric isomers.

Whilst the embodiments for each variable have generally been listed above separately for each variable, this invention also includes those compounds in which several or each embodiment in Formula I is selected from each of the embodiments listed above. Therefore, this invention is intended to include all combinations of embodiments for each variable.

The compounds of the present invention may be in the form of and/or may be administered as a pharmaceutically acceptable salt. For a review on suitable salts see Berge et al., J. Pharm. Sci. 1977, 66, 1-19. Typically, the salts of the present invention are pharmaceutically acceptable salts. Salts encompassed within the term "pharmaceutically acceptable salts" refer to non-toxic salts of the compounds of this invention. Suitable pharmaceutically acceptable salts can include acid or base additions salts.

A pharmaceutically acceptable acid addition salt can be formed by reaction of a compound of Formula I with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated, for example, by crystallisation and filtration. A pharmaceutically acceptable acid addition salt of a compound of Formula I can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g., 2-naphthalenesulfonate) or hexanoate salt.

A pharmaceutically acceptable base salt can be formed by reaction of a compound of Formula I with a suitable inorganic or organic base. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Other, non-pharmaceutically acceptable, salts, e.g., oxalates or trifluoroacetates, may also be used, for example, in the isolation of compounds of the invention, and are included within the scope of this invention.

The invention includes within its scope all possible stoichiometric and non-stoichiometric forms of the compounds of Formula I.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates The compounds of Formula I and salts, solvates and physiologically functional derivatives thereof are believed to be inhibitors of Syk activity, and thus be potentially useful in the treatment of diseases and conditions associated with inappropriate Syk activity.

Compound of Formula I or its pharmaceutically acceptable salts and pharmaceutical compositions can be used to treat or prevent a variety of conditions or diseases mediated by Spleen tyrosine kinase (Syk). Such conditions and diseases include, but are not limited to: (1) arthritis, including rheumatoid arthritis, juvenile arthritis, psoriatic arthritis and osteoarthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, adult respiratory distress syndrome, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia including idiopathic thrombopenic purpura, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, immune thrombocytopenic purpura, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma and leukemia (including but not limited to acute myelogenous leukemia, chronic myelogenous leukemia, mantle cell lymphoma, NHL B cell lymphomas (e.g., precursor B-ALL, marginal zone B cell lymphoma, chronic lymphocytic leukemia, diffuse large B cell lymphoma, Burkitt lymphoma, mediastinal large B-cell lymphoma), Hodgkin lymphoma, NK and T cell lymphomas; TEL-Syk and ITK-Syk fusion driven tumors) myelomas including multiple myeloma, myeloproliferative disorders kidney cancer, lung cancer, muscle cancer, bone cancer, bladder cancer, brain cancer, melanoma including oral and metastatic melanoma, Kaposi's sarcoma, proliferative diabetic retinopathy, and angiogenic-associated disorders including solid tumors, and pancreatic cancer; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia; (9) platelet aggregation and diseases associated with or caused by platelet activation, such as arteriosclerosis, thrombosis, intimal hyperplasia and restenosis following vascular injury; (10) conditions associated with cardiovascular diseases, including restenosis, acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like; (11) skin diseases, conditions or disorders including atopic dermatitis, eczema, psoriasis, scleroderma, pruritus and other pruritic conditions; (12) allergic reactions including anaphylaxis, allergic rhinitis, allergic dermatitis, allergic urticaria, angioedema, allergic asthma, or allergic reaction to insect bites, food, drugs, or pollen; (13) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation; (14) low grade scarring including scleroderma, increased fibrosis, keloids, post-surgical scars, pulmonary fibrosis, vascular spasms, migraine, reperfusion injury, and post-myocardial infarction.

The invention thus provides compounds of Formula I and salts, solvates and physiologically functional derivatives thereof for use in therapy, and particularly in the treatment of diseases and conditions mediated by inappropriate Syk activity. The inappropriate Syk activity referred to herein is any Syk activity that deviates from the normal Syk activity expected in a particular mammalian subject. Inappropriate Syk activity may take the form of, for instance, an abnormal increase in activity, or an aberration in the timing and or control of Syk activity. Such inappropriate activity may result then, for example, from overexpression or mutation of the protein kinase leading to inappropriate or uncontrolled activation.

In a further embodiment, the present invention is directed to methods of regulating, modulating, or inhibiting Syk for the prevention and/or treatment of disorders related to unregulated Syk activity.

In a further embodiment, the present invention provides a method of treatment of a mammal suffering from a disorder mediated by Syk activity, which comprises administering to said mammal an effective amount of a compound of Formula I or a pharmaceutically acceptable salt, solvate, or a physiologically functional derivative thereof.

In a further embodiment, the present invention provides for the use of a compound of Formula I, or a pharmaceutically acceptable salt or solvate thereof, or a physiologically functional derivative thereof, in the preparation of a medicament for the treatment of a disorder mediated by Syk activity.

In a further embodiment said disorder mediated by Syk activity is asthma. In a further embodiment said disorder is rheumatoid arthritis. In yet another embodiment, said disorder is cancer. In a further embodiment said disorder is ocular conjunctivitis.

Yet another aspect of the present invention provides a method for treating diseases caused by or associated with Fc receptor signaling cascades, including FceRI and/or FcgRI-mediated degranulation as a therapeutic approach towards the treatment or prevention of diseases characterized by, caused by and/or associated with the release or synthesis of chemical mediators of such Fc receptor signaling cascades or degranulation. In addition, Syk is known to play a critical role in immunotyrosine-based activation motif (ITAM) signaling, B cell receptor signaling, T cell receptor signaling and is an essential component of integrin beta (1), beta (2), and beta (3) signaling in neutrophils. Thus, compounds of the present invention can be used to regulate Fc receptor, ITAM, B cell receptor and integrin signaling cascades, as well as the cellular responses elicited through these signaling cascades. Non-limiting examples of cellular responses that may be regulated or inhibited include respiratory burst, cellular adhesion, cellular degranulation, cell spreading, cell migration, phagocytosis, calcium ion flux, platelet aggregation and cell maturation.

While it is possible that, for use in therapy, a compound of Formula I, as well as salts, solvates and physiological functional derivatives thereof, may be administered as the raw chemical, it is possible to present the active ingredient as a pharmaceutical composition. Accordingly, the invention further provides a pharmaceutical composition, which comprises a compound of Formula I and salts, solvates and physiological functional derivatives thereof, and one or more pharmaceutically acceptable carriers, diluents, or excipients. The compounds of the Formula I and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing a compound of the Formula I, or salts, solvates and physiological functional derivatives thereof, with one or more pharmaceutically acceptable carriers, diluents or excipients.

Pharmaceutical compositions of the present invention may be presented in unit dose forms containing a predetermined amount of active ingredient per unit dose. Such a unit may contain, for example, 5 µg to 3 g, preferably 1 mg to 700 mg, more preferably 5 mg to 100 mg of a compound of the Formula I, depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), rectal, topical, inhaled, nasal, ocular, or parenteral (including intravenous and intramuscular) route. Such compositions may be prepared by any method known in the art of pharmacy, for example by bringing into association the active ingredient with the carrier(s) or excipient(s). Dosage forms include tablets, troches, dispersions, suspensions, solutions, capsules, creams, ointments, aerosols, and the like.

In a further embodiment, the present invention provides a pharmaceutical composition adapted for administration by the oral route, for treating, for example, rheumatoid arthritis.

In a further embodiment, the present invention provides a pharmaceutical composition adapted for administration by the nasal route, for treating, for example, allergic rhinitis.

In a further embodiment, the present invention provides a pharmaceutical composition adapted for administration by the inhaled route, for treating, for example, asthma, COPD or ARDS.

In a further embodiment, the present invention provides a pharmaceutical composition adapted for administration by the ocular route, for treating, diseases of the eye, for example, conjunctivitis.

In a further embodiment, the present invention provides a pharmaceutical composition adapted for administration by the parenteral (including intravenous) route, for treating, for example, cancer.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release, for example, by coating or embedding particulate material in polymers, wax or the like.

The compounds of Formula I, and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of Formula I and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Dosage forms for inhaled administration may conveniently be formulated as aerosols or dry powders.

For compositions suitable and/or adapted for inhaled administration, it is preferred that the compound or salt of Formula I is in a particle-size-reduced form, and more preferably the size-reduced form is obtained or obtainable by micronisation. The preferable particle size of the size-reduced (e.g., micronised) compound or salt or solvate is defined by a D50 value of about 0.5 to about 10 microns (for example as measured using laser diffraction).

Aerosol formulations, e.g., for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g., co-solvents and/or surfactants to improve the dispersion characteristics and homogeneity of suspension formulations. Solution formulations may also require the addition of co-solvents such as ethanol. Other excipient modifiers may also be incorporated to improve, for example, the stability and/or taste and/or fine particle mass characteristics (amount and/or profile) of the formulation.

For pharmaceutical compositions suitable and/or adapted for inhaled administration, it is preferred that the pharmaceutical composition is a dry powder inhalable composition. Such a composition can comprise a powder base such as lactose, glucose, trehalose, mannitol or starch, the compound of Formula I or salt or solvate thereof (preferably in particle-size-reduced form, e.g., in micronised form), and optionally a performance modifier such as L-leucine or another amino acid, and/or metals salts of stearic acid such as magnesium or calcium stearate. Preferably, the dry powder inhalable composition comprises a dry powder blend of lactose and the compound of Formula I or salt thereof. The lactose is preferably lactose hydrate e.g., lactose monohydrate and/or is preferably inhalation-grade and/or fine-grade lactose. Preferably, the particle size of the lactose is defined by 90% or more (by weight or by volume) of the lactose particles being less than 1000 microns (micrometers) (e.g., 10-1000 microns e.g., 30-1000 microns) in diameter, and/or 50% or more of the lactose particles being less than 500 microns (e.g., 10-500 microns) in diameter. More preferably, the particle size of the lactose is defined by 90% or more of the lactose particles being less than 300 microns (e.g., 10-300 microns e.g., 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is preferable that about 3 to about 30% (e.g., about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 J D Zwolle, Netherlands).

Optionally, in particular for dry powder inhalable compositions, a pharmaceutical composition for inhaled administration can be incorporated into a plurality of sealed dose containers (e.g., containing the dry powder composition) mounted longitudinally in a strip or ribbon inside a suitable inhalation device. The container is rupturable or peel-openable on demand and the dose of e.g., the dry powder composition can be administered by inhalation via the device such as the DISKUS® device (GlaxoSmithKline). Other dry powder inhalers are well known to those of ordinary skill in the art, and many such devices are commercially available, with representative devices including Aerolizer® (Novartis), Airmax™ (WAX), ClickHaler® (Innovata Biomed), Diskhaler® (GlaxoSmithKline), Accuhaler (GlaxoSmithKline), Easyhaler® (Orion Pharma), Eclipse™ (Aventis), FlowCaps® (Hovione), Handihaler® (Boehringer Ingelheim), Pulvinal® (Chiesi), Rotahaler® (GlaxoSmithKline), SkyeHaler™ or Certihaler™ (SkyePharma), Twisthaler® (Schering-Plough), Turbuhaler® (AstraZeneca), Ultrahaler® (Aventis), and the like.

Dosage forms for ocular administration may be formulated as solutions or suspensions with excipients suitable for ophthalmic use.

Dosage forms for nasal administration may conveniently be formulated as aerosols, solutions, drops, gels or dry powders.

Pharmaceutical compositions adapted for administration by inhalation include fine particle dusts or mists, which may be generated by means of various types of metered, dose pressurised aerosols, nebulizers or insufflators.

For pharmaceutical compositions suitable and/or adapted for intranasal administration, the compound of Formula I or a pharmaceutically acceptable salt or solvate thereof may be formulated as a fluid formulation for delivery from a fluid dispenser. Such fluid dispensers may have, for example, a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. A particularly preferred fluid dispenser is of the general type illustrated in FIGS. 30-40 of WO-A-2005/044354.

The following are examples of representative pharmaceutical dosage forms for the compounds of this invention:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Inhalation Aerosol | Per dose |
|---|---|
| Compound of Formula I | 100 mcg |
| Oleic Acid | 5 mcg |
| Ethanol | 1 mg |
| HFA 227 (1,1,1,2,3,3,3-heptafluoropropane) | 75 mg |

| Dry Powder Inhalation Aerosol | Per dose |
|---|---|
| Compound of Formula I | 100 mcg |
| Lactose | 12.5 mg |

It will be appreciated that when the compound of the present invention is administered in combination with other therapeutic agents normally administered by the inhaled, intravenous, oral or intranasal route, that the resultant pharmaceutical composition may be administered by the same routes.

It should be understood that in addition to the ingredients particularly mentioned above, the compositions may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of Formula I for the treatment of diseases or conditions associated with inappropriate Syk activity, will generally be in the range of 5 μg to 100 mg/kg body weight of recipient (mammal) per day and more usually in the range of 5 μg to 10 mg/kg body weight per day. This amount may be given in a single dose per day or more usually in a number (such as two, three, four, five or six) of sub-doses per day such that the total daily dose is the same. An effective amount of a salt or solvate, thereof, may be determined as a proportion of the effective amount of the compound of Formula I per se.

Compounds of the present invention, and their salts and solvates, and physiologically functional derivatives thereof, may be employed alone or in combination with other therapeutic agents for the treatment of diseases and conditions associated with inappropriate Syk activity. Combination therapies according to the present invention thus comprise the administration of at least one compound of Formula I or a pharmaceutically acceptable salt or solvate thereof, or a physiologically functional derivative thereof, and the use of at least one other pharmaceutically active agent. The compound(s) of Formula I and the other pharmaceutically active agent(s) may be administered together or separately and, when administered separately this may occur simultaneously or sequentially in any order. The amounts of the compound(s) of Formula I and the other pharmaceutically active agent(s) and the relative timings of administration will be selected in order to achieve the desired combined therapeutic effect.

For the treatment of the inflammatory diseases, rheumatoid arthritis, psoriasis, inflammatory bowel disease, COPD, asthma and allergic rhinitis a compound of Formula I may be combined with one or more other active agents such as: (1) TNF-α inhibitors such as infliximab (Remicade®), etanercept (Enbrel®), adalimumab (Humira®), certolizumab pegol (Cimzia®), and golimumab (Simponi®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, etodolac, azapropazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast, cilomilast, AWD-12-281 (Elbion), and PD-168787 (Pfizer); (8) antihistaminic H1 receptor antagonists such as cetirizine, levocetirizine, loratadine, desloratadine, fexofenadine, astemizole, azelastine, levocabastine, olopatidine, methapyrilene and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclidinium bromide, glycopyrrolate, (R,R)-glycopyrrolate, pirenzepine, and telenzepine; (11) β-adrenoceptor agonists such as metaproterenol, isoproterenol, isoprenaline, albuterol, formoterol (particularly the fumarate salt), salmeterol (particularly the xinafoate salt), terbutaline, orciprenaline, bitolterol mesylate, fenoterol, and pirbuterol, or methylxanthanines including theophylline and aminophylline, sodium cromoglycate; (12) insulin-like growth factor type I (IGF-1) mimetic; (13) glucocorticosteroids, especially inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate; (14) kinase inhibitors such as inhibitors of the Janus Kinases (JAK 1 and/or JAK2 and/or JAK 3 and/or TYK2) such as tofacitinib (Pfizer), baricitinib (Incyte), VX-509 (Vertex), ASP-015K (Astellas), GLPG0634 (Galapagos), SB-1578 (SBIO), and AC-430 (Ambit Biosciences); p38 MAPK and IKK2; (15) B-cell targeting biologics such as rituximab (Rituxan®); (16) selective costimulation modulators such as abatacept (Orencia); (17) interleukin inhibitors, such as IL-1 inhibitor anakinra (Kineret) and IL-6 inhibitor tocilizumab (Actemra).

The present invention also provides for so-called "triple combination" therapy, comprising a compound of Formula I or a pharmaceutically acceptable salt thereof together with beta$_2$-adrenoreceptor agonist and an anti-inflammatory corticosteroid. Preferably this combination is for treatment and/or prophylaxis of asthma, COPD or allergic rhinitis. The beta$_2$-adrenoreceptor agonist and/or the anti-inflammatory corticosteroid can be as described above and/or as described in WO 03/030939 A1. Representative examples of such a "triple" combination are a compound of Formula I or a pharmaceutically acceptable salt thereof in combination with the components of Advair® (salmeterol xinafoate and fluticasone propionate), Symbicort® (budesonide and formoterol fumarate), or Dulera® (mometasone furoate and formoterol fumarate) e.g.

For the treatment of cancer a compound of Formula I may be combined with one or more of an anticancer agent. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: (1) estrogen receptor modulator such as diethylstibestral, tamoxifen, raloxifene, idoxifene, LY353381, LY117081, toremifene, fluoxymestero, and SH646; (2) other hormonal agents including aromatase inhibitors (e.g., aminoglutethimide, tetrazole anastrozole, letrozole and exemestane), luteinizing hormone release hormone (LHRH) analogues, ketoconazole, goserelin acetate, leuprolide, megestrol acetate and mifepristone; (3) androgen receptor modulator such as finasteride and other 5α-reductase inhibitors, nilutamide, flutamide, bicalutamide, liarozole, and abiraterone acetate; (4) retinoid receptor modulator such as bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide; (5) antiproliferative agent such as antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, aminopterin, 5-fluorouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone; (6) prenyl-protein transferase inhibitor including farnesyl-protein transferase (FPTase), geranylgeranyl-protein transferase type I (GGPTase-I), and geranylgeranyl-protein transferase type-II (GGPTase-II, also called Rab GGPTase); (7) HMG-CoA reductase inhibitor such as lovastatin, simvastatin, pravastatin, atorvastatin, fluvastatin and rosuvastatin; (8) angiogenesis inhibitor such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, steroidal anti-inflammatories, carboxyamidotriazole, combretastatin A-4, squalamine, 6-O-chloroacetyl-carbonyl)-fumagillol, thalidomide, angiostatin, troponin-1, angiotensin II antagonists, heparin, carboxypeptidase U inhibitors, and antibodies to VEGF, endostatin, ukrain, ranpirnase, IM862, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, and 3-[(2,4-dimethylpyrrol-5-yl)methylene]-2-indolinone (SU5416); (9) PPAR-γ agonists, PPAR-δ agonists, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and (2R)-7-(3-(2-chloro-4-(4-fluorophenoxy)phenoxy)propoxy)-2-ethylchromane-2-carboxylic acid (disclosed in U.S. Ser. Nos. 60/235,708 and 60/244,697); (9) inhibitor of inherent multidrug resistance including inhibitors of p-glycoprotein (P-gp), such as LY335979, XR9576, OC144-093, R101922, VX853 and PSC833 (valspodar); (10) inhibitor of cell proliferation and survival signaling such as inhibitors of EGFR (for example gefitinib and erlotinib), inhibitors of ERB-2 (for example trastuzumab), inhibitors of IGF1R such as MK-0646 (dalotuzumab), inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573); (11) a bisphosphonate such as etidronate, pamidronate, alendronate, risedronate, zoledronate, ibandronate, incadronate or cimadronate, clodronate, EB-1053, minodronate, neridronate, piridronate and tiludronate; (12) γ-secretase inhibitors, (13) agents that interfere with receptor tyrosine kinases (RTKs) including inhibitors of c-Kit, Eph, PDGF, Flt3 and c-Met; (14) agent that interferes with a cell cycle checkpoint including inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032; (15) BTK inhibitors such as PCI32765, AVL-292 and AVL-101; (16) PARP inhibitors including iniparib, olaparib, AGO14699, ABT888 and MK4827; (16) ERK inhibitors; (17) mTOR inhibitors such as sirolimus, ridaforolimus, temsirolimus, everolimus; (18) cytotoxic/cytostatic agents.

"Cytotoxic/cytostatic agents" refers to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin.

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, 2,3-(methylenedioxy)-5-methyl-7-hydroxy-8-methoxybenzo[c]-phenanthridinium, 5-(3-aminopropylamino)-7,10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, vorinostat, trichostatin A, oxamflatin, PXD101, MG98, valproic acid and scriptaid.

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N6-[4-deoxy-4-[N2-[2,4-tetradecadienoyl]glycylamino]-L-glycero-B-L-manno-heptopyranosyl]adenine, aplidine, ecteinascidin, troxacitabine, aminopterin, 5-fluorouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, swainsonine, lometrexol, dexrazoxane, methioninase, and 3-aminopyridine-2-carboxaldehyde thiosemicarbazone.

Non-limiting examples of suitable agents used in cancer therapy that may be combined with compounds of Formula I include, but are not limited to, abarelix; aldesleukin; alemtuzumab; alitretinoin; allopurinol; altretamine; amifostine; anastrozole; arsenic trioxide; asparaginase; azacitidine; bendamustine; bevacuzimab; bexarotene; bleomycin; bortezomib; busulfan; calusterone; capecitabine; carboplatin; carmustine; cetuximab; chlorambucil; cisplatin; cladribine; clofarabine; cyclophosphamide; cytarabine; dacarbazine; dactinomycin, actinomycin D; dalteparin; darbepoetin alfa; dasatinib; daunorubicin; degarelix; denileukin diftitox; dexrazoxane; docetaxel; doxorubicin; dromostanolone propionate; eculizumab; Elliott's B Solution; eltrombopag; epirubicin; epoetin alfa; erlotinib; estramustine; etoposide phosphate; etoposide; everolimus; exemestane; filgrastim; floxuridine; fludarabine; fluorouracil; fulvestrant; gefitinib; gemcitabine; gemtuzumab ozogamicin; goserelin acetate; histrelin acetate; hydroxyurea; ibritumomab tiuxetan; idarubicin; ifosfamide; imatinib mesylate; interferon alfa 2a; interferon alfa-2b; irinotecan; ixabepilone; lapatinib; lenalidomide; letrozole; leucovorin; leuprolide acetate; levamisole; lomustine; meclorethamine, nitrogen mustard; megestrol acetate; melphalan, L-PAM; mercaptopurine; mesna; methotrexate; methoxsalen; mitomycin C; mitotane; mitoxantrone; nandrolone phenpropionate; nelarabine; nilotinib; Nofetumomab; ofatumumab; oprelvekin; oxaliplatin; paclitaxel; palifermin; pamidronat; panitumumab; pazopanib; pegademase; pegaspargase; Pegfilgrastim; pemetrexed disodium; pentostatin; pipobroman; plerixafor; plicamycin, mithramycin); porfimer sodium; pralatrexate; procarbazine; quinacrine; Rasburicase; raloxifene hydrochloride; Rituximab; romidepsin; romiplostim; sargramostim; sargramostim; satraplatin; sorafenib; streptozocin; sunitinib maleate; tamoxifen; temozolomide; temsirolimus; teniposide; testolactone; thioguanine; thiotepa; topotecan; toremifene; tositumomab; trastuzumab; tretinoin; uracil mustard; valrubicin; vinblastine; vincristine; vinorelbine; vorinostat; and zoledronate.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Syk inhibition may be determined using the following assay protocol:
Biological Assay
Homogeneous Time-Resolved Fluorescence (HTRF) Assay for the Recombinant Human Syk Enzyme:

A recombinant GST-hSyk fusion protein was used to measure potency of compounds to inhibit human Syk activity. The recombinant human GST-Syk (Carna Biosciences #08-176) (5 μM final concentration) was incubated with various concentrations of the inhibitor diluted in DMSO (0.1% final concentration) for 10 minutes at room temperature in 15 mM Tris-HCl (pH 7.5), 0.01% tween 20, 2 mM DTT in 384 well plate format. To initiate the reaction the biotinylated substrate peptide (250 nM final concentration) that contains the phosphorylation site for Syk was added with magnesium (5 mM final concentration) and ATP (25 μM final concentration). Final volume of the reaction was 10 μL. Phosphorylation of the peptide was allowed to proceed for 45 minutes at room temperature. To quench the reaction and detect the phosphorylated product, 2 nM of a Europium-anti-phosphotyrosine antibody (Perkin Elmer #AD0161) and 70 nM SA-APC (Perkin-Elmer #CR130-100) were added together in 15 mM Tris pH 7.5, 40 mM EDTA, 0.01% tween 20. Final volume of the quenching solution was 10 μL. The resulting HTRF signal was measured after 30 minutes on an EnVision (Perkin-Elmer) reader using a time-resolved fluorescence protocol. $IC_{50}$ was determined following 10-dose titration (10 μM to 0.508 nM) and four parameter logistic curve fitting using the Merck Assay Data Analyzer. The rhSyk activity ($IC_{50}$) is expressed as +++ (100 nM or less), ++ (between 100 and 1000 nM), + (between 1 and 10 μM).

| Example | rhSYK Activity |
|---|---|
| 1 | +++ |
| 2 (trans) | +++ |
| 2 (cis) | +++ |
| 3 | +++ |
| 4 | +++ |
| 5 (isomer 1) | +++ |
| 5 (isomer 2) | +++ |
| 6 | +++ |
| 7 | +++ |
| 8 | +++ |
| 9 | +++ |
| 10 | +++ |
| 11 | ++ |
| 12 | ++ |
| 13 | +++ |
| 14 | +++ |
| 15 | +++ |
| 16 | +++ |
| 17 | +++ |
| 18 | +++ |
| 19 | ++ |
| 20 | +++ |
| 21 | +++ |
| 22 | +++ |
| 23 | +++ |
| 24 | ++ |
| 25 | +++ |
| 26 | +++ |
| 27 | +++ |
| 28 | +++ |
| 29 | +++ |
| 30 | +++ |
| 31 | +++ |
| 32 | +++ |
| 33 | +++ |
| 34 | +++ |
| 35 | +++ |
| 36 | +++ |
| 37 | +++ |
| 38 | +++ |
| 39 | +++ |
| 40 | +++ |
| 41 | +++ |
| 42 | +++ |
| 43 | +++ |
| 44 | +++ |
| 45 | +++ |
| 46 | +++ |
| 47 | +++ |
| 48 | +++ |
| 49 | ++ |
| 50 | +++ |
| 51 | +++ |
| 52 | +++ |
| 53 | +++ |
| 54 | +++ |
| 55 | +++ |
| 56 | +++ |
| 57 | +++ |
| 58 | ++ |
| 59 | +++ |
| 60 | ++ |
| 61 | +++ |
| 62 | +++ |
| 63 | +++ |
| 64 | +++ |
| 65 | +++ |
| 66 | ++ |
| 67 | +++ |
| 68 | ++ |
| 69 | ++ |
| 70 | ++ |
| 71 | +++ |
| 72 | ++ |
| 73 | +++ |
| 74 | ++ |
| 75 | +++ |
| 76 | +++ |
| 77 | +++ |
| 78 | +++ |
| 79 | +++ |
| 80 | +++ |
| 81 | +++ |
| 82 | +++ |
| 83 | +++ |
| 84 | +++ |
| 85 | +++ |
| 86 | +++ |
| 87 | +++ |
| 88 | +++ |
| 89 | ++ |
| 90 | +++ |
| 91 | ++ |
| 92 | +++ |
| 93 | +++ |
| 94 | +++ |
| 95 | +++ |
| 96 | +++ |
| 97 | +++ |
| 98 | +++ |
| 99 | +++ |
| 100 | ++ |
| 101 | +++ |
| 102 | ++ |
| 103 | ++ |
| 104 | ++ |
| 105 | +++ |
| 106 | +++ |
| 107 | +++ |
| 108 | ++ |
| 109 | +++ |
| 110 | ++ |
| 111 | +++ |
| 112 | +++ |
| 113 | +++ |
| 114 | +++ |
| 115 | +++ |
| 116 | +++ |
| 117 | +++ |

IC$_{50}$ values are also provided for the following representative compounds:

| Example | rhSYK IC$_{50}$ |
|---|---|
| 1 | 6.1 |
| 1, Step 1 | 12.7 |
| 1, Step 2 | 1.0 |
| 2 (trans) | 1.2 |
| 2 (cis) | 12.5 |
| 4 | 0.9 |
| 9 | 14.96 |
| 10 | 1.778 |
| 14 | 0.8614 |
| 16 | 1.64 |
| 27 | 0.757 |
| 37 | 3.7 |
| 45 | 1.384 |
| 62 | 1.362 |
| 71 | 1.683 |
| 109 | 19.7 |
| 116 | 3.6 |
| 117 | 9.0 |

The suitability of the compounds of Formula I as prodrugs of Syk inhibitors can be tested as described below.

Analysis of Hydrolysis of Prodrug to Parent Species

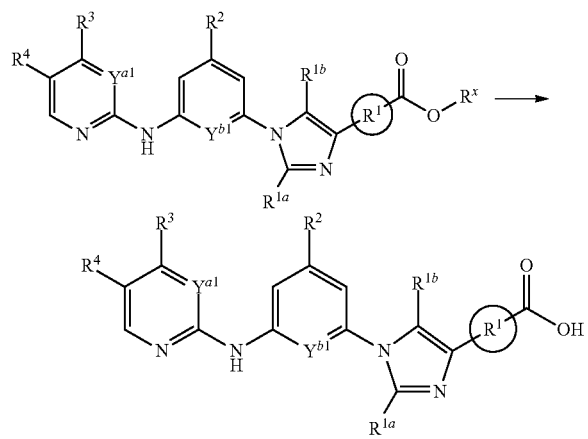

Hydrolysis Assay:

The stability of prodrugs is investigated in human liver S9 microsomes. Incubations of prodrugs (10 µM) with liver S9 (1 mg protein/mL) are carried out at 37° C. in a phosphate buffer, pH 7.4, containing 1 mM NADPH. Control incubations contain BSA (1.1 mg/mL) instead of liver S9 microsomes. Aliquots are removed at 0, 5, 15, 30, 60 and 120 min, treat with 4 volumes of acetonitrile containing 2% formic acid and an internal standard, and centrifuge. The supernatants are analyzed by LC-MS/MS for prodrug disappearance and appearance of active drug. The half-life of the prodrug is calculated from the % prodrug remaining at different time points calculated from on the peak area ratio relative to t=0. The amount of active drug generated at the different time points is determined using a standard curve.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Examples.

Compounds of general Formula I may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) Protecting Groups in Organic Synthesis, John Wiley & Sons). These groups are removed at a convenient stage of the compound synthesis using methods that are readily apparent to those skilled in the art. The selection of protecting groups as well as the reaction conditions and order of reaction steps shall be consistent with the preparation of compounds of Formula I. Those skilled in the art will recognize if a stereocenter exists in compounds of Formula I. Accordingly, the present invention includes all possible stereoisomers and includes not only mixtures of stereoisomers (such as racemic compounds) but the individual stereoisomers as well. When a compound is desired as a single enantiomer, it may be obtained by stereospecific or stereoselective synthesis or by resolution of the final product or any convenient intermediate. Resolution of the final product, an intermediate, or a starting material may be affected by any suitable method known in the art. See, for example, Stereochemistry of Organic Compounds by E. L. Eliel, S. H. Wilen, and L. N. Mander (Wiley-Interscience, 1994).

The following abbreviations are used in the schemes and examples: Ac=Acetyl; AcOH=Acetic acid; Bn=benzyl; Boc (t-Boc)=t-butyloxycarbonyl; BOP=(Benzotriazol-1-yloxy)-tris(dimethylamino)phosphonium hexafluorophosphate; DAST=(Diethylamino)sulfur trifluoride; dba=dibenzylideneacetone; DCE=1,2-dichloroethane; DCM=Dichloromethane; Dibal/Dibal-H=Diisobutylaluminum hydride; DIPEA/DIEA=Diisopropylethylamine; DMAP=N,N-dimethylaminopyridine; DME=1,2-dimethoxyethane; DMF=Dimethyl formamide; DMSO=Dimethylsulfoxide; Dppf=1,1'-Bis(diphenylphosphino)ferrocene; EDC=N-(3-Dimethylaminopropyl)-N'-ethylcarbodiimide; EtOAc=Ethyl acetate; HATU=N,N,N',N'-Tetramethyl-O-(7-azabenzotriazol-1-yl)uronium hexafluorophosphate; HMDS=Hexamethyldisilazane; HOBT=1-Hydroxybenzotriazole; IPA=Isopropyl alcohol; LDA=Lithium diisopropylamide; mCPBA=Meta-chloroperoxy-benzoic acid; Ms=Methanesulfonyl (mesyl); MTBE=Methyl t-butyl ether; NBS=N-bromo-succinimide; Ph=phenyl; TBAF=t-butylammonium fluoride; TBDMS/TBS=t-butyl dimethylsilyl; TFA=Trifluoroacetic acid/trifluoroacetate; THF=Tetrahydrofuran; TLC=Thin-layer chromatography; TMS=Trimethylsilyl; Ts=Toluenesulfonyl (tosyl); TSA=p-toluenesulfonic acid. Abbreviations for alkyl/cycloalkyl groups: Me=methyl, Et=ethyl, nPr=n-propyl, iPr=isopropyl, nBu=n-butyl, t-Bu=tertiary butyl, cPr=cyclopropyl, cBu=cyclobutyl, cPen=cyclopentyl, cHex=cyclohexyl, cHept=cycloheptyl.

Scheme 1

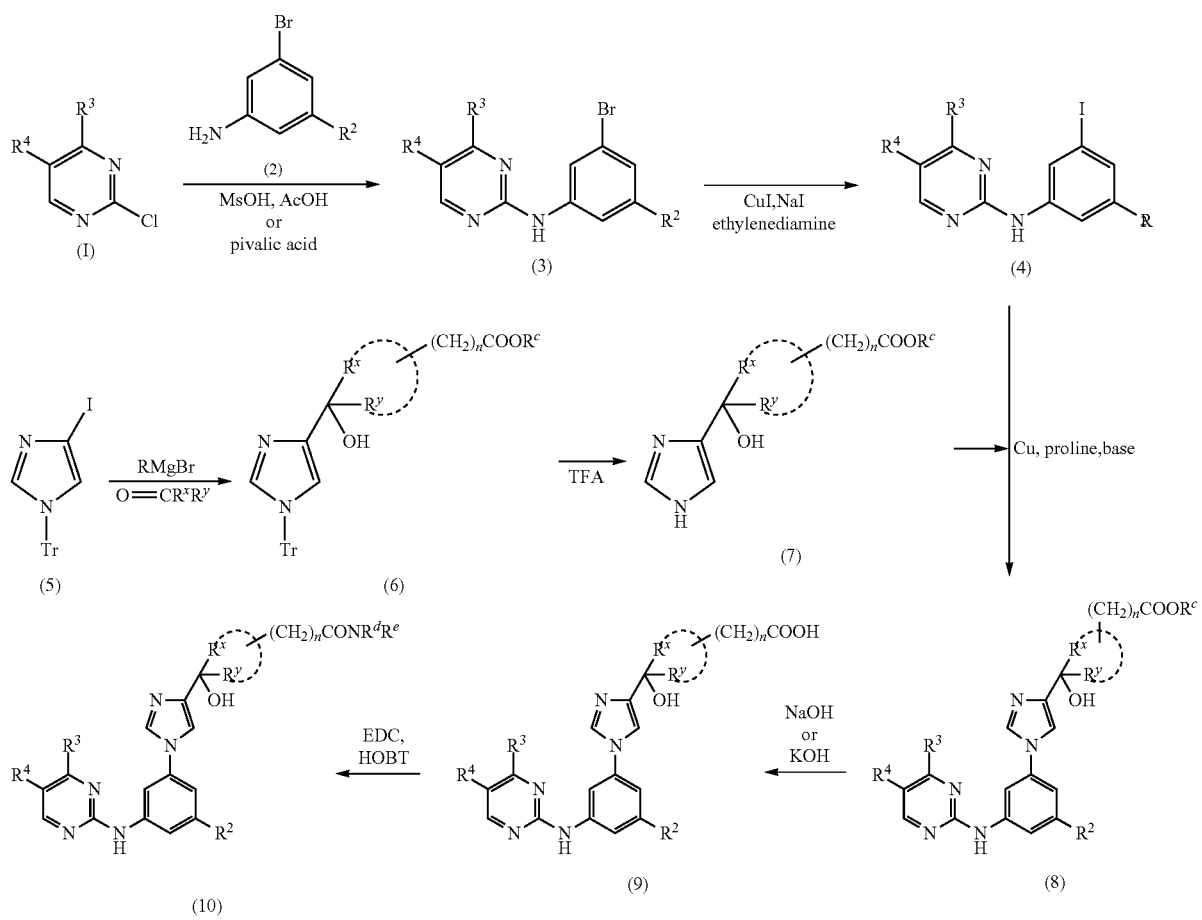

Compounds (3) are prepared by $S_nAr$ reaction of commercially available or prepared pyrimidines (1) with anilines (2). Halogen conversion utilizing CuI, NaI provides iodo intermediates (4). Compounds (7) are prepared from imidazole (5), an alkylmagnesium halide and commercially available or prepared ketones to afford the protected alcohols (6) which are deprotected with trifluoroacetic acid to give alcohols (7). Copper coupling of compounds (7) and (4) provides compounds (8). Hydrolysis under basic conditions provides the acids (9). Amides (10) are formed by treatment of the acids (9) with amide coupling reagents such as EDC and HOBt.

Scheme 2

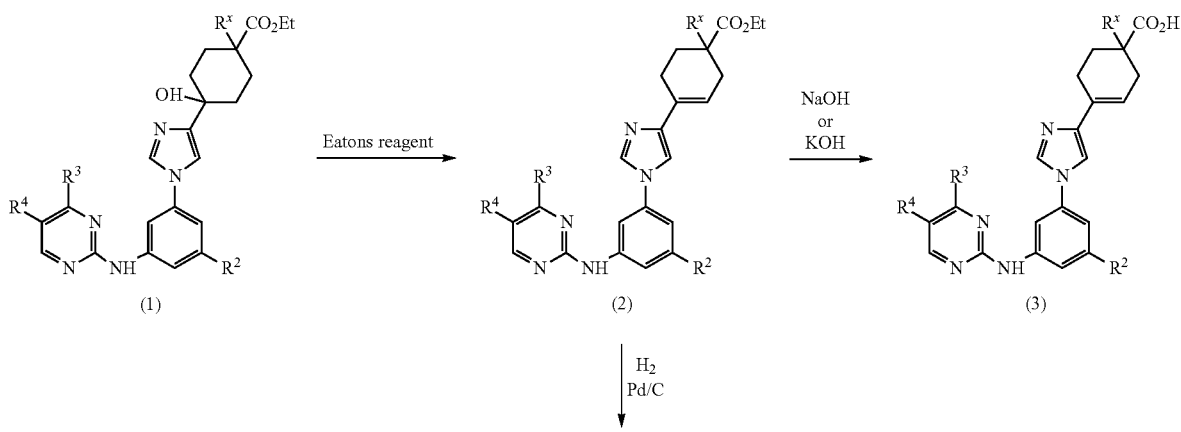

-continued
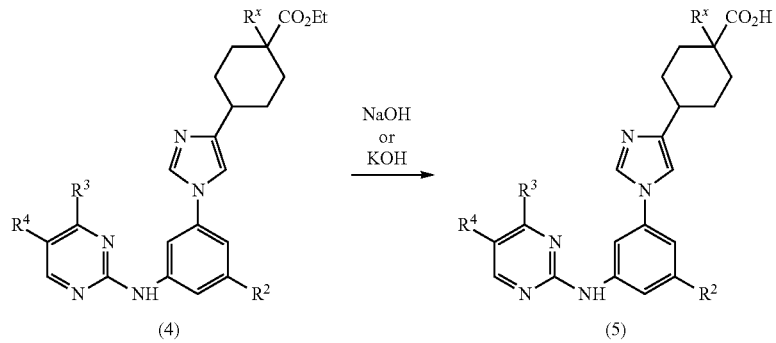
Compounds (3) are prepared by treatment of compounds (1) with Eatons reagent to give (2) followed by hydrolysis with base to give acids (3). Hydrogenation of compounds (2) using a Pd catalyst gave compounds (4) which upon hydrolysis with base provided compounds of the general structure (5).
Scheme 3
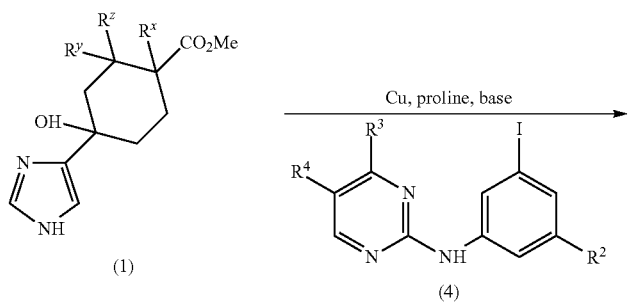
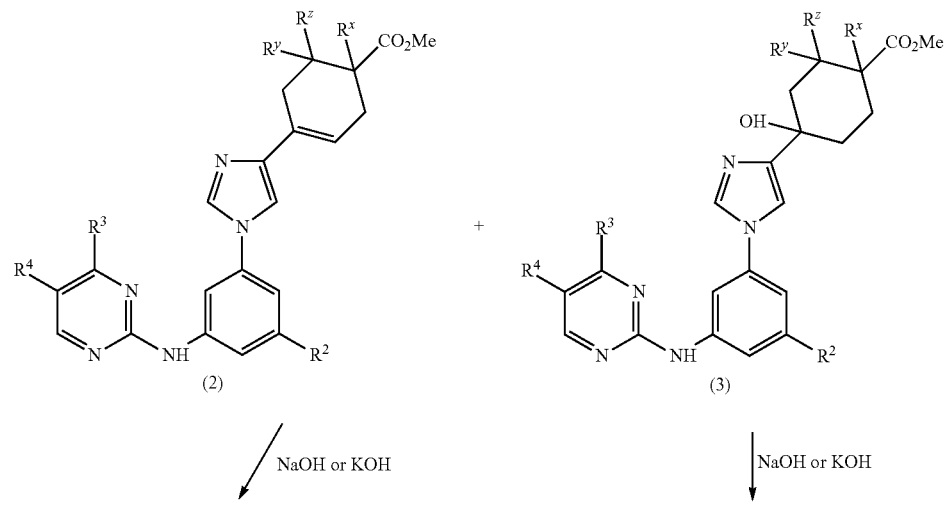

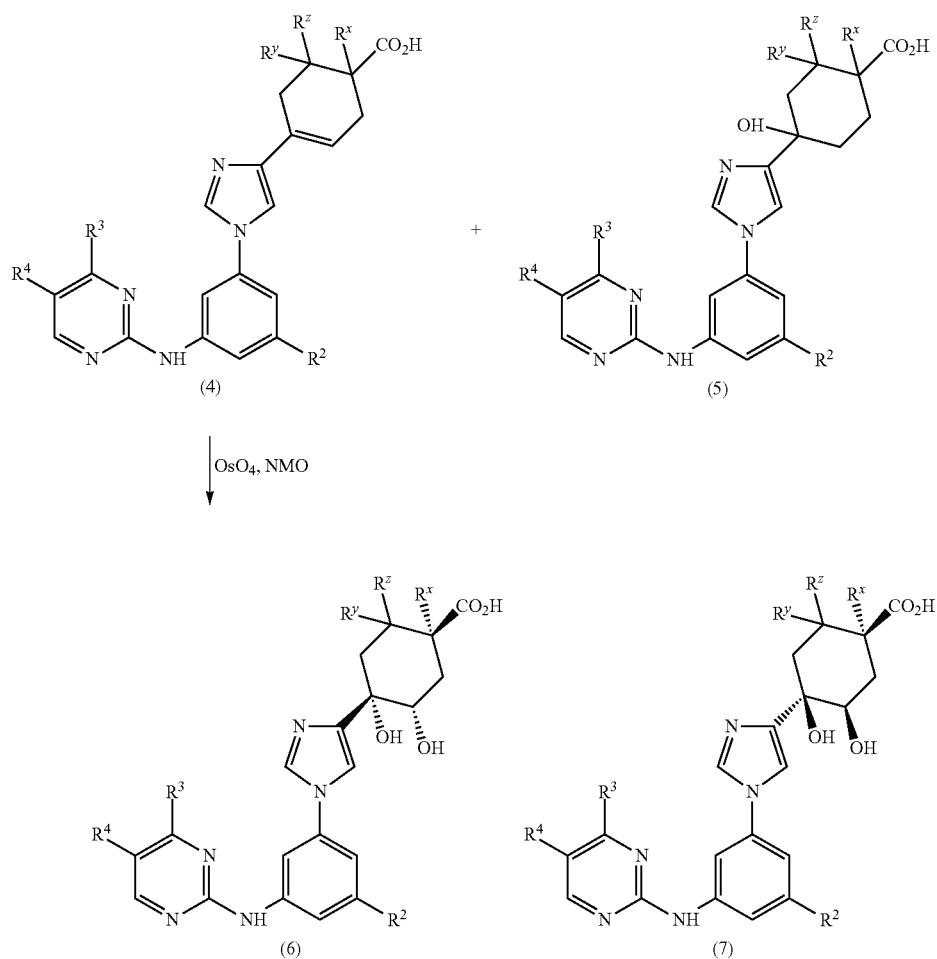
Copper coupling of imidazoles (1) and iodides (4) provides both compounds (2) and (3). Hydrolysis under basic conditions provides the acids (4) and (5). Treatment of compounds (4) with osmium tetroxide and NMO provided both (6) and (7).
Scheme 4
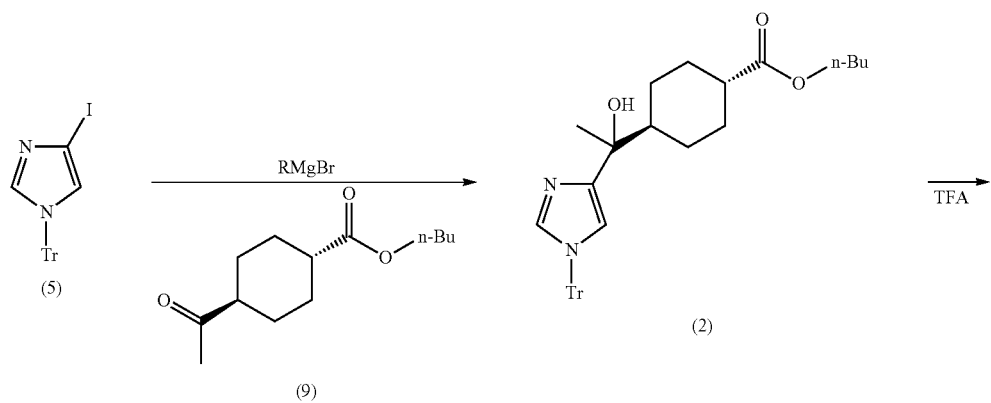

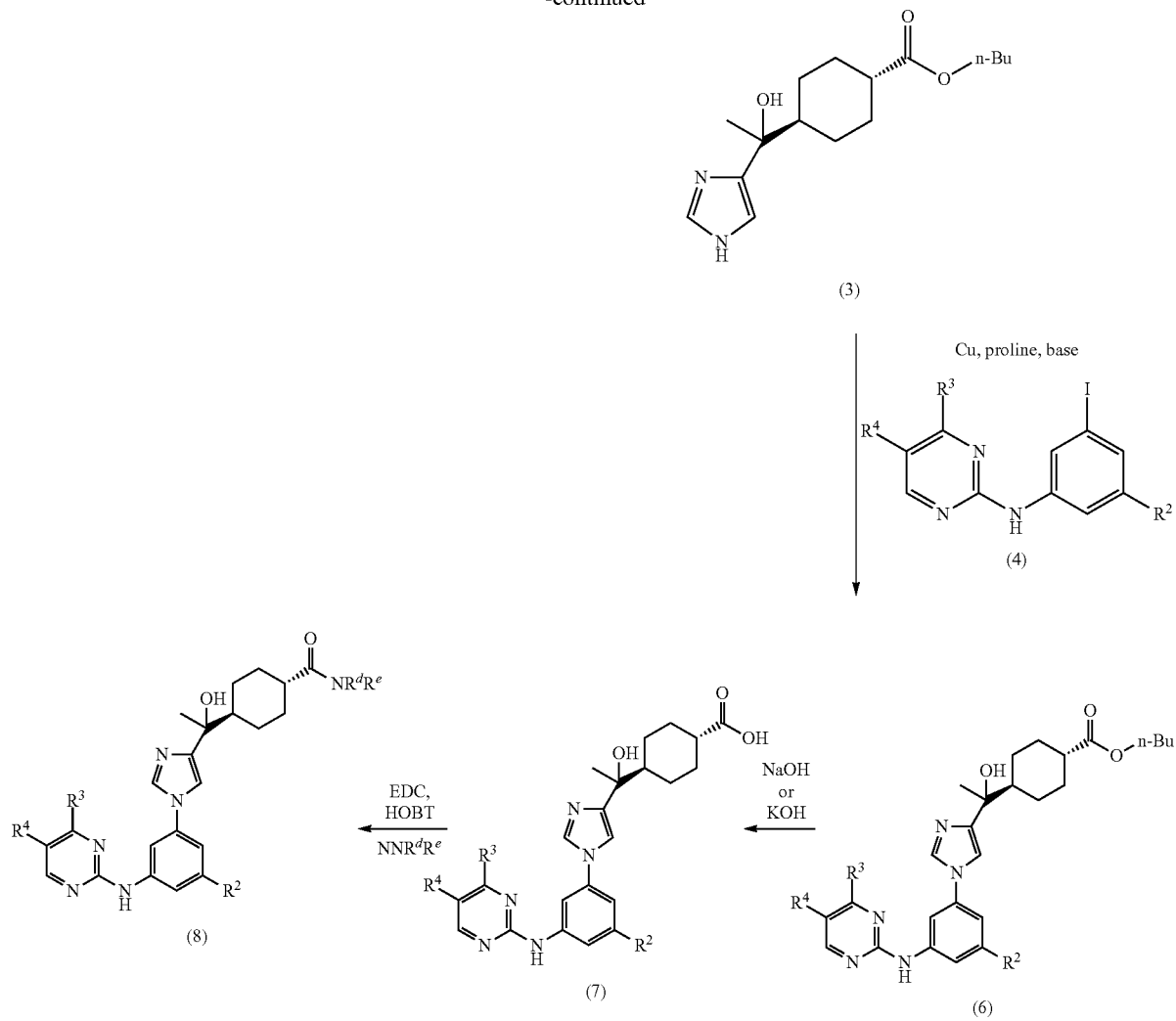

Compound (3) is prepared from imidazole (5), an alkyl-magnesium halide and ketone (9) to afford the protected alcohol (2) which is deprotected with trifluoroacetic acid to give alcohol (3). Copper coupling of compounds (3) and (4) provides compounds (6). Hydrolysis under basic conditions provides the acids (7). Amides (8) are formed by treatment of acids (7) and an amine with amide coupling reagents such as EDC and HOBt.

Scheme 5

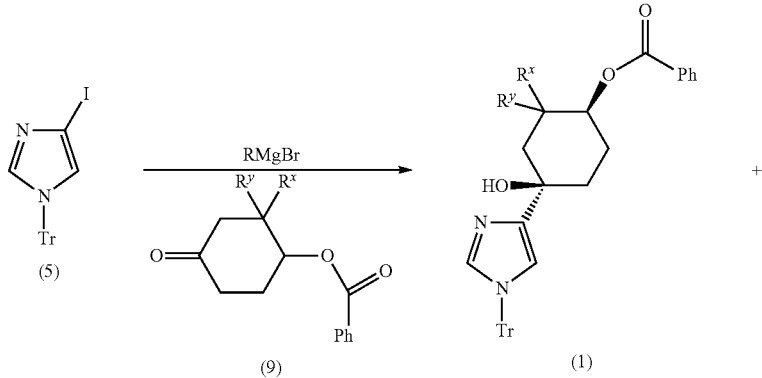

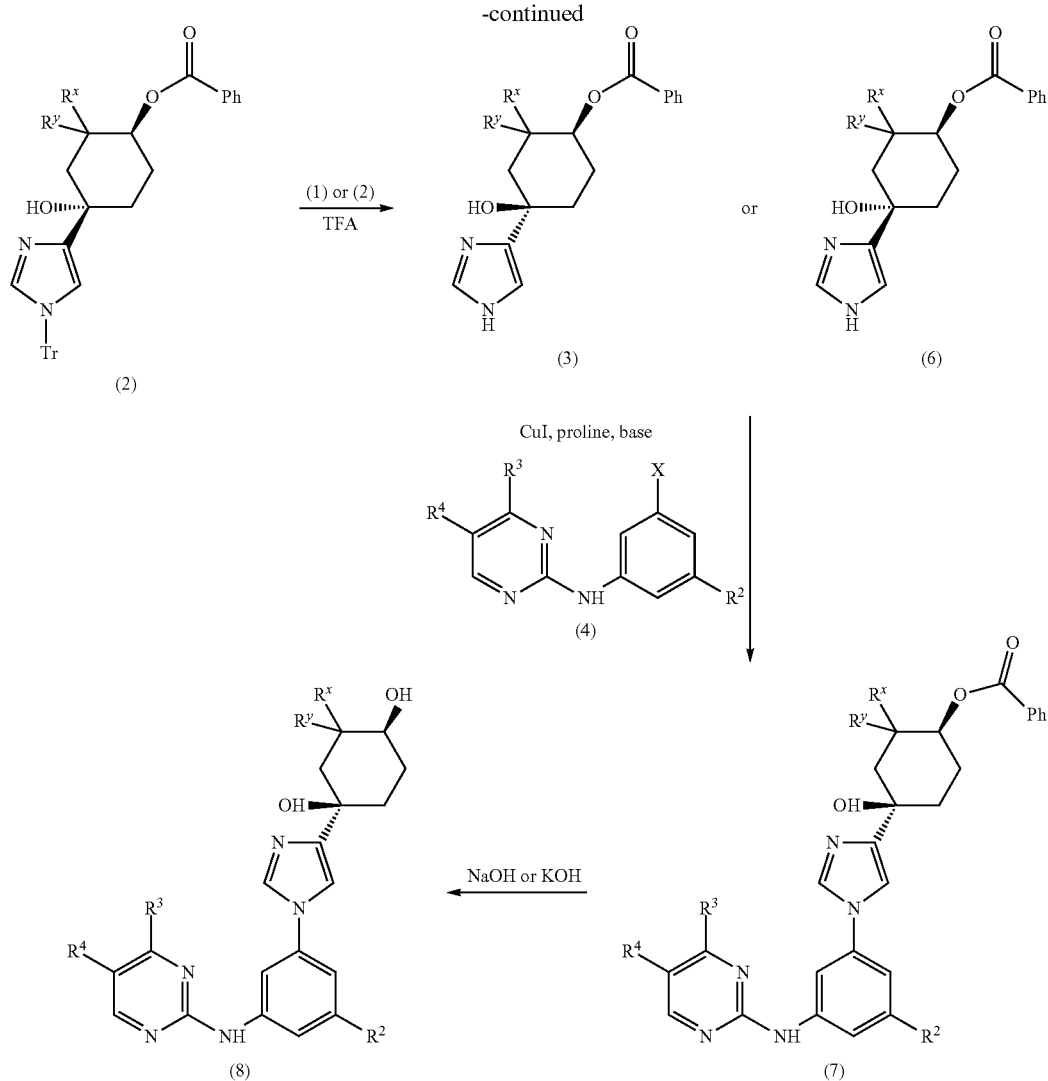

Compounds (3) and (6) are prepared from imidazole (5), an alkylmagnesium halide and ketone (9) to afford the protected alcohols (1) and (2) which are separated by chromatography. Compounds (1) or (2) are deprotected with trifluoroacetic acid to give alcohols (3) or (6). Copper coupling of compounds (3) or (6) with intermediates (4) provides compounds (7). Hydrolysis under basic conditions provides the compounds with the general structure (8).

Scheme 6

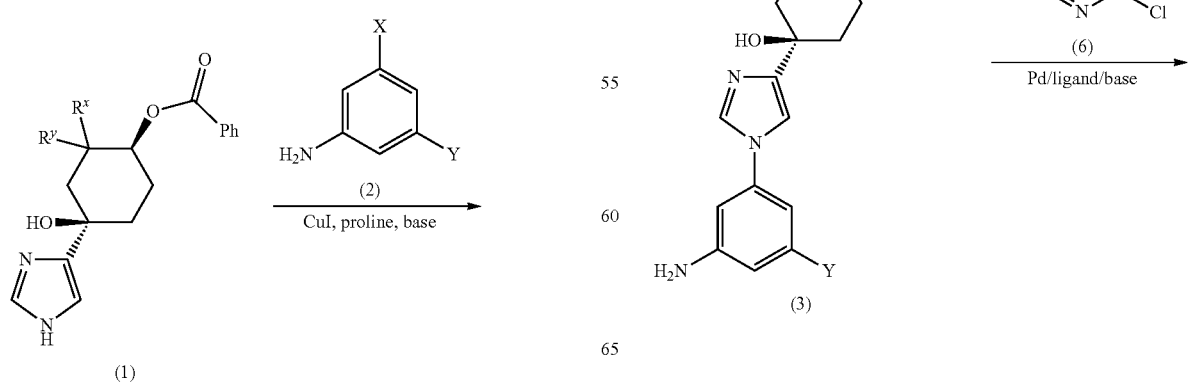

-continued

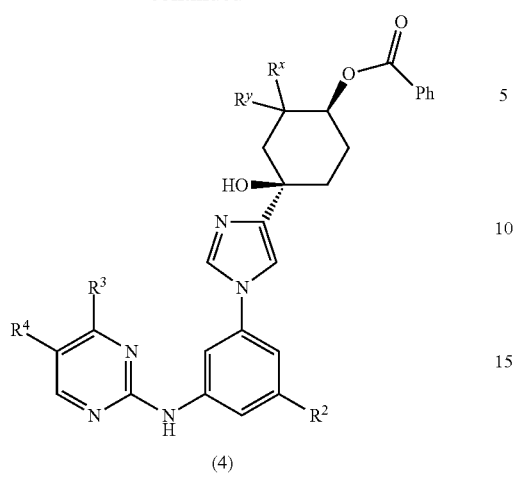

(4)

↓ NaOH or KOH

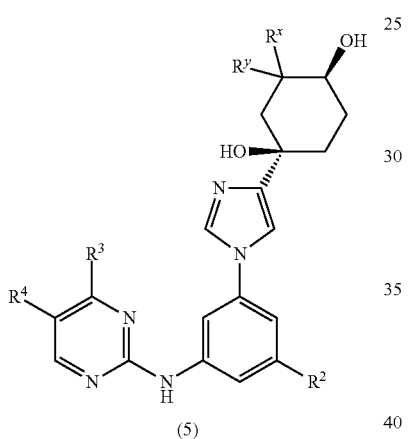

(5)

Intermediates (3) are prepared by copper coupling of compounds (1) with commercially available or prepared compounds (2). Buchwald coupling of intermediates (3) and commercially available or prepared compounds (6) provides compounds (4). Hydrolysis under basic conditions provides the compounds with the general structure (5).

Scheme 7

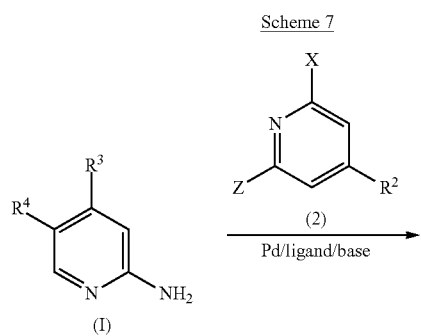

-continued

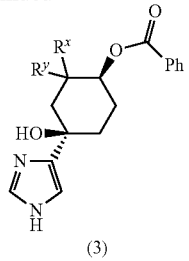

(3)

or

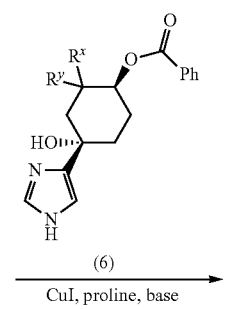

(6)

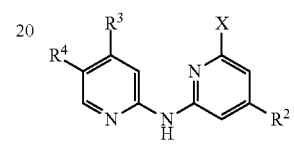

(2)

→ CuI, proline, base

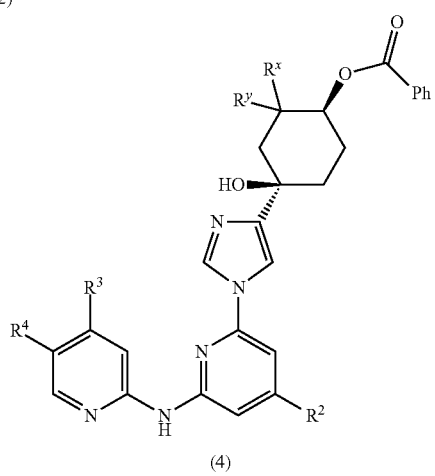

(4)

↓ NaOH or KOH

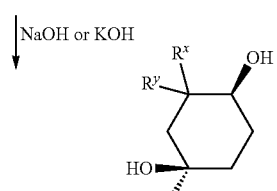

(5)

Compounds (2) are prepared utilizing 2-aminopyridines 1 and halopyridines (2) via Buchwald coupling. Compounds (4) are prepared from compounds (2) and imidazoles (3) or (6) under copper coupling conditions. Hydrolysis under basic conditions provides the compounds with the general structure (5).

Scheme 8

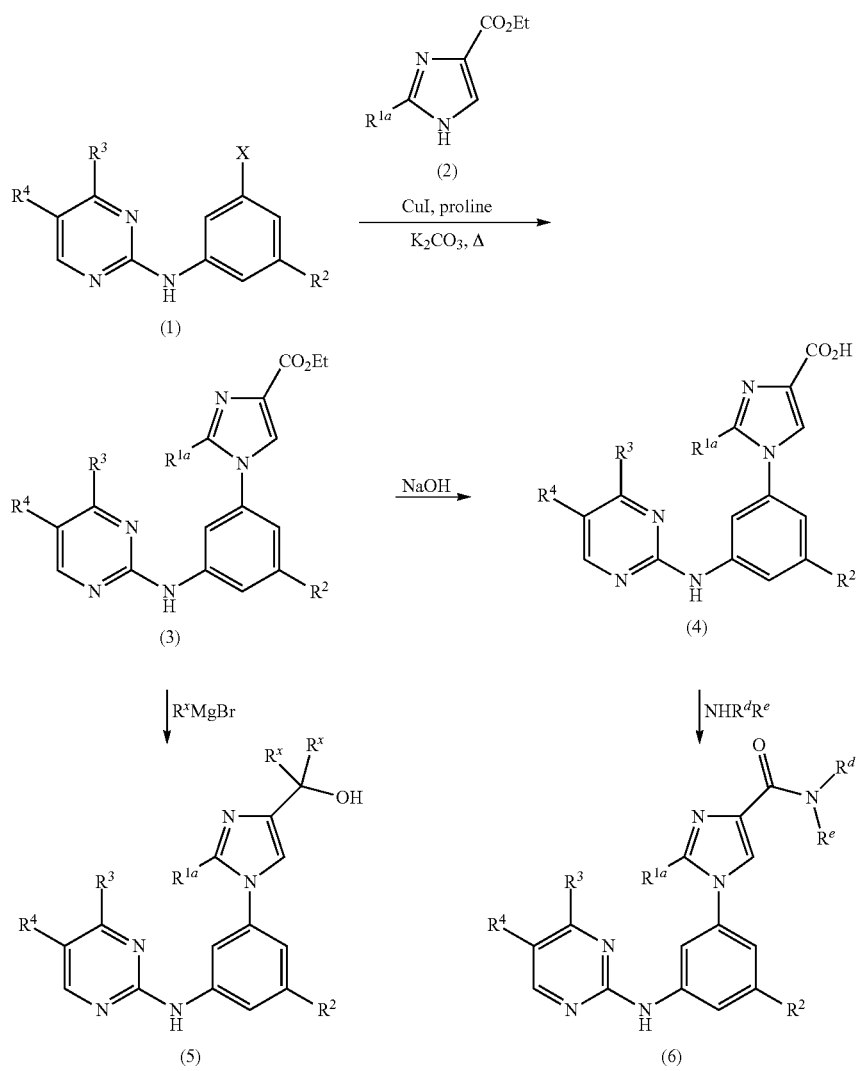

Compounds (3) are prepared by copper coupling of compounds 1 with commercially available or prepared imidazoles (2). Treatment of compounds (3) under basic conditions provides the compounds with the general structure (4). Reaction of compounds (3) with a Grignard reagent provides compounds (5). Amides (6) are formed by treatment of acids (4) and an amine with amide coupling reagents such as EDC and HOBt or HATU.

Scheme 9

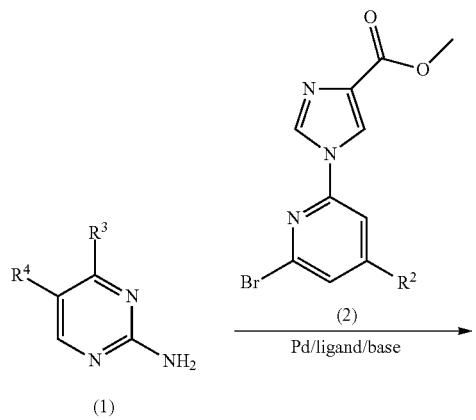

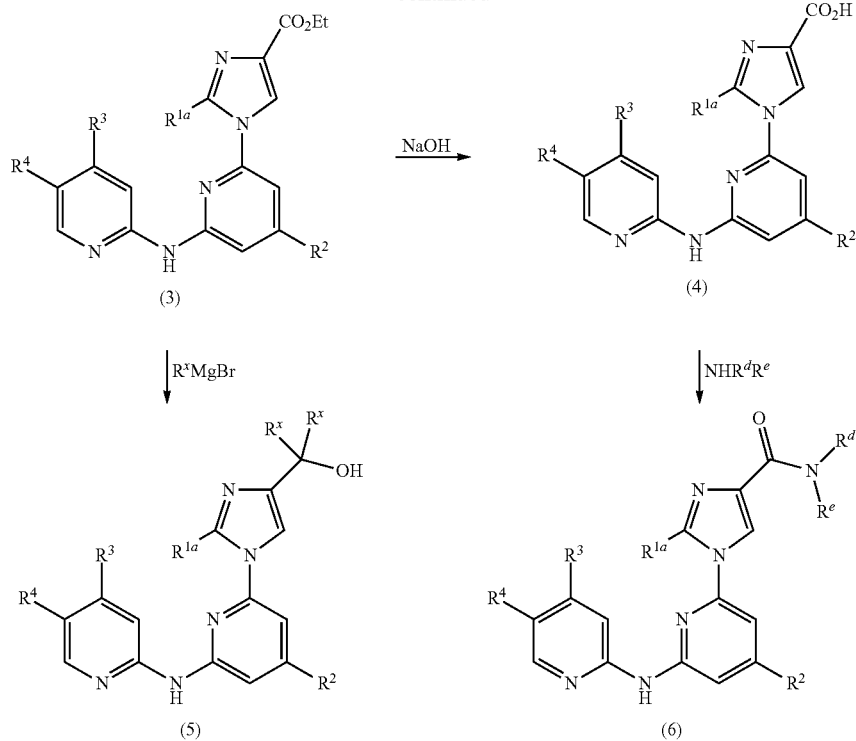

Compounds (3) are prepared by Buchwald coupling of compounds (1) with intermediates (2). Treatment of compounds (3) under basic conditions provides the compounds with the general structure (4). Reaction of compounds (3) with a Grignard reagent provides compounds (5). Amides (6) are formed by treatment of acids (4) and an amine with amide coupling reagents such as EDC and HOBt or HATU.

Scheme 10

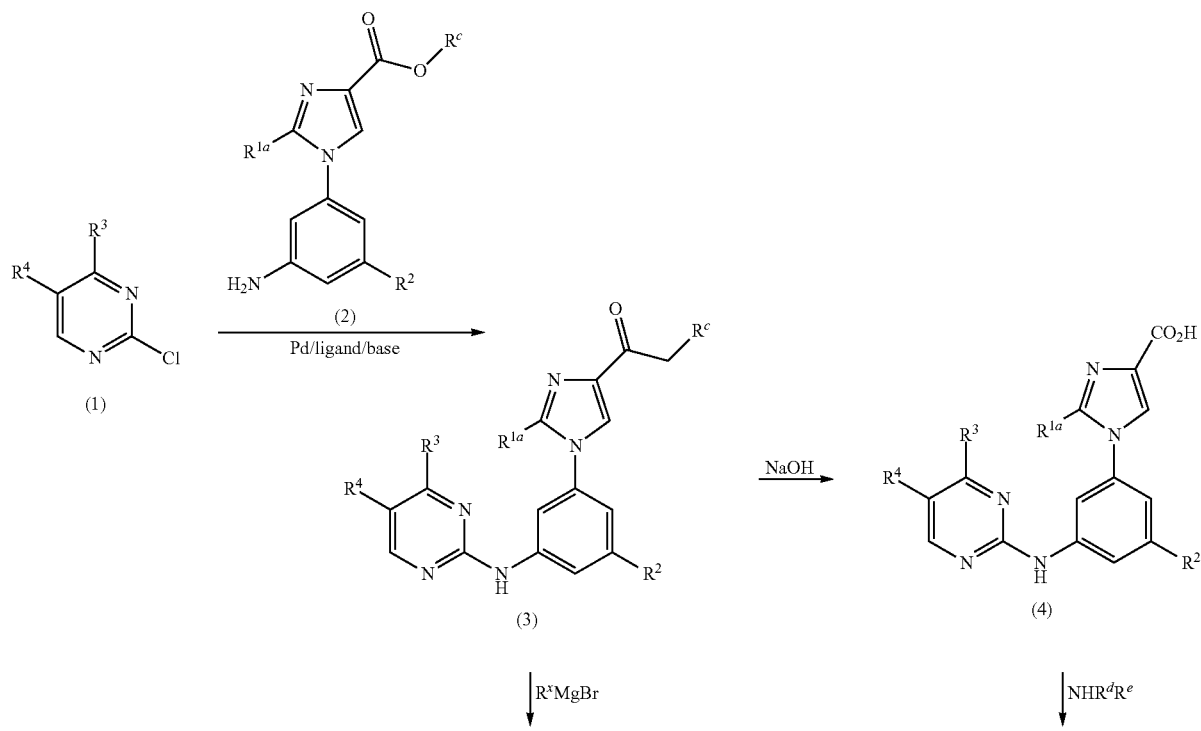

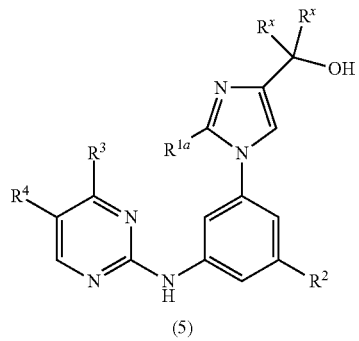

(5)

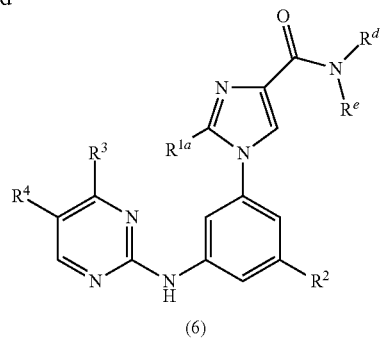

(6)

Compounds 3 are prepared by Buchwald coupling of compounds (1) with intermediates (2). Treatment of compounds (3) under basic conditions provides the compounds with the general structure (4). Reaction of compounds (3) with a Grignard reagent provides compounds (5). Amides (6) are formed by treatment of acids (4) and an amine with amide coupling reagents such as EDC and HOBt or HATU.

Scheme 11

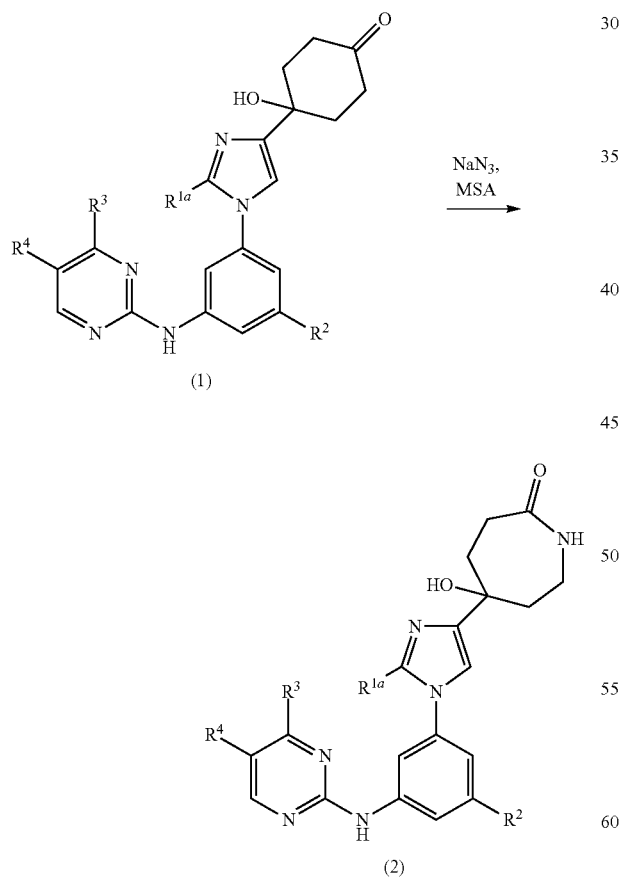

Treatment of compounds (1) with sodium azide and methanesulfonic acid provide compounds (2).

Scheme 12

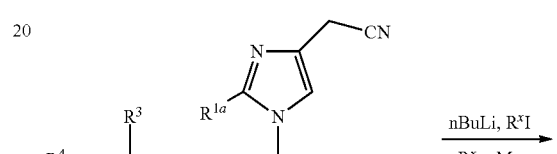

Treatment of compounds (1) with n-butyllithium and methyl iodide provides compounds (2). Hydrolysis of compound (2) under acidic conditions provides compounds (3).

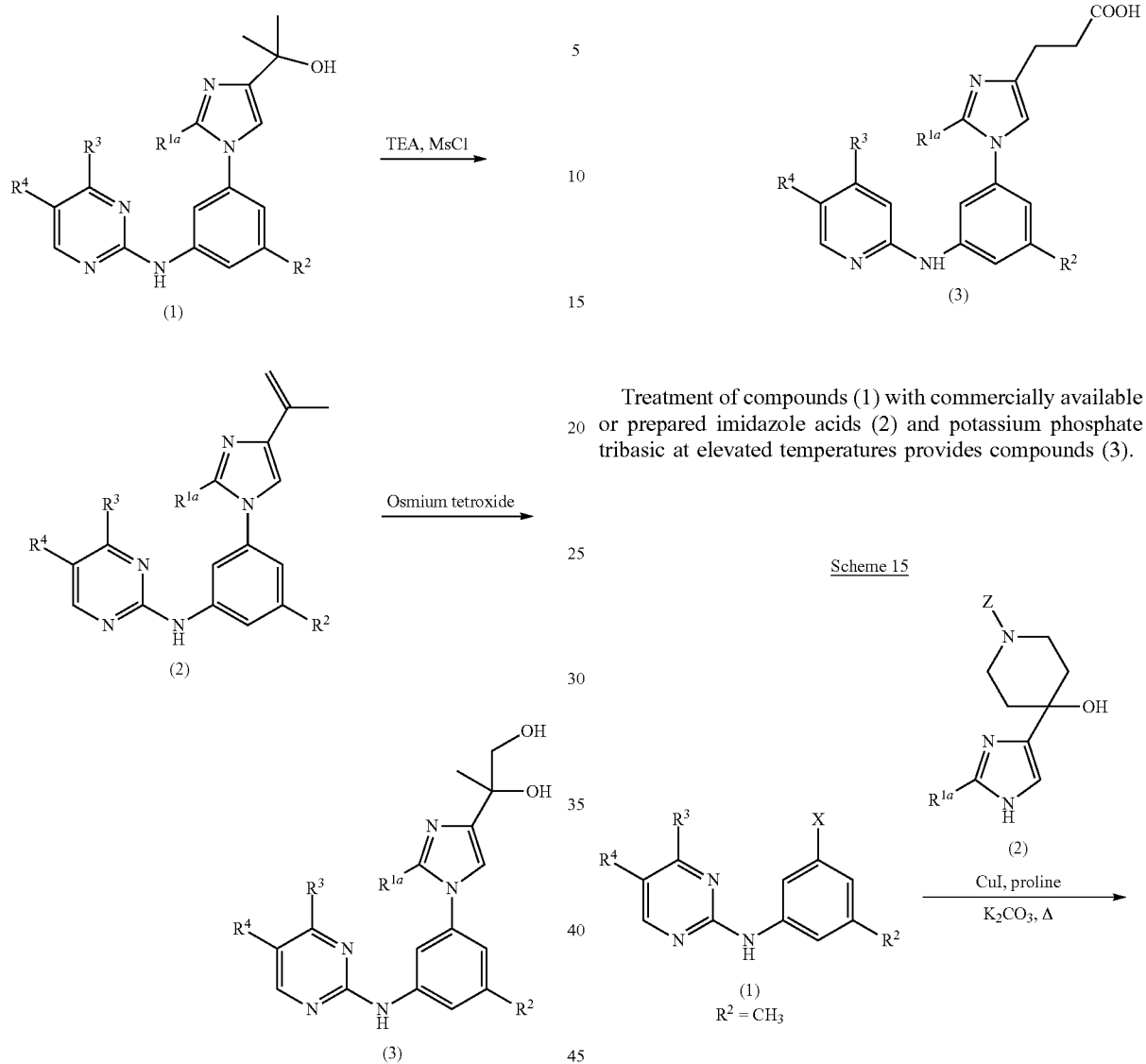
Treatment of compounds (1) with commercially available or prepared imidazole acids (2) and potassium phosphate tribasic at elevated temperatures provides compounds (3).
Treatment of compounds (1) with triethylamine and methanesulfonyl chloride provides compounds (2). Treatment of compounds (2) with N-methylmorpholine-N-oxide and osmium tetroxide provides compounds (3).
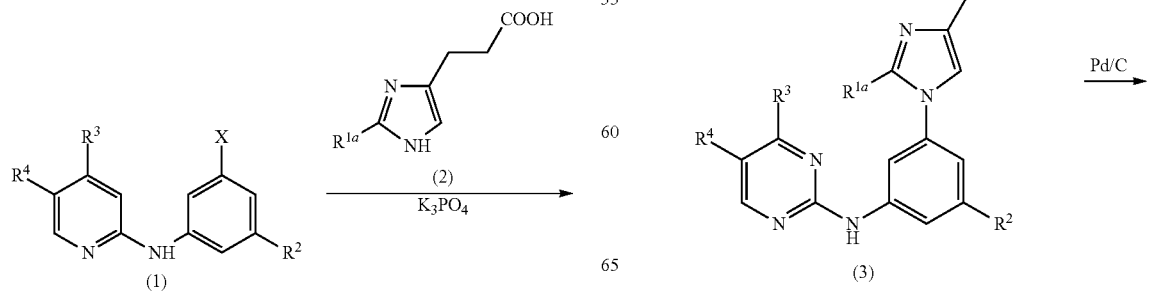

53
-continued
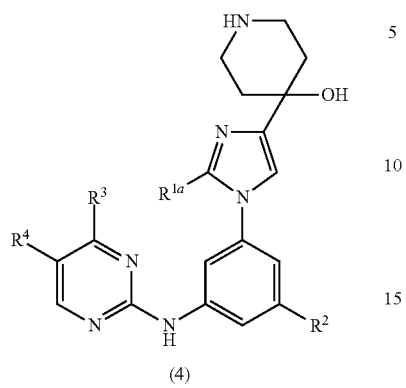
(4)
↓ KOCN, HCl
54
-continued
(5)
Intermediates (3) are prepared by copper coupling of compounds (1) with commercially available or prepared compounds (2). Deprotection of intermediates (3) provides compounds (4). Treatment of compounds (4) with potassium cyanate and acid provides the compounds with the general structure (5).
Scheme 16
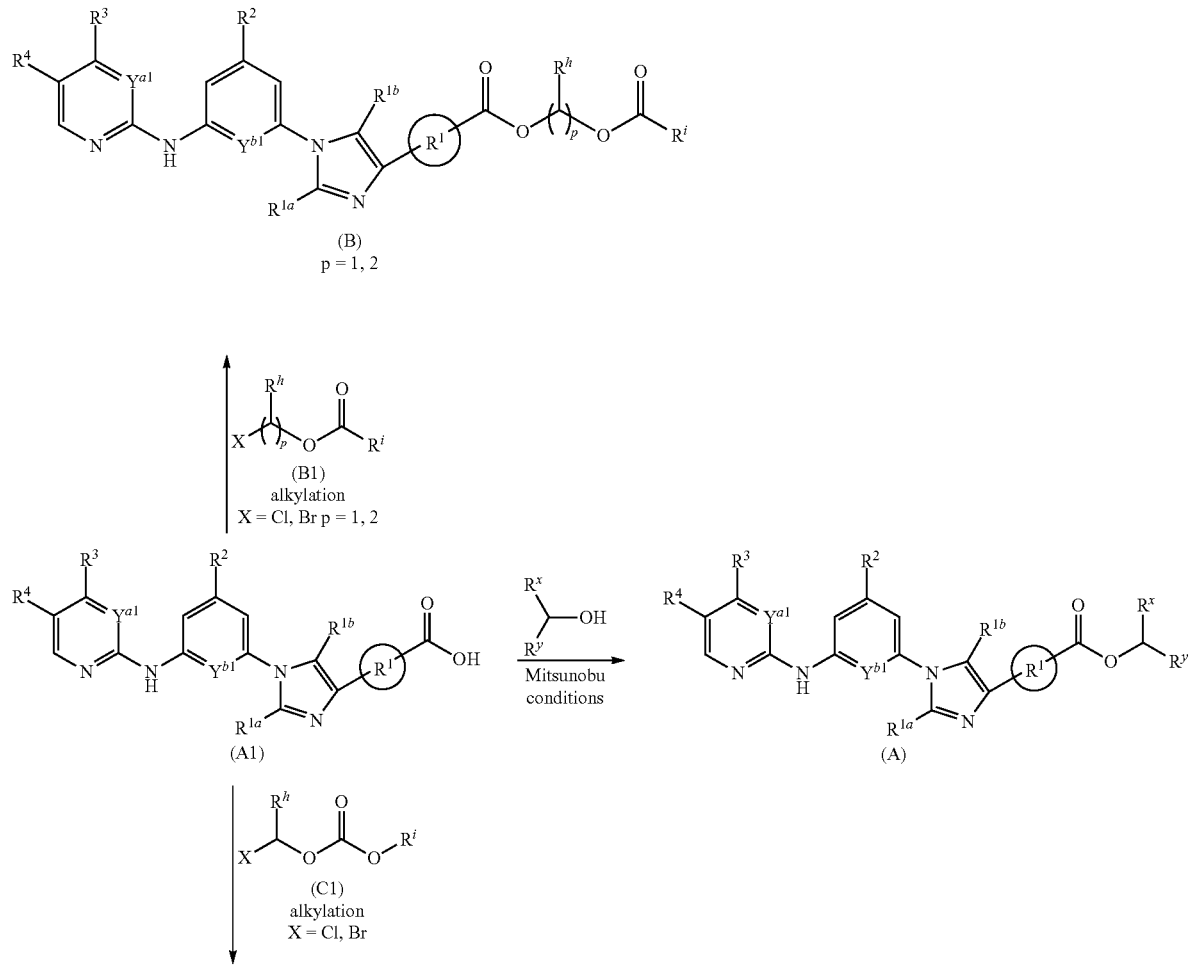

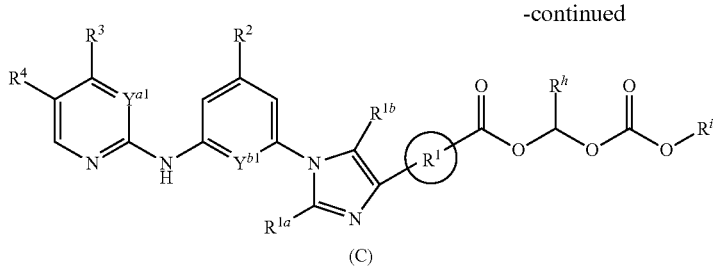

(C)

As shown in Scheme 16, compounds of structural subtype (A) are prepared from compounds of structural type (A1) (where substituent $R^1$ contains a carboxylic acid) by a Mitsunobu reaction with various primary and secondary alcohols, $R^xR^yCHOH$. Compounds of structural subtype (B) are prepared by the alkylation of compounds of structural type (A1) (where $R^1$ contains a carboxylic acid) by alkyl halides of formula (B1). Compounds of structural subtype (C) are prepared by the alkylation of compounds of structural type (A1) (where $R^1$ contains a carboxylic acid) by alkyl halides of formula (C1).

Scheme 17

(A1)

(D)

As shown in Scheme 17, compounds of structural subtype (D) are prepared by the reaction of the carboxylic acid (A1) with trimethylsilyldiazomethane and methanol.

Compounds of Formula I can be prepared according to the procedures described in the Schemes and Examples herein, using appropriate materials and are further exemplified by the following specific examples. The compounds exemplified are illustrative of the invention and are not, however, to be construed as limiting the scope of the invention in any manner. The examples further illustrate details for the preparation of the compounds of the present invention. Those skilled in the art will readily understand that known variations of protecting groups, of reagents, as well as of the conditions and processes of the following preparative procedures, can be used to prepare these compounds. It is also understood that whenever a chemical reagent is not commercially available, such a chemical reagent can be readily prepared by those skilled in the art by either following or adapting known methods described in the literature. All temperatures are degrees Celsius unless otherwise noted. Mass spectra (MS) were measured either by electrospray ion-mass spectroscopy (ESI) or by atmospheric pressure chemical ionization mass spectroscopy (APCI).

Intermediate 1

Dicyclopropyl(1H-imidazol-4-yl)methanol

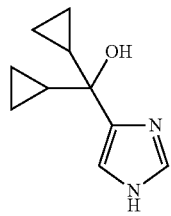 [SMILES: OC(c1c[nH]cn1)(C1CC1)C1CC1]

A suspension of methyl 1H-imidazole-4-carboxylate (1.0 g, 7.93 mmol) in THF (10 mL) was charged with cyclopropyl magnesium bromide (0.5 M in tetrahydrofuran, 49.2 ml, 24.58 mmol) and then heated to reflux for 30 minutes. The reaction mixture was cooled to room temperature, sonicated for 1 hour, and heated to reflux for another hour. The reaction mixture was allowed to cool to room temperature and concentrated under reduced pressure to a volume of approximately 15 mL. The reaction mixture was poured into saturated aqueous sodium bicarbonate (50 mL), and extracted with 10% isopropanol/chloroform (3×, 70 mL, 50 mL, 20 mL). The combined organic extracts were washed with brine, dried over sodium sulfate, filtered, and concentrated under reduced pressure. The residue was purified by chromatography on silica gel (5-20% methanol/dichloromethane) to give dicyclopropyl(1H-imidazol-4-yl)methanol. MS ESI calc. For $C_{10}H_{15}N_2O$ [M+H]+ 179. found 179. $^1H$ NMR (500 MHz, DMSO-$d_6$) (* denotes major tautomer): δ 11.72 (s, 1H), 11.67 (s, 1H)*, 7.46 (s, 1H)*, 7.42 (s, 1H), 6.85 (s, 1H)*, 6.73 (s, 1H), 4.47 (s, 1H)*, 3.95 (s, 1H), 1.23 (s, 2H)*, 1.13 (s, 2H), 0.18-0.02 (m, 4H)*, 0.18-0.02 (m, 4H).

Intermediate 2

Ethyl 2-methyl-2-(4-oxocyclohexyl)propanoate

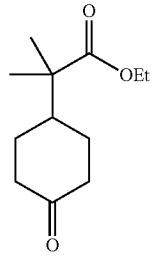

Step 1:

A solution of ethyl 1,4-dioxaspiro[4.5]dec-8-ylacetate (3.07 g, 13.45 mmol) in tetrahydrofuran (10 mL) was added via syringe to a solution of lithium diisopropylamide (1.8 M in tetrahydrofuran/heptane/ethylbenzene, 11.95 ml, 21.52 mmol) in tetrahydrofuran (15 mL) at −78° C. After 30 minutes, methyl iodide (1.093 ml, 17.48 mmol) was added over 1 minute. The reaction mixture was allowed to warm for 30 minutes, then placed in a 0° C. bath for 30 minutes, and finally moved to a −78° C. bath. Lithium diisopropylamide (1.8 M in tetrahydrofuran/heptane/ethylbenzene, 11.95 ml, 21.52 mmol) was added over 15 minutes, and after an additional 15 minutes methyl iodide (1.430 ml, 22.86 mmol) was added. Following 25 minutes in a −78° C. bath, the reaction mixture was allowed to warm for 15 minutes and then placed in a 0° C. bath. After 70 minutes, the reaction mixture was moved to a room temperature bath and after 30 minutes everything had dissolved. The reaction mixture was then diluted with ethyl acetate (50 mL) and saturated aqueous ammonium chloride (25 mL). The layers were separated and the organic layer was washed with saturated aqueous sodium bicarbonate and brine, dried over sodium sulfate, filtered, and concentrated under reduced pressure. The residue was purified by chromatography on silica gel (5-30% ethyl acetate/hexanes) to provide ethyl 1,4-dioxaspiro[4.5]dec-8-ylacetate. $^1$H NMR (500 MHz, CDCl$_3$) δ 4.12 (q, J=7.1 Hz, 2H), 3.93 (m, 3H), 1.82-1.75 (m, 2H), 1.71-1.60 (m, 1H), 1.60-1.48 (m, 5H), 1.38-1.31 (m, 2H), 1.24 (t, J=7.1 Hz, 3H), 1.11 (s, 6H).

Step 2:

A solution of ethyl 1,4-dioxaspiro[4.5]dec-8-ylacetate (1.236 g, 4.82 mmol) and aqueous hydrochloric acid (1M, 20 ml, 20.00 mmol) in acetone (60 mL) was refluxed for 9 hours. Upon cooling, the layers were separated and the aqueous layer was extracted with ethyl acetate (2×25 mL). The combined organic layers were washed with saturated aqueous sodium bicarbonate (20 mL) and brine (20 mL), dried over magnesium sulfate, filtered, and concentrated under reduced pressure to afford ethyl 2-methyl-2-(4-oxocyclohexyl)propanoate which was used without further purification. $^1$H NMR (500 MHz, CDCl$_3$) δ 4.15 (q, J=7.1 Hz, 2H), 2.45-2.39 (m, 2H), 2.39-2.29 (m, 2H), 2.14-2.06 (m, 1H), 1.97-1.89 (m, 2H), 1.54-1.46 (m, 2H), 1.27 (t, J=7.1 Hz, 3H), 1.16 (s, 6H).

Intermediate 3

6-Bromo-4-methyl-N-[4-(trifluoromethyl)pyridine-2-yl]pyridine-2-amine

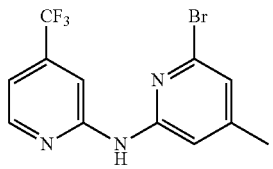 [SMILES: Cc1cc(Br)nc(Nc2cc(C(F)(F)F)ccn2)c1]

To a flask containing 2,6-dibromo-4-methylpyridine (13.9 g, 55.5 mmol) and 2-amino-4-trifluoromethylpyridine (9.0 g, 55.5 mmol) was added nitrogen sparged dioxane (180 mL). Sodium tert-butoxide (5.87 g, 61.1 mmol) and 1,1'-bis (di-tert-butylphosphino)ferrocene palladium dichloride (0.905 g, 1.4 mmol) were then added, and the slurry was evacuated and refilled with nitrogen. The mixture was stirred at 25° C. for 15 minutes and then heated to 75° C. for 12 hours. The reaction was cooled to 25° C., water (20 mL) was added, and the mixture was extracted with ethyl acetate (2×200 mL). The combined extracts were dried over Na$_2$SO$_4$, filtered, concentrated in vacuo. The residue was purified via chromatography on silica gel to afford 6-bromo-4-methyl-N-[4-(trifluoromethyl)pyridine-2-yl]pyridine-2-amine as a white solid. MS ESI calc'd. for C$_{12}$H$_{10}$BrF$_3$N$_3$ [M+H]$^+$ 332 and 334. found 332 and 334. $^1$H NMR (600 MHz, DMSO-d$_6$) δ 10.40 (s, 1H), 8.46 (d, J=6.0 Hz, 1H), 7.90 (s, 1H), 7.60 (s, 1H), 7.18 (d, J=6.0 Hz, 1H), 7.00 (s, 1H), 2.25 (s, 3H).

The intermediates in the following Table were prepared according to the method described for intermediate 3

| Intermediate | Structure | Chemical Name | Exact Mass [M + H]$^+$ |
| --- | --- | --- | --- |
| 4 | ![structure] | N-(6-bromo-4-methyl-pyridin-2-yl)-5-fluoro-4-methylpyridin-2-amine | Calc'd 296, 298 Found 296, 298 |
| 5 | ![structure] | N-(6-bromo-4-methyl-pyridin-2-yl)-5-chloro-4-methylpyridin-2-amine | Calc'd 314, Found 314 |
| 6 | ![structure] | 6-bromo-N-(4-cyclopropyl-pyridin-2-yl)-4-methyl-pyridin-2-amine | Calc'd 304, −306 found 304, −306 |

-continued

| Intermediate | Structure | Chemical Name | Exact Mass [M + H]+ |
|---|---|---|---|
| 7 | 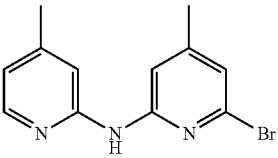 [SMILES: Cc1ccnc(Nc2cc(C)cc(Br)n2)c1] | 6-bromo-4-methyl-N-(4-methylpyridin-2-yl)pyridin-2-amine | Calc'd 278, 280 found 278, 280 |
| 8 | 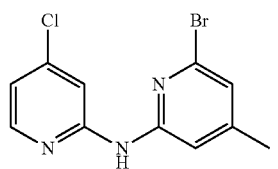 [SMILES: Cc1cc(Br)nc(Nc2cc(Cl)ccn2)c1] | 6-bromo-N-(4-chloropyridin-2-yl)-4-methylpyridin-2-amine | Calc'd 300 found 300 |
| 9 | 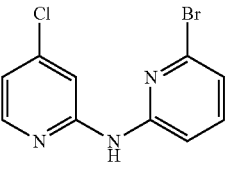 [SMILES: Clc1ccnc(Nc2cccc(Br)n2)c1] | N-(6-bromopyridin-2-yl)-4-chloropyridin-2-amine | Calc'd 286 found 286 |
| 10 | 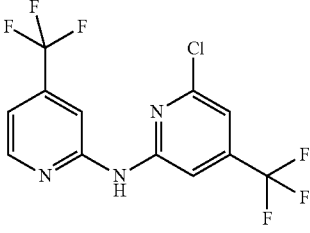 [SMILES: FC(F)(F)c1ccnc(Nc2cc(C(F)(F)F)cc(Cl)n2)c1] | 6-chloro-4-(trifluoromethyl)-N-[4-(trifluoromethyl)pyridin-2-yl]pyridin-2-amine | Calc'd 342 found 342 |
| 11 | 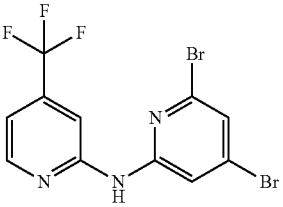 | 4,6-dibromo-N-[4-(trifluoromethyl)pyridin-2-yl]pyridin-2-amine | Calc'd 398 found 398 |
| 12 | 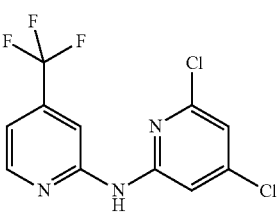 [SMILES: FC(F)(F)c1ccnc(Nc2cc(Cl)cc(Cl)n2)c1] | 4,6-dichloro-N-[4-(trifluoromethyl)pyridin-2-yl]pyridin-2-amine | Calc'd 308 found 308 |
| 13 | 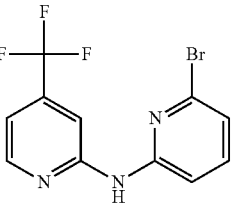 | N-(6-bromopyridin-2-yl)-4-(trifluoromethyl)pyridin-2-amine | Calc'd 318, 320 found 318, 320 |

| Intermediate | Structure | Chemical Name | Exact Mass [M + H]+ |
|---|---|---|---|
| 14 | 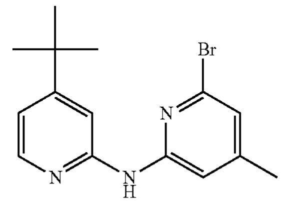 [SMILES: Cc1cc(Br)nc(Nc2cc(C(C)(C)C)ccn2)c1] | 6-bromo-N-(4-tert-butylpiperidin-2-yl)-4-methylpyridin-2-amine | Calc'd 320, 322 found 320, 322 |
| 15 | 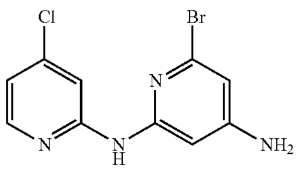 [SMILES: Nc1cc(Br)nc(Nc2cc(Cl)ccn2)c1] | 6-bromo-N~2~-(4-chloropyridin-2-yl)pyridine-2,4-diamine | Calc'd 301, found 301 |
| 16 | 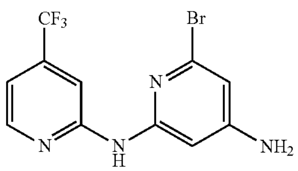 | 6-bromo-N~2~-[4-(trifluoromethyl)pyridin-2-yl]pyridine-2,4-diamine | Calc'd 333, 335 found 333, 335 |
| 17 | 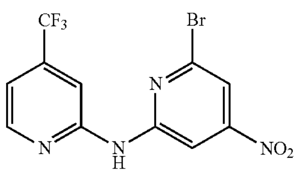 [SMILES: O=[N+]([O-])c1cc(Br)nc(Nc2cc(C(F)(F)F)ccn2)c1] | 6-bromo-4-nitro-N-[4-(trifluoromethyl)pyridin-2-yl]pyridin-2-amine | Calc'd 363, 365 found 363, 365 |

Intermediate 18

N-(3-iodo-5-methylphenyl)-4-(trifluoromethyl)pyrimidin-2-amine

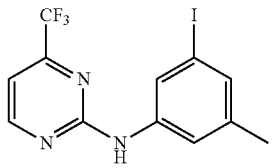 [SMILES: Cc1cc(I)cc(Nc2nccc(C(F)(F)F)n2)c1]

Step 1:

A solution of 3-bromo-5-methylaniline (162.5 g, 873.66 mmol) in 1,4-dioxane (2 L) was prepared, and 2-chloro-4-(trifluoromethyl)pyrimidine (182 g, 994.54 mmol) and methanesulfonic acid (97.5 g, 1.02 mol) were added sequentially. The resulting solution was heated to reflux overnight. The resulting mixture was cooled and concentrated in vacuo. The residue was diluted with water (2 L), adjusted to a pH 7-8 with aqueous sodium bicarbonate solution and product extracted with EtOAc (2×2 L). The organic layers were combined, washed with water (2×2 L), dried over anhydrous sodium sulfate and concentrated in vacuo. This resulted in N-(3-bromo-5-methylphenyl)-4-(trifluoromethyl)pyrimidin-2-amine (200 g, 602 mmol, 69%) as a light yellow solid. MS ESI calcd. For $C_{12}H_{10}BrF_3N_3$ [M+H]+ 332, 334.0. found 332, 334. $^1$H NMR (500 MHz, CDCl$_3$): δ 8.68 (d, J=4.9 Hz, 1H); 7.79 (s, 1H); 7.30 (s, 2H); 7.10-7.06 (m, 2H); 2.36 (s, 3H).

Step 2:

To a mixture of N-(3-bromo-5-methylphenyl)-4-(trifluoromethyl)pyrimidin-2-amine (0.6 g, 1.81 mmol), copper iodide (34.4 mg, 0.181 mmole), and sodium iodide (542 mg, 3.61 mmole) in a microwave vial under argon was added pentan-1-ol (1.8 mL) and dimethylethylenediamine (39.0 uL, 0.361 mmole). The vial was sealed and heated in a microwave at 180° C. for 90 minutes followed by additional heating at 120° C. in an oil bath for 24 hr. The reaction was cooled quenched with 30% aqueous ammonium hydroxide and water and the product extracted with dichloromethane (3×20 mL). The organic extracts were dried over sodium sulfate, filtered, concentrated to an oil and residue purified by silica gel chromatography (0-30% ethyl acetate/hexanes) to afford N-(3-iodo-5-methylphenyl)-4-(trifluoromethyl)pyrimidin 2-amine. MS ESI calcd. For $C_{12}H_{10}F_3IN_3$ [M+H]+ 380. found 380. $^1$H NMR (500 MHz, CDCl$_3$): δ 8.64 (d, J=4.9 Hz, 1H); 7.85 (s, 1H); 7.5-7.2 (m, 3H), 7.04 (d, J=4.9 Hz, 1H); 2.36 (s, 3H).

The intermediates in the following Table were prepared according to the method described for intermediate 18:

| Intermediate | Structure | Chemical Name | Exact Mass [M + H]+ |
|---|---|---|---|
| 19 | 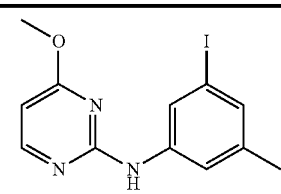 | N-(3-iodo-5-methylphenyl)-4-methoxy-pyrimidin-2-amine | Calc'd 342.0 found 342 |

-continued

| Intermediate | Structure | Chemical Name | Exact Mass [M + H]⁺ |
|---|---|---|---|
| 20 | 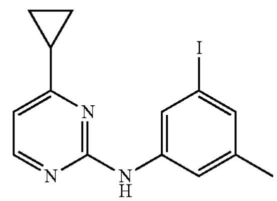 [SMILES: Cc1cc(I)cc(Nc2nccc(C3CC3)n2)c1] | 4-cyclopropyl-N-(3-iodo-5-methylphenyl)pyrimidin-2-amine | Calc'd 352 found 352 |
| 21 | 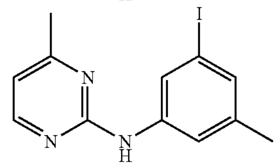 [SMILES: Cc1cc(I)cc(Nc2nccc(C)n2)c1] | N-(3-iodo-5-methylphenyl)-4-methylpyrimidin-2-amine | Calc'd 326 found 326 |
| 22 | 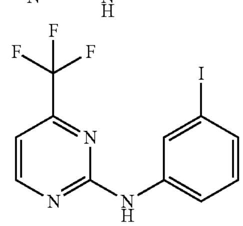 | N-(3-iodophenyl)-4-(trifluoromethyl)pyrimidin-2-amine | Calc'd 366 found 366 |

Intermediate 23

Methyl 1-[3-amino-5-(morpholin-4-yl)phenyl]-1H-imidazole-4-carboxylate

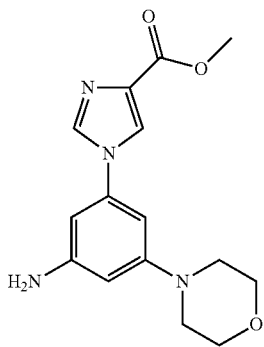 [SMILES: COC(=O)c1cn(-c2cc(N)cc(N3CCOCC3)c2)cn1]

Step 1:

To a mixture of 4-(3-iodo-5-nitrophenyl)morpholine (200 mg, 0.60 mmole), methyl 1H-imidazole-4-carboxylate (91 mg, 0.718 mmole), copper (I) oxide (4.28 mg, 0.030 mmole), $Cs_2CO_3$ (273 mg, 0.838 mmole) and 4,7-dimethoxy-1,10-phenanthroline (28.8 mg, 0.120 mmole) was added butyronitrile (0.5 mL). The mixture was heated to 110° C. for 18 hr. The mixture was cooled to room temperature, diluted with $CH_2Cl_2$ (50 mL) and filtered through CELITE. The CELITE cake was washed with $CH_2Cl_2$ (5 mL). The CELITE cake was suspended in THF (30 mL) and stirred for 15 minutes. The mixture was filtered and solids washed with THF (10 mL). The filtrate was concentrated in vacuo to afford crude methyl 1-[3-(morpholin-4-yl)-5-nitrophenyl]-1H-imidazole-4-carboxylate.

$^1$H NMR (500 MHz, $CDCl_3$): δ 8.05 (s, 1H); 7.92 (s, 1H); 7.78 (s, 1H); 7.70 (s, 1H); 6.98 (s, 1H); 3.95 (s, 3H); 3.90 (m, 4H), 3.35 (m, 4H).

Step 2:

To a solution of methyl 1-[3-(morpholin-4-yl)-5-nitrophenyl]-1H-imidazole-4-carboxylate (112 mg, 0.337 mmole) in DMF was added $SnCl_2(H_2O)_2$ (380 mg, 1.65 mmole). The mixture was stirred 18 hr at room temperature. The mixture was diluted with EtOAc (100 mL) and washed with sat. $NaHCO_3$ (100 mL) and then brine (3×100 mL). The organic extract was dried over sodium sulfate, filtered and concentrated in vacuo to an oil. Purification by chromatography on silica gel (12 g, 100:0 to 90:10 EtOAc:MeOH) afforded methyl 1-[3-amino-5-(morpholin-4-yl)phenyl]-1H-imidazole-4-carboxylate. $^1$H NMR (500 MHz, $CDCl_3$): δ 7.92 (s, 1H); 7.80 (s, 1H); 6.28 (s, 1H); 6.22 (m, 2H); 3.92 (s, 3H); 3.88 (s, 2H); 3.85 (m, 4H), 3.18 (m, 4H).

The intermediates in the following Table were prepared according to the method described for intermediate 23:

| Intermediate | Structure | Chemical Name | $^1$H NMR |
|---|---|---|---|
| 24 | 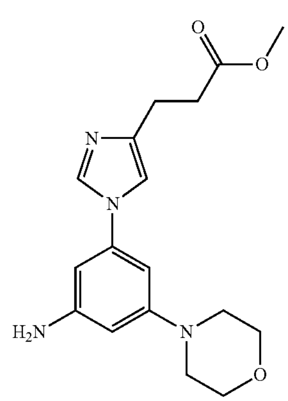 [SMILES: COC(=O)CCc1cn(-c2cc(N)cc(N3CCOCC3)c2)cn1] | Methyl 3-{1-[3-amino-5-(morpholin-4-yl)phenyl]-1H-imidazol-4-yl}propanoate | $^1$H NMR (500 MHz, $CDCl_3$): δ 7.71 (s, 1H); 7.00 (s, 1H); 6.25 (s, 1H); 6.18 (m, 2H); 3.85 (m, 6H); 3.68 (s, 3H); 3.18 (m, 4H); 2.95 (m, 2H); 2.72 (m, 2H). |

| Intermediate | Structure | Chemical Name | ¹H NMR |
|---|---|---|---|
| 25 | 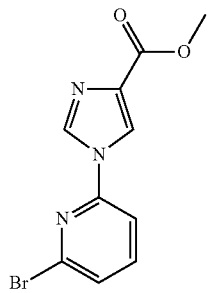 [SMILES: COC(=O)c1cn(-c2cccc(Br)n2)cn1] | Methyl 1-(6-bromopyridin-2-yl)-1H-imidazole-4-carboxylate | ¹H NMR (500 MHz, DMSO-d₆): δ 8.63 (m, 2H); 8.01 (m, 2H); 7.75 (m, 1H); 3.84 (s, 3H). |
| 26 | 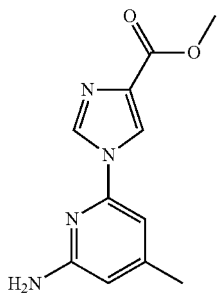 [SMILES: COC(=O)c1cn(-c2cc(C)cc(N)n2)cn1] | Methyl 1-(3-amino-5-methylphenyl)-1H-imidazole-4-carboxylate | ¹H NMR (500 MHz, CDCl₃): δ 7.91 (s, 1H); 7.82 (s, 1H); 6.60 (s, 1H); 6.55 (s, 1H); 6.52 (s, 1H); 3.94 (m, 5H); 2.32 (s, 3H). |
| 27 | 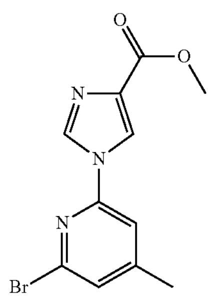 [SMILES: COC(=O)c1cn(-c2cc(C)cc(Br)n2)cn1] | 2-bromo-6-[4-(methoxymethyl)-1H-imidazol-1-yl]-4-methylpyridine | ¹H NMR (500 MHz, DMSO-d₆): δ 8.62 (m, 2H); 8.01 (m, 2 H); 7.82 (m, 1H); 3.95 (s, 3H). |

Intermediate 28

Ethyl cis-4-hydroxy-4-(1H-imidazol-4-yl)cyclohexanecarboxylate

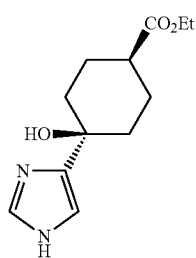 [SMILES: CCOC(=O)[C@H]1CC[C@](O)(c2c[nH]cn2)CC1]

Step 1:

4-Iodo-1-tritylimidazole (8.00 g, 18.34 mmol) was dissolved in CH₂Cl₂ (100 mL), and ethylmagnesium bromide (3.0 M in Et₂O, 6.72 mL, 20.17 mmol) was added at room temperature. After stirring for 30 min, ethyl 4-oxocyclohexanecarboxylate (3.75 g, 22.00 mmol) in CH₂Cl₂ (15 mL) was added. The reaction was stirred at room temperature for 18 h. The reaction was quenched with saturated NH₄Cl and extracted with CH₂Cl₂ (2×100 mL)). The combined organic layers were washed with brine, dried over MgSO₄, filtered and concentrated in vacuo to an oil. Purification by chromatography on silica (40-100% EtOAc/hexanes) afforded ethyl cis-4-hydroxy-4-(1-trityl-1H-imidazol-4-yl)cyclohexanecarboxylate as a white solid (crude ~60%, 4.28 g, higher R_f) and ethyl trans-4-hydroxy-4-(1-trityl-1H-imidazol-4-yl)cyclohexanecarboxylate as a white solid (2.71 g, lower R_f).

cis isomer: ¹H NMR (500 MHz, CDCl₃) δ 7.36 (m, 1H); 7.4-7.30 (m, 9H); 7.13 (m, 6H); 6.68 (m, 1H); 4.13 (q, J=7.0 Hz, 2H); 2.37 (s, 1H); 2.30 (m, 1H); 1.95 (m, 4H); 1.83 (m, 2H); 1.72 (m, 2H); 1.25 (t, J=7.0 Hz, 3H).

trans isomer: ¹H NMR (500 MHz, CDCl₃) δ 7.38 (m, 1H); 7.36-7.30 (m, 9H); 7.13 (m, 6H); 6.71 (m, 1H); 4.10 (q, J=7.0 Hz, 2H); 2.57 (s, 1H); 2.43 (m, 1H); 2.18 (m, 2H); 1.95 (m, 2H); 1.73 (m, 2H); 1.58 (m, 2H); 1.22 (t, J=7.0 Hz, 3H).

Step 2:

Ethyl cis-4-hydroxy-4-(1-trityl-1H-imidazol-4-yl)cyclohexanecarboxylate (4.27 g, 5.33 mmol, 60% pure) was dissolved in CH₂Cl₂ (40 mL) and TFA (10 mL) was added. The reaction was stirred at room temperature overnight. The reaction was diluted with toluene and concentrated. The residue was neutralized with saturated NaHCO₃ (30 mL) and extracted with 15% IPA/CHCl₃ (4×50 mL). The combined organic layers were dried over MgSO₄, filtered and concentrated. Purification by chromatography on silica (0-30% MeOH/CH$_2$Cl$_2$) afforded ethyl cis-4-hydroxy-4-(1H-imidazol-4-yl)cyclohexanecarboxylate (537 mg) as a white solid. MS ESI calcd. For C$_{12}$H$_{19}$N$_2$O$_3$ [M+H]$^+$ 239. found 239. $^1$H NMR (500 MHz, DMSO-d$_6$) δ 7.51 (dd, J=1.0 Hz, 1H); 6.79 (dd, J=0.7 Hz, 1H); 4.04 (q, J=7.1 Hz 2H); 3.32 (s, 1H); 2.25 (m, 1H); 1.80-1.60 (m, 8H); 1.16 (t, J=7.1 Hz, 3H).

Intermediate 29

Cis-4-hydroxy-4-(1H-imidazol-4-yl)cyclohexyl benzoate

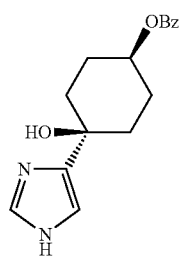

Step 1:
4-Hydroxy-cyclohexanone (2.00 g, 17.52 mmol) was dissolved in CH$_2$Cl$_2$ (40 mL). Pyridine (3.40 mL, 42.1 mmol) and benzoyl chloride (2.96 g, 21.03 mmol) were added, and the reaction was stirred at room temperature overnight. The reaction was diluted with water (100 mL) and extracted with CH$_2$Cl$_2$ (2×50 mL). The combined organic layers were washed with saturated CuSO$_4$, saturated NaHCO$_3$ and brine. The extracts were dried over MgSO$_4$, and concentrated. Purification by chromatography on silica (0-30% EtOAc/hexanes) afforded 4-oxocyclohexyl benzoate (3.80 g) as a colorless solid. MS ESI calcd. For C$_{13}$H$_{15}$O$_3$ [M+H]$^+$ 219. found 219.
Step 2:
4-Iodo-1-tritylimidazole (6.80 g, 15.59 mmol) was dissolved in CH$_2$Cl$_2$ (100 mL), and ethylmagnesium bromide (3.0 M in Et$_2$O, 5.71 mL, 17.14 mmol) was added at room temperature. After stirring for 30 min, 4-oxocyclohexyl benzoate (3.74 g, 17.14 mmol) in CH$_2$Cl$_2$ (10 mL) was added. The reaction was stirred at room temperature for 18 h., quenched with saturated NH$_4$Cl (100 mL) and extracted with CH$_2$Cl$_2$ (2×100 mL). The combined organic layers were washed with brine, dried over MgSO$_4$, filtered and concentrated. Purification by chromatography on silica (25-100% EtOAc/hexanes) afforded cis-4-hydroxy-4-(1-trityl-1H-imidazol-4-yl)cyclohexyl benzoate (4.46 g (77% pure) as a colorless solid (higher R$_f$) and trans-4-hydroxy-4-(1-trityl-1H-imidazol-4-yl)cyclohexyl benzoate (1.37 g) as a colorless solid (lower R$_f$).
cis isomer: $^1$H NMR (500 MHz, CDCl$_3$) δ 8.09-8.01 (m, 2H), 7.54 (t, J=7.4, 1H), 7.46-7.40 (m, 3H), 7.39-7.31 (m, 9H), 7.17-7.10 (m, 6H), 6.70 (d, J=1.3, 1H), 5.11-4.97 (m, 1H), 2.82 (s, 1H), 2.15-2.00 (m, 5H), 1.98-1.82 (m, 4H).
trans isomer: $^1$H NMR (500 MHz, CDCl$_3$) δ 8.03-7.98 (m, 2H), 7.58-7.52 (m, 1H), 7.48 (d, J=1.3, 1H), 7.42 (t, J=7.8, 2H), 7.39-7.32 (m, 9H), 7.18-7.10 (m, 6H), 6.74 (d, J=1.4, 1H), 5.27 (s, 1H), 2.77 (s, 1H), 2.20-2.07 (m, 4H), 1.96-1.74 (m, 4H).
Step 3:
cis-4-Hydroxy-4-(1-trityl-1H-imidazol-4-yl)cyclohexyl benzoate (77% pure, 2.397 g, 3.49 mmol) was dissolved in CH$_2$Cl$_2$ (20 ml), and Et$_3$SiH (5.0 mL, 31.3 mmol) and TFA (5 mL) were added. The reaction was stirred at room temperature overnight. The reaction was diluted with toluene and concentrated. The residue was neutralized with saturated NaHCO$_3$ and extracted with 15% IPA/CHCl$_3$ (4×40 mL). The combined organic layers were dried over MgSO$_4$, and concentrated. The crude residue was triturated with CH$_2$Cl$_2$, filtered, and dried to provide cis-4-hydroxy-4-(1H-imidazol-4-yl)cyclohexyl benzoate (847 mg) as a colorless solid. MS ESI calcd. For C$_{16}$H$_{19}$N$_2$O$_3$ [M+H]$^+$ 287. found 287. $^1$H NMR (500 MHz, D$_6$-DMSO) δ 7.96 (m, 2H); 7.64 (m, 1H); 7.52 (m, 3H); 6.85 (s, 1H); 4.91 (m, 1H); 4.77 (s, 1H); 3.32 (s, 1H); 1.86 (m, 8H).

The intermediates in the following Table were prepared according to the method described for intermediates 28 and 29.

| Intermediate | Structure | Chemical Name | Exact Mass [M + H]$^+$ |
|---|---|---|---|
| 30 | 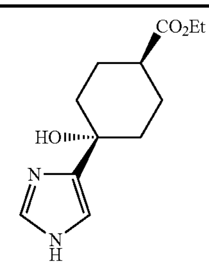 | Ethyl trans-4-hydroxy-4-(1H-imidazol-4-yl)-cyclohexanecarboxylate | Calc'd. 239 Found 239. |
| 31 | 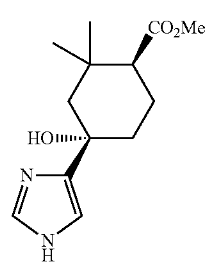 [SMILES: COC(=O)[C@H]1CC[C@@](O)(c2c[nH]cn2)CC1(C)C] | Methyl (1S,4S)-4-hydroxy-4-(1H-imidazol-4-yl)-2,2-dimethyl-cyclohexanecarboxylate | Calc'd. 253 Found 253. |

-continued

| Intermediate | Structure | Chemical Name | Exact Mass [M + H]+ |
|---|---|---|---|
| 32 | 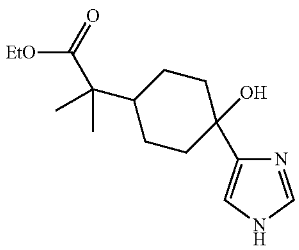 [SMILES: CCOC(=O)C(C)(C)C1CCC(O)(c2c[nH]cn2)CC1] | Ethyl 2-[4-hydroxy-4-(1H-imidazol-4-yl)cyclohexyl]-2-methylpropanoate | Calc'd. 281 Found 281. |
| 33 | 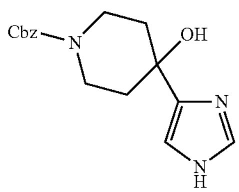 [SMILES: O=C(OCc1ccccc1)N1CCC(O)(c2c[nH]cn2)CC1] | Benzyl 4-hydroxy-4-(1H-imidazol-4-yl)piperidine-1-carboxylate | Calc'd. 302 Found 302. |
| 34 | 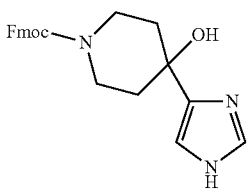 | (9H-fluoren-9-yl)methyl 4-hydroxy-4-(1H-imidazol-4-yl)piperidine-1-carboxylate | Calc'd. 390 found 390 |
| 35 | 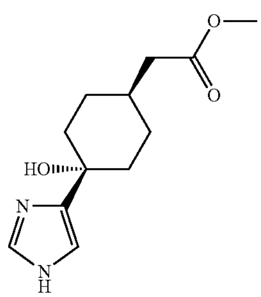 [SMILES: COC(=O)C[C@H]1CC[C@@](O)(c2c[nH]cn2)CC1] | Methyl [trans-4-hydroxy-4-(1H-imidazol-4-yl)cyclohexyl]acetate | Calc'd. 239 found 239 |
| 36 | 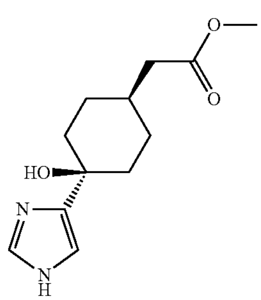 [SMILES: COC(=O)C[C@H]1CC[C@](O)(c2c[nH]cn2)CC1] | Methyl [cis-4-hydroxy-4-(1H-imidazol-4-yl)cyclohexyl]acetate | Calc'd. 239 found 239 |
| 37 | 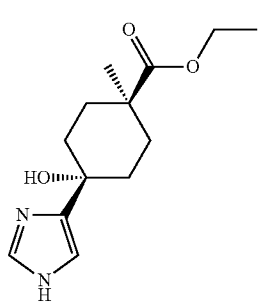 [SMILES: CCOC(=O)[C@]1(C)CC[C@](O)(c2c[nH]cn2)CC1] | Ethyl trans-4-hydroxy-4-(1H-imidazol-4-yl)-1-methylcyclohexane carboxylate | Calc'd. 253 found 253 |

-continued

| Intermediate | Structure | Chemical Name | Exact Mass [M + H]+ |
|---|---|---|---|
| 38 | 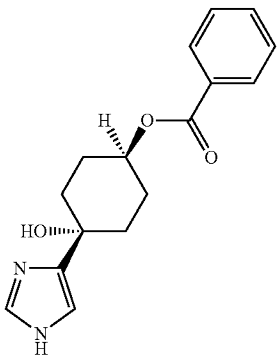 [SMILES: O=C(O[C@H]1CC[C@@](O)(c2c[nH]cn2)CC1)c1ccccc1] | trans-4-hydroxy-4-(1H-imidazol-4-yl)cyclohexyl benzoate | Calc'd. 287 found 287 |
| 39 | 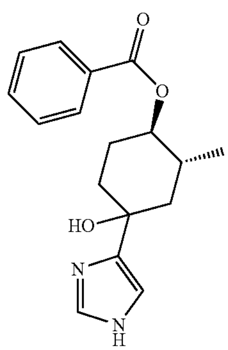 [SMILES: C[C@@H]1CC(O)(c2c[nH]cn2)CC[C@H]1OC(=O)c1ccccc1] | (1R,2R)-4-hydroxy-4-(1H-imidazol-4-yl)-2-methylcyclohexyl benzoate | Calc'd. 301 found 301 |
| 40 | 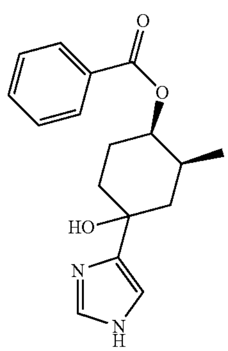 [SMILES: C[C@H]1CC(O)(c2c[nH]cn2)CC[C@H]1OC(=O)c1ccccc1] | (1R,2S)-4-hydroxy-4-(1H-imidazol-4-yl)-2-methylcyclohexyl benzoate | Calc'd. 301 found 301 |
| 41 | 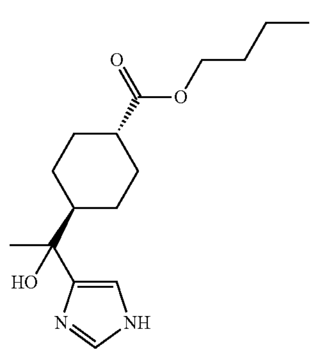 [SMILES: CCCCOC(=O)[C@H]1CC[C@H](C(C)(O)c2c[nH]cn2)CC1] | trans-butyl 4-(1-hydroxy-1-(1H-imidazol-4-yl)ethyl)cyclohexanecarboxylate | Calc'd. 295 found 295 |

Example 1

Cis-4-hydroxy-N-methyl-4-[1-(3-methyl-5-{[4-(trifluoromethyl)pyrimidin-2-yl]amino}phenyl)-1H-imidazol-4-yl]cyclohexanecarboxamide

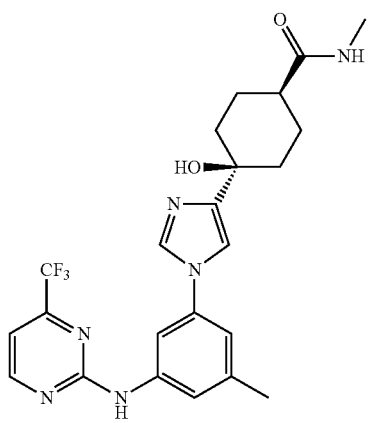 [SMILES: CNC(=O)[C@H]1CC[C@](O)(c2cn(-c3cc(C)cc(Nc4nccc(C(F)(F)F)n4)c3)cn2)CC1]

Step 1:

A vial was charged with N-(3-iodo-5-methylphenyl)-4-(trifluoromethyl)pyrimidin-2-amine (636 mg, 1.679 mmol), ethyl cis-4-hydroxy-4-(1H-imidazol-4-yl)cyclohexanecarboxylate (400 mg, 1.679 mmol), CuI (96 mg, 0.504 mmol), $K_2CO_3$ (464 mg, 3.36 mmol), and proline (116 mg, 1.007 mmol), sealed, and purged with nitrogen (3×). DMSO (8 mL) was added, and the reaction was stirred at 120° C. in an oil bath for 3 h. The reaction was cooled to room temperature, diluted with water, and extracted with EtOAc (2×). The combined organic layers were washed with brine, dried ($MgSO_4$), and evaporated. Flash chromatography (dry load, 40-100% EtOAc/hexanes) afforded ethyl cis-4-hydroxy-4-[1-(3-methyl-5-{[4-(trifluoromethyl)pyrimidin-2-yl]amino}phenyl)-1H-imidazol-4-yl]cyclohexanecarboxylate (450 mg, 55%) as a white solid. MS ESI calc. for $C_{24}H_{27}F_3N_5O_3$ [M+H]$^+$ 490. found 490. $^1$H NMR (500 MHz, DMSO-$d_6$) δ 10.34 (s, 1H), 8.84 (d, J=4.9, 1H), 8.04 (s, 1H), 7.90 (s, 1H), 7.43 (s, 1H), 7.36 (s, 1H), 7.30 (d, J=4.9, 1H), 7.11 (s, 1H), 4.67 (s, 1H), 4.05 (q, J=7.1, 2H), 2.39-2.21 (m, 4H), 1.95-1.58 (m, 8H), 1.17 (t, J=7.1, 3H).

Step 2:

Ethyl cis-4-hydroxy-4-[1-(3-methyl-5-{[4-(trifluoromethyl)pyrimidin-2-yl]amino}phenyl)-1H-imidazol-4-yl]cyclohexanecarboxylate (250 mg, 0.511 mmol) was suspended in MeOH (3.5 mL) in a microwave vial, and 1 N NaOH (1.021 mL, 1.021 mmol) was added. The reaction was heated to 100° C. for 10 min in the microwave. The colorless solution was adjusted to a pH of 3-4 with 1 N HCl, diluted with water, and extracted with 15% IPA/CHCl$_3$ (4×). The combined organic layers were dried ($MgSO_4$) and evaporated to provide cis-4-hydroxy-4-[1-(3-methyl-5-{[4-(trifluoromethyl)pyrimidin-2-yl]amino}phenyl)-1H-imidazol-4-yl]cyclohexanecarboxylic acid (223 mg, 95%) as an off-white solid. MS ESI calc. For $C_{22}H_{23}F_3N_5O_3$ [M+H]$^+$ 462. found 462. $^1$H NMR (500 MHz, DMSO-$d_6$) δ 11.98 (s, 1H), 10.34 (s, 1H), 8.84 (d, J=4.9, 1H), 8.02 (s, 1H), 7.89 (s, 1H), 7.44 (s, 1H), 7.35 (s, 1H), 7.30 (d, J=4.9, 1H), 7.10 (s, 1H), 4.65 (s, 1H), 2.33 (s, 3H), 2.25-2.11 (m, 1H), 1.88-1.60 (m, 7H).

Step 3:

Cis-4-Hydroxy-4-[1-(3-methyl-5-{[4-(trifluoromethyl)pyrimidin-2-yl]amino}phenyl)-1H-imidazol-4-yl]cyclohexanecarboxylic acid (55 mg, 0.119 mmol), EDC (45.7 mg, 0.238 mmol), HOBT (36.5 mg, 0.238 mmol), and methylamine hydrochloride (16.1 mg, 0.238 mmol) were combined in DMF (2.5 mL), and DIEA (42 µL 0.238 mmol) was added. The reaction was stirred at room temperature overnight. It was subsequently diluted with water and extracted with EtOAc (1×) and 15% IPA/CHCl$_3$ (2×). The combined organic layers were dried ($MgSO_4$) and evaporated to a yellow gum. Trituration with $CH_2Cl_2$ precipitated a solid that was filtered and dried to provide cis-4-hydroxy-N-methyl-4-[1-(3-methyl-5-{[4-(trifluoromethyl)pyrimidin-2-yl]amino}phenyl)-1H-imidazol-4-yl]cyclohexanecarboxamide as a white solid (40 mg, 71%). MS ESI calc. for $C_{23}H_{26}F_3N_6O_2$ [M+H]$^+$ 475. found 475. $^1$H NMR (500 MHz, DMSO-$d_6$) δ 10.34 (s, 1H), 8.84 (d, J=4.9, 1H), 7.99 (d, J=1.2, 1H), 7.88 (s, 1H), 7.64 (q, J=4.3, 1H), 7.43 (s, 1H), 7.32 (d, J=1.2, 1H), 7.30 (d, J=4.9, 1H), 7.10 (s, 1H), 5.74 (s, 1H), 4.61 (s, 1H), 2.54 (s, 3H), 2.33 (s, 3H), 2.12-2.03 (m, 1H), 1.91-1.68 (m, 6H), 1.55-1.44 (m, 2H).

Example 2

Trans-4-[1-(3-methyl-5-{[4-(trifluoromethyl)pyrimidin-2-yl]amino}phenyl)-1H-imidazol-4-yl]cyclohexanecarboxylic acid and Cis-4-[1-(3-methyl-5-{[4-(trifluoromethyl)pyrimidin-2-yl]amino}phenyl)-1H-imidazol-4-yl]cyclohexanecarboxylic acid

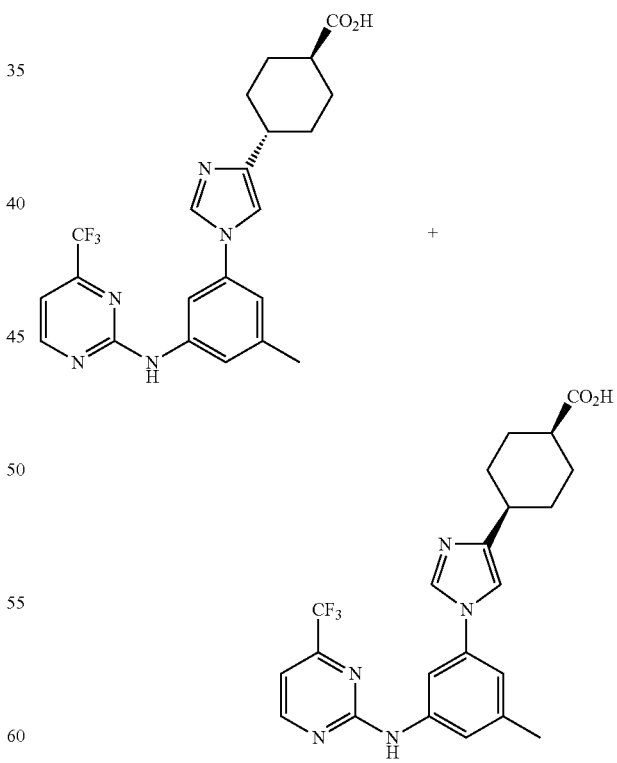

Step 1:

Ethyl trans-4-hydroxy-4-[1-(3-methyl-5-{[4-(trifluoromethyl)pyrimidin-2-yl]amino}phenyl)-1H-imidazol-4-yl]cyclohexanecarboxylate (200 mg, 0.409 mmol) was combined with Eaton's reagent (2.00 mL) and stirred at 60° C. for 1 h.

The reaction was cooled to room, carefully neutralized with saturated NaHCO$_3$, and extracted with EtOAc (2×). The combined organic layers were washed with brine, dried (MgSO$_4$), and evaporated. Flash chromatography (10-100% EtOAc/hexanes then 0-10% MeOH/EtOAc) afforded 139 mg (72%) of ethyl 4-[1-(3-methyl-5-{[4-(trifluoromethyl)pyrimidin-2-yl]amino}phenyl)-1H-imidazol-4-yl]cyclohex-3-ene-1-carboxylate as a colorless solid. MS ESI calc. for C$_{24}$H$_{25}$F$_3$N$_5$O$_2$ [M+H]$^+$ 472. found 472. $^1$H NMR (500 MHz, DMSO-d$_6$) δ 10.34 (s, 1H), 8.84 (d, J=4.6, 1H), 8.13 (s, 1H), 7.95 (s, 1H), 7.55 (s, 1H), 7.41 (s, 1H), 7.30 (d, J=4.3, 1H), 7.13 (s, 1H), 6.37 (s, 1H), 4.07 (s, 2H), 2.59 (s, 1H), 2.46-2.20 (m, 7H), 2.02 (s, 1H), 1.70 (s, 1H), 1.18 (t, J=6.9, 3H).

Step 2:

Ethyl 4-[1-(3-methyl-5-{[4-(trifluoromethyl)pyrimidin-2-yl]amino}phenyl)-1H-imidazol-4-yl]cyclohex-3-ene-1-carboxylate (100 mg, 0.212 mmol) was taken up in EtOH (5 mL). Pd/C (10%, 56 mg, 0.053 mmol) was added, and the reaction was purged with hydrogen (3×). The reaction was stirred under a hydrogen balloon at room temperature overnight. The reaction was not complete by LC/MS, so additional Pd/C (50 mg) was added, and the reaction was stirred for another 24 h at room temperature under a hydrogen balloon. The reaction was filtered through CELITE and evaporated to dryness. Flash chromatography (dry load, 50-100% EtOAc/hexanes) afforded ethyl 4-[1-(3-methyl-5-{[4-(trifluoromethyl)pyrimidin-2-yl]amino}phenyl)-1H-imidazol-4-yl]cyclohexanecarboxylate as a 70:30 mixture of diastereomers (colorless foam, 73 mg, 73%). MS ESI calc. for C$_{24}$H$_{27}$F$_3$N$_5$O$_2$ [M+H]$^+$ 474. found 474.

Step 3:

Ethyl 4-[1-(3-methyl-5-{[4-(trifluoromethyl)pyrimidin-2-yl]amino}phenyl)-1H-imidazol-4-yl]cyclohexanecarboxylate (70 mg, 0.148 mmol) was suspended in MeOH (2.0 mL) in a microwave vial, and 1 N NaOH (0.296 mL, 0.296 mmol) was added. The reaction was heated to 100° C. for 10 min in the microwave. The colorless solution was adjusted to a pH of 3-4 with 1 N HCl, diluted with water, and extracted with 15% IPA/CHCl$_3$ (3×). The combined organic layers were dried (MgSO$_4$) and evaporated. The residue was separated by SFC (MeOH/CO$_2$) to provide 12 mg (18%) of trans-4-[1-(3-methyl-5-{[4-(trifluoromethyl)pyrimidin-2-yl]amino}phenyl)-1H-imidazol-4-yl]cyclohexanecarboxylic acid as a yellow solid, and 18 mg (27%) of cis-4-[1-(3-methyl-5-{[4-(trifluoromethyl)pyrimidin-2-yl]amino}phenyl)-1H-imidazol-4-yl]cyclohexanecarboxylic acid as a yellow solid.

trans isomer: MS ESI calc. for C$_{22}$H$_{23}$F$_3$N$_5$O$_2$ [M+H]+ 446. found 446. $^1$H NMR (600 MHz, DMSO-d$_6$) δ 12.01 (s, 1H), 10.31 (s, 1H), 8.83 (d, J=4.9, 1H), 7.96 (d, J=1.3, 1H), 7.89 (s, 1H), 7.38 (s, 1H), 7.28 (d, J=4.9, 1H), 7.24 (s, 1H), 7.07 (s, 1H), 2.45-2.39 (m, 1H), 2.31 (s, 3H), 2.18 (tt, J=3.5, 11.8, 1H), 2.03 (dd, J=2.9, 13.1, 2H), 1.94 (dd, J=2.9, 13.5, 2H), 1.49-1.26 (m, 4H).

cis isomer: MS ESI calc. for C$_{22}$H$_{23}$F$_3$N$_5$O$_2$ [M+H]+ 446. found 446. $^1$H NMR (500 MHz, DMSO-d$_6$) δ 12.05 (s, 1H), 10.32 (s, 1H), 8.84 (d, J=4.9, 1H), 8.02 (s, 1H), 7.93 (s, 1H), 7.40 (s, 1H), 7.30 (d, J=4.8, 2H), 7.12 (s, 1H), 2.70-2.56 (m, 1H), 2.33 (s, 3H), 1.97-1.83 (m, 2H), 1.84-1.64 (m, 4H), 1.66-1.49 (m, 2H).

Example 3

4-[1-(3-methyl-5-{[4-(trifluoromethyl)pyrimidin-2-yl]amino}phenyl)-1H-imidazol-4-yl]cyclohex-3-ene-1-carboxylic acid

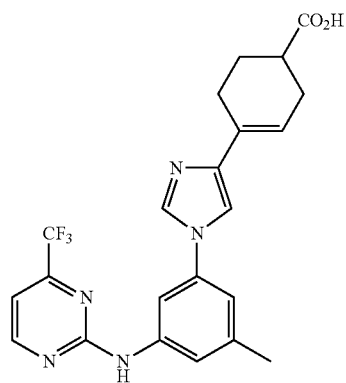 [SMILES: Cc1cc(Nc2nccc(C(F)(F)F)n2)cc(-n2cnc(C3=CCC(C(=O)O)CC3)c2)c1]

Step 1:

Ethyl 4-[1-(3-methyl-5-{[4-(trifluoromethyl)pyrimidin-2-yl]amino}phenyl)-1H-imidazol-4-yl]cyclohex-3-ene-1-carboxylate (25 mg, 0.053 mmol) was suspended in MeOH (1.0 mL) in a microwave vial, and 1 N NaOH (0.106 ml, 0.106 mmol) was added. The reaction was heated to 100° C. for 10 min in the microwave. The colorless solution was adjusted to a pH of 3-4 with 1 N HCl, diluted with water, and extracted with 15% IPA/CHCl$_3$ (3×). The combined organic layers were dried (MgSO$_4$) and evaporated to provide 4-[1-(3-methyl-5-{[4-(trifluoromethyl)pyrimidin-2-yl]amino}phenyl)-1H-imidazol-4-yl]cyclohex-3-ene-1-carboxylic acid as an off-white solid (19 mg, 81%). MS ESI calc. for C$_{22}$H$_{21}$F$_3$N$_5$O$_2$ [M+H]+ 444. found 444. $^1$H NMR (500 MHz, DMSO-d$_6$) δ 12.18 (s, 1H), 10.34 (s, 1H), 8.84 (d, J=4.9, 1H), 8.05 (s, 1H), 7.94 (s, 1H), 7.51 (s, 1H), 7.40 (s, 1H), 7.30 (d, J=4.9, 1H), 7.13 (s, 1H), 6.37 (s, 1H), 2.55-2.19 (m, 8H), 2.01 (s, 1H), 1.67 (s, 1H).

Example 4

6,6-Dimethyl-4-[1-(3-methyl-5-{[4-(trifluoromethyl)pyrimidin-2-yl]amino}phenyl)-1H-imidazol-4-yl]cyclohex-3-ene-1-carboxylic acid

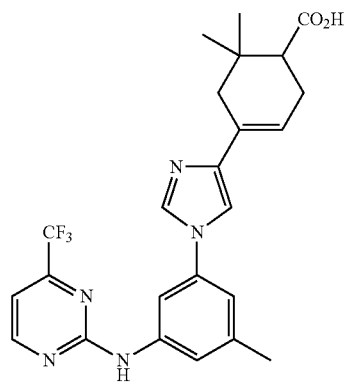 [SMILES: Cc1cc(Nc2nccc(C(F)(F)F)n2)cc(-n2cnc(C3=CCC(C(=O)O)C(C)(C)C3)c2)c1]

Step 1:

A vial was charged with N-(3-iodo-5-methylphenyl)-4-(trifluoromethyl)pyrimidin-2-amine (293 mg, 0.773 mmol), methyl rac-(1R,4R)-4-hydroxy-4-(1H-imidazol-4-yl)-2,2-dimethylcyclohexanecarboxylate (195 mg, 0.773 mmol), CuI (44.2 mg, 0.232 mmol), $K_2CO_3$ (214 mg, 1.546 mmol), and proline (53.4 mg, 0.464 mmol), sealed, and purged with nitrogen (3×). DMSO (4 mL) was added, and the reaction was stirred at 120° C. in an oil bath for 2 h. The reaction was cooled to room temperature, diluted with water, and extracted with EtOAc (2×). The combined organic layers were washed with brine, dried ($MgSO_4$), and evaporated. Flash chromatography (dry load, 20-100% EtOAc/hexanes) allowed separation of the two major products. The higher $R_f$ band corresponded to methyl 6,6-dimethyl-4-[1-(3-methyl-5-{[4-(trifluoromethyl)pyrimidin-2-yl]amino}phenyl)-1H-imidazol-4-yl]cyclohex-3-ene-1-carboxylate (tan foam, 46 mg, 12%), and the lower $R_f$ band corresponded to methyl rac-(1R,4R)-4-hydroxy-2,2-dimethyl-4-[1-(3-methyl-5-{[4-(trifluoromethyl)pyrimidin-2-yl]amino}phenyl)-1H-imidazol-4-yl]cyclohexanecarboxylate (yellow foam, 161 mg, 41%).

Olefin product: MS ESI calc. for $C_{25}H_{27}F_3N_5O_2$ [M+H]+ 486. found 486. $^1$H NMR (500 MHz, DMSO-$d_6$) δ 10.33 (s, 1H), 8.84 (d, J=4.9, 1H), 8.08 (s, 1H), 7.96 (s, 1H), 7.54 (s, 1H), 7.39 (s, 1H), 7.30 (d, J=4.9, 1H), 7.15 (s, 1H), 6.31 (s, 1H), 3.60 (s, 3H), 2.47-2.28 (m, 6H), 2.27-2.12 (m, 2H), 1.02 (s, 3H), 0.94 (s, 3H).

Alcohol product: MS ESI calc. for $C_{25}H_{29}F_3N_5O_3$ [M+H]+ 504. found 504. $^1$H NMR (500 MHz, DMSO-$d_6$) δ 10.34 (s, 1H), 8.84 (d, J=4.9, 1H), 8.07 (s, 1H), 7.95 (s, 1H), 7.41 (m, 2H), 7.30 (d, J=4.9, 1H), 7.14 (s, 1H), 4.53 (s, 1H), 3.53 (s, 3H), 2.44-2.21 (m, 6H), 1.93-1.81 (m, 1H), 1.81-1.64 (m, 1H), 1.61-1.33 (m, 2H), 1.06 (s, 3H), 0.56 (s, 3H).

Step 2:

Methyl 6,6-dimethyl-4-[1-(3-methyl-5-{[4-(trifluoromethyl)pyrimidin-2-yl]amino}phenyl)-1H-imidazol-4-yl]cyclohex-3-ene-1-carboxylate (35 mg, 0.072 mmol) was suspended in MeOH (1.5 mL) in a microwave vial, and 1 N NaOH (0.433 ml, 0.433 mmol) was added. The reaction was heated to 120° C. for 2 h in the microwave. The crude reaction was acidified to pH 3-4 with 1 N HCl. The mixture was then diluted with water and extracted with 15% IPA/CHCl$_3$ (2×). The combined organic layers were dried (MgSO$_4$) and evaporated. Flash chromatography (0-10% MeOH/CH$_2$Cl$_2$) afforded 6,6-dimethyl-4-[1-(3-methyl-5-{[4-(trifluoromethyl)pyrimidin-2-yl]amino}phenyl)-1H-imidazol-4-yl]cyclohex-3-ene-1-carboxylic acid (20 mg, 59%) as an off-white solid. MS ESI calc. for $C_{24}H_{25}F_3N_5O_2$ [M+H]+ 472. found 472. $^1$H NMR (500 MHz, DMSO-$d_6$) δ 12.09 (s, 1H), 10.33 (s, 1H), 8.84 (d, J=4.9, 1H), 8.06 (d, J=1.1, 1H), 7.96 (s, 1H), 7.52 (s, 1H), 7.39 (s, 1H), 7.30 (d, J=4.9, 1H), 7.14 (s, 1H), 6.32 (s, 1H), 2.43-2.26 (m, 6H), 2.26-2.10 (m, 2H), 1.06 (s, 3H), 0.96 (s, 3H).

Example 5

Rac-(1R,3S,4S)-3,4-dihydroxy-1-methyl-4-[1-(3-methyl-5-{[4-(trifluoromethyl)pyrimidin-2-yl]amino}phenyl)-1H-imidazol-4-yl]cyclohexanecarboxylic acid and Rac-(1R,3R,4R)-3,4-dihydroxy-1-methyl-4-[1-(3-methyl-5-{[4-(trifluoromethyl)pyrimidin-2-yl]amino}phenyl)-1H-imidazol-4-yl]cyclohexanecarboxylic acid

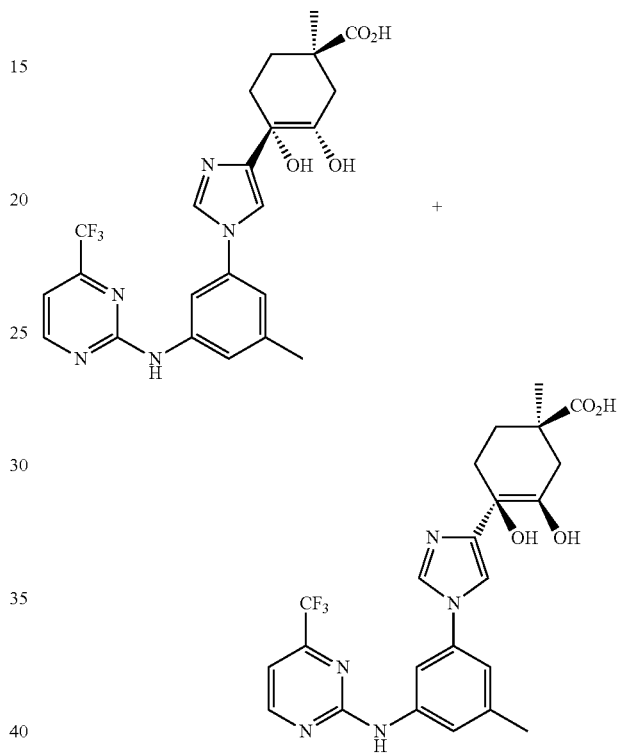

Step 1:
1-Methyl-4-[1-(3-methyl-5-{[4-(trifluoromethyl)pyrimidin-2-yl]amino}phenyl)-1H-imidazol-4-yl]cyclohex-3-ene-1-carboxylic acid (130 mg, 0.284 mmol) and NMO (66.6 mg, 0.568 mmol) were dissolved in 8:1 acetone/water (4.5 mL), and OsO$_4$ (4% in water, 0.223 ml, 0.028 mmol) was added. The reaction was stirred at room temperature overnight. The reaction was diluted with 10% Na$_2$S$_2$O$_3$ and EtOAc. The aqueous layer was acidified (pH 3-4) with 1 N HCl and further extracted with 15% IPA/CHCl$_3$ (2×). The combined organic layers were dried (MgSO$_4$) and evaporated. The diastereomers were separated by reverse phase HPLC (MeCN/water w/0.1% formic acid) to provide 42 mg (30%) of rac-(1R,3S,4S)-3,4-dihydroxy-1-methyl-4-[1-(3-methyl-5-{[4-(trifluoromethyl)pyrimidin-2-yl]amino}phenyl)-1H-imidazol-4-yl]cyclohexanecarboxylic acid as a white solid, and 13 mg (9%) of rac-(1R,3R,4R)-3,4-dihydroxy-1-methyl-4-[1-(3-methyl-5-{[4-(trifluoromethyl)pyrimidin-2-yl]amino}phenyl)-1H-imidazol-4-yl]cyclohexanecarboxylic acid as a white solid.

Isomer 1 (anti OH and CO$_2$H): MS ESI calc. for $C_{23}H_{25}F_3N_5O_4$ [M+H]+ 492. found 492. $^1$H NMR (500 MHz, DMSO-$d_6$) δ 12.18 (s, 1H), 10.35 (s, 1H), 8.84 (d, J=4.9, 1H), 8.07 (s, 1H), 7.86 (s, 1H), 7.46 (s, 1H), 7.40 (s, 1H), 7.30 (d, J=4.9, 1H), 7.10 (s, 1H), 4.52-4.26 (m, 2H), 3.76 (d, J=9.0, 1H), 2.33 (s, 3H), 2.03-1.95 (m, 1H), 1.86-1.71 (m, 2H), 1.68-1.57 (m, 1H), 1.57-1.40 (m, 2H), 1.13 (s, 3H).

Isomer 2 (syn OH and CO$_2$H): MS ESI calc. for C$_{23}$H$_{25}$F$_3$N$_5$O$_4$ [M+H]+ 492. found 492. $^1$H NMR (500 MHz, DMSO-d$_6$) δ 12.15 (s, 1H), 10.35 (s, 1H), 8.84 (d, J=4.9, 1H), 8.02 (s, 1H), 7.88 (s, 1H), 7.44 (s, 1H), 7.40 (s, 1H), 7.30 (d, J=4.9, 1H), 7.09 (s, 1H), 4.37 (s, 2H), 3.89 (dd, J=4.2, 11.4, 1H), 2.33 (s, 3H), 2.02-1.85 (m, 3H), 1.76-1.60 (m, 1H), 1.60-1.47 (m, 1H), 1.37-1.27 (m, 1H), 1.17 (s, 3H).

The following examples were prepared in a manner analogous to that described in Examples 1-5.

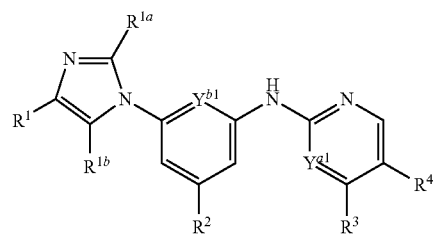

I

Formula Ia: (Y$^{b1}$=N, Y$^{a1}$=CH, R$^{1a}$=R$^{1b}$=R$^4$=H)
Formula Ib: (Y$^{b1}$=CH, Y$^{a1}$=N, R$^{1a}$=R$^{1b}$=R$^4$=H)

| Ex. | R$^1$ Form | R$^2$ Formula | R$^3$ | Chemical Name | [M + H]$^+$ Calc'd | [M + H]$^+$ Found |
|---|---|---|---|---|---|---|
| 6 | SYN; Formate Salt | CH$_3$ (Ib) | CF$_3$ | 2-{cis-4-hydroxy-4-[1-(3-methyl-5-{[4-(trifluoromethyl)pyrimidin-2-yl]amino}phenyl)-1H-imidazol-4-yl]cyclohexyl)acetamide | 475 | 475 |
| 7 | RACEMIC; ANTI; Formate Salt | CH$_3$ (Ib) | CF$_3$ | trans-4-{1-hydroxy-1-[1-(3-methyl-5-{[4-(trifluoromethyl)pyrimidin-2-yl]amino}phenyl)-1H-imidazol-4-yl]ethyl] cyclohexanecarboxamide | 489 | 489 |
| 8 | TFA Salt | CH$_3$ (Ib) | c-propyl | (2S)-3-(1-{3-[(4-cyclopropylpyrimidin-2-yl)amino]-5-methylphenyl}-1H-imidazol-4-yl)-2-hydroxypropanoic acid | 380 | 380 |
| 9 | RACEMIC; ANTI; Free Base | CH$_3$ (Ib) | CH$_3$ | trans-4-[1-hydroxy-1-(1-{3-methyl-5-[(4-methyl-pyrimidin-2-yl)amino]-phenyl}-1H-imidazol-4-yl)ethyl]cyclohexane-carboxylic acid | 436 | 436 |
| 10 | RACEMIC; ANTI; Free Base | CH$_3$ (Ib) | CF$_3$ | trans-4-{1-hydroxy-1-[1-(3-methyl-5-{[4-(trifluoromethyl)pyrimidin-2-yl]amino}phenyl)-1H-imidazol-4-yl]ethyl}-cyclohexanecarboxylic acid | 490 | 490 |

-continued

| Ex. | R¹ Form | R² Formula | R³ | Chemical Name | [M + H]⁺ Calc'd | [M + H]⁺ Found |
|---|---|---|---|---|---|---|
| 11 | 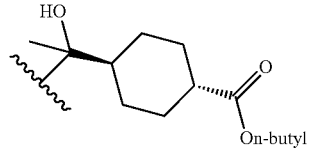<br>RACEMIC;<br>ANTI<br>Free Base | CH₃ (Ib) | CH₃ | Butyl trans-4-[1-hydroxy-1-(1-{3-methyl-5-[(4-methylpyrimidin-2-yl)amino]phenyl}-1H-imidazol-4-yl)ethyl]-cyclohexanecarboxylate | 492 | 492 |
| 12 | 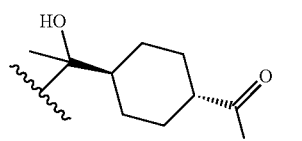<br>RACEMIC;<br>ANTI<br>Free Base | CH₃ (Ib) | CF₃ | Butyl trans-4-{1-hydroxy-1-[1-(3-methyl-5-[(4-(trifluoromethyl)-pyrimidin-2-yl]amino}-phenyl)-1H-imidazol-4-yl]ethyl}cyclohexane-carboxylate | 546 | 546 |
| 13 | 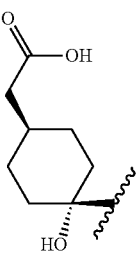 [SMILES: *[C@]1(O)CC[C@H](CC(=O)O)CC1]<br>ANTI<br>Free Base | CH₃ (Ia) | CF₃ | {trans-4-hydroxy-4-[1-(4-methyl-6-{[4-(trifluoromethyl)pyridin-2-yl]amino}pyridin-2-yl)-1H-imidazol-4-yl]cyclohexyl}acetic acid | 476 | 476 |
| 14 | 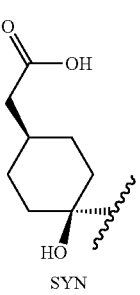<br>SYN<br>TFA Salt | CH₃ (Ia) | CF₃ | {cis-4-hydroxy-4-[1-(4-methyl-6-{[4-(trifluoromethyl)pyridin-2-yl]amino}pyridin-2-yl)-1H-imidazol-4-yl]cyclohexyl}acetic acid | 476 | 476 |
| 15 | 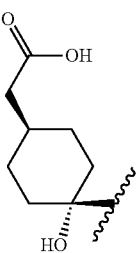 [SMILES: *[C@]1(O)CC[C@H](CC(=O)O)CC1]<br>ANTI<br>Free Base | CH₃ (Ib) | CF₃ | {trans-4-hydroxy-4-[1-(3-methyl-5-{[4-(trifluoromethyl)pyrimidin-2-yl]amino}phenyl)-1H-imidazol-4-yl]-cyclohexyl}acetic acid | 476 | 476 |

-continued

| Ex. | R¹ Form | R² Formula | R³ | Chemical Name | [M + H]⁺ Calc'd | [M + H]⁺ Found |
|---|---|---|---|---|---|---|
| 16 | 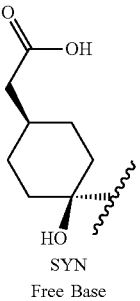<br>SYN<br>Free Base | CH₃<br>(Ib) | CF₃ | {cis-4-hydroxy-4-[1-(3-methyl-5-{[4-(trifluoromethyl)pyrimidin-2-yl]amino}phenyl)-1H-imidazol-4-yl]-cyclohexyl}acetic acid | 476 | 476 |
| 17 | 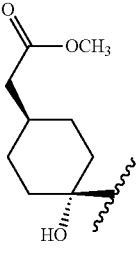 [SMILES: *[C@]1(O)CC[C@H](CC(=O)OC)CC1]<br>ANTI<br>Free Base | CH₃<br>(Ib) | CF₃ | Methyl {trans-4-hydroxy-4-[1-(3-methyl-5-{[4-(trifluoromethyl)pyrimidin-2-yl]amino}phenyl)-1H-imidazol-4-yl]-cyclohexyl}acetate | 490 | 490 |
| 18 | 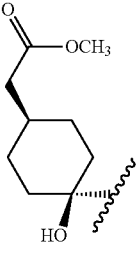 [SMILES: *[C@]1(O)CC[C@@H](CC(=O)OC)CC1]<br>SYN<br>Free Base | CH₃<br>(Ib) | CF₃ | Methyl {cis-4-hydroxy-4-[1-(3-methyl-5-{[4-(trifluoromethyl)pyrimidin-2-yl]amino}phenyl)-1H-imidazol-4-yl]-cyclohexyl}acetate | 490 | 490 |
| 19 | 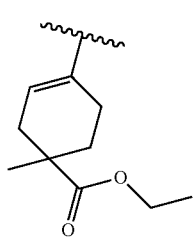 [SMILES: *C1=CCC(C)(C(=O)OCC)CC1]<br>RACEMIC<br>Free Base | CH₃<br>(Ib) | CF₃ | Ethyl 1-methyl-4-[1-(3-methyl-5-{[4-(trifluoromethyl)-pyrimidin-2-yl]amino}-phenyl)-1H-imidazol-4-yl]cyclohex-3-ene-1-carboxylate | 486 | 486 |
| 20 | 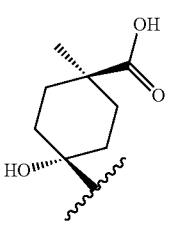<br>ANTI<br>Free Base | CH₃<br>(Ib) | CF₃ | trans-4-hydroxy-1-methyl-4-[1-(3-methyl-5-{[4-(trifluoromethyl)-pyrimidin-2-yl]amino)-phenyl)-1H-imidazol-4-yl]cyclohexanecarboxylic acid | 476 | 476 |

-continued

| Ex. | R¹ Form | R² Formula | R³ | Chemical Name | [M + H]⁺ Calc'd | [M + H]⁺ Found |
|---|---|---|---|---|---|---|
| 21 | 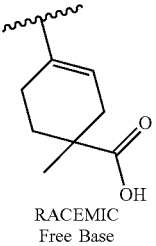<br>RACEMIC<br>Free Base | CH₃<br>(Ib) | CF₃ | 1-methyl-4-[1-(3-methyl-5-{[4-(trifluoromethyl)-pyrimidin-2-yl]amino}-phenyl)-1H-imidazol-4-yl]cyclohex-3-ene-1-carboxylic acid | 458 | 458 |
| 22 | 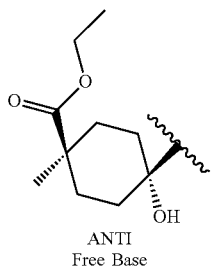<br>ANTI<br>Free Base | CH₃<br>(Ib) | CF₃ | Ethyl trans-4-hydroxy-1-methyl-4-[1-(3-methyl-5-{[4-(trifluoromethyl)pyrimidin-2-yl]amino}phenyl)-1H-imidazol-4-yl]cyclohexanecarboxylate | 504 | 504 |
| 23 | 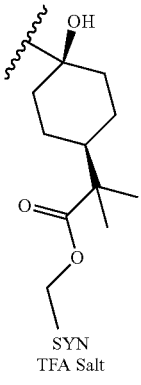<br>SYN<br>TFA Salt | CH₃<br>(Ia) | CF₃ | Ethyl 2-{cis-4-hydroxy-4-[1-(4-methyl-6-{[4-(trifluoromethyl)pyridin-2-yl]amino}pyridin-2-yl)-1H-imidazol-4-yl]cyclohexyl}-2-methylpropanoate | 532 | 532 |
| 24 | 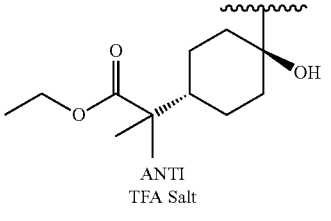<br>ANTI<br>TFA Salt | CH₃<br>(Ia) | CF₃ | Ethyl 2-{trans-4-hydroxy-4-[1-(4-methyl-6-{[4-(trifluoromethyl)-pyridin-2-yl]amino}-pyridin-2-yl)-1H-imidazol-4-yl]-cyclohexyl}-2-methylpropanoate | 532 | 532 |
| 25 | 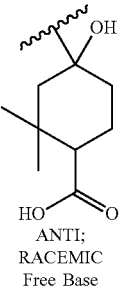<br>ANTI;<br>RACEMIC<br>Free Base | CH₃<br>(Ib) | CF₃ | 4-hydroxy-2,2-dimethyl-4-[1-(3-methyl-5-{[4-(trifluoromethyl)pyrimidin-2-yl]amino}phenyl)-1H-imidazol-4-yl]-cyclohexanecarboxylic acid | 490 | 490 |
| 26 | 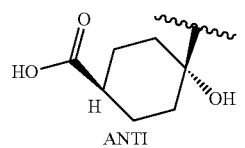<br>ANTI | CH₃<br>(Ia) | CF₃ | trans-4-hydroxy-4-[1-(4-methyl-6-{[4-(trifluoromethyl)pyridin-2-yl]amino}pyridin-2-yl)-1H-imidazol-4-yl]cyclohexanecarboxylic | 462 | 462 |

-continued

| Ex. | R¹ Form | R² Formula | R³ | Chemical Name | [M + H]⁺ Calc'd | [M + H]⁺ Found |
|---|---|---|---|---|---|---|
| | Free Base | | | acid | | |
| 27 | SYN Free Base | CH₃ (Ia) | CF₃ | cis-4-hydroxy-4-[1-(4-methyl-6-{[4-(trifluoromethyl)pyridin-2-yl]amino}pyridin-2-yl)-1H-imidazol-4-yl]cyclohexanecarboxylic acid | 462 | 462 |
| 28 | ANTI Free Base | CH₃ (Ia) | CF₃ | Ethyl trans-4-hydroxy-4-[1-(4-methyl-6-{[4-(trifluoromethyl)pyridin-2-yl]amino}pyridin-2-yl)-1H-imidazol-4-yl]cyclohexane-carboxylate | 490 | 490 |
| 29 | SYN Free Base | CH₃ (Ia) | CF₃ | Ethyl cis-4-hydroxy-4-[1-(4-methyl-6-{[4-(trifluoromethyl)pyridin-2-yl]amino}pyridin-2-yl)-1H-imidazol-4-yl]cyclohexane-carboxylate | 490 | 490 |
| 30 | SYN Free Base | CH₃ (Ib) | CF₃ | cis-1-[1-(3-methyl-5-{[4-(trifluoromethyl)pyrimidin-2-yl]amino}phenyl)-1H-imidazol-4-yl]-4-(morpholin-4-ylcarbonyl)cyclohexanol | 531 | 531 |
| 31 | SYN Free Base | CH₃ (Ib) | CF₃ | cis-1-[1-(3-methyl-5-{[4-(trifluoromethyl)pyrimidin-2-yl]amino}phenyl)-1H-imidazol-4-yl]-4-(pyrrolidin-1-ylcarbonyl)cyclohexanol | 515 | 515 |
| 32 | SYN Free Base | CH₃ (Ib) | CF₃ | cis-4-hydroxy-N,N-dimethyl-4-[1-(3-methyl-5-{[4-(trifluoromethyl)-pyrimidin-2-yl]amino}-phenyl)-1H-imidazol-4-yl]cyclohexane-carboxamide | 489 | 489 |
| 33 | | CH₃ (Ib) | CF₃ | trans-4-hydroxy-4-[1-(3-methyl-5-{[4-(trifluoro-methyl)pyrimidin-2-yl]amino}phenyl)-1H-imidazol-4-yl]-cyclohexanecarboxamide | 461 | 461 |

| Ex. | R¹ Form | R² Formula | R³ | Chemical Name | [M + H]⁺ Calc'd | [M + H]⁺ Found |
|---|---|---|---|---|---|---|
| 34 | ANTI Free Base / SYN Free Base (HO-cyclohexyl-C(O)NH₂) | CH₃ (Ib) | CF₃ | cis-4-hydroxy-4-[1-(3-methyl-5-{[4-(trifluoromethyl)-pyrimidin-2-yl]amino}phenyl)-1H-imidazol-4-yl]-cyclohexanecarboxamide | 461 | 461 |
| 35 | ANTI ISOMER Free Base (HO-cyclohexyl-COOH) | CH₃ (Ib) | CF₃ | trans-4-hydroxy-4-[1-(3-methyl-5-[[4-(trifluoromethyl)pyrimidin-2-yl]amino}phenyl)-1H-imidazol-4-yl]cyclohexanecarboxylic acid | 462 | 462 |
| 36 | ANTI ISOMER Free Base (HO-cyclohexyl-COOEt) | CH₃ (Ib) | CF₃ | Ethyl trans-4-hydroxy-4-[1-(3-methyl-5-{[4-(trifluoromethyl)pyrimidin-2-yl]amino}phenyl)-1H-imidazol-4-yl]-cyclohexanecarboxylate | 490 | 490 |

Example 37

Cis-1-[1-(3-methyl-5-{[4-(trifluoromethyl)pyrimidin-2-yl]amino}phenyl)-1H-imidazol-4-yl]cyclohexane-1,4-diol

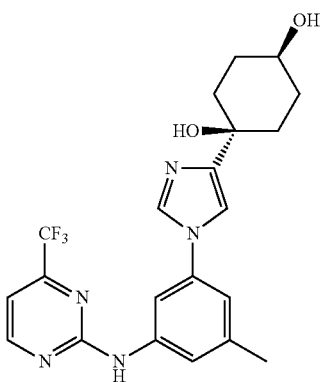 [SMILES: Cc1cc(Nc2nccc(C(F)(F)F)n2)cc(-n2cnc([C@]3(O)CC[C@@H](O)CC3)c2)c1]

Step 1:

A vial was charged with N-(3-iodo-5-methylphenyl)-4-(trifluoromethyl)pyrimidin-2-amine (397 mg, 1.048 mmol), cis-4-hydroxy-4-(1H-imidazol-4-yl)cyclohexyl benzoate (300 mg, 1.048 mmol), CuI (59.9 mg, 0.314 mmol), K₂CO₃ (290 mg, 2.096 mmol), and proline (72.4 mg, 0.629 mmol), sealed, and purged with nitrogen (3×). DMSO (5 mL) was added, and the reaction was stirred at 120° C. in an oil bath for 5 h. The reaction was diluted with water and extracted with EtOAc (2×). The combined organic layers were washed with brine, dried (MgSO₄), and evaporated. Flash chromatography (30-100% EtOAc/hexanes) afforded 240 mg (43%) of cis-4-hydroxy-4-[1-(3-methyl-5-{[4-(trifluoromethyl)pyrimidin-2-yl]amino}phenyl)-1H-imidazol-4-yl]cyclohexyl benzoate as a white solid. MS ESI calc. for C₂₈H₂₇F₃N₅O₃ [M+H]⁺ 538. found 538.

Step 2:

Cis-4-hydroxy-4-[1-(3-methyl-5-{[4-(trifluoromethyl)pyrimidin-2-yl]amino}phenyl)-1H-imidazol-4-yl]cyclohexyl benzoate (100 mg, 0.186 mmol) was suspended in MeOH (2.0 mL) in a microwave vial, and 1 N NaOH (0.372 ml, 0.372 mmol) was added. The reaction was heated to 100° C. for 15 min in the microwave. The colorless solution was diluted with water and extracted with EtOAc (2×). The combined organic layers were dried (MgSO₄) and evaporated. The residue was triturated with CH₂Cl₂, filtered, and dried to provide cis-1-[1-(3-methyl-5-{[4-(trifluoromethyl)pyrimidin-2-yl]amino}phenyl)-1H-imidazol-4-yl]cyclohexane-1,4-diol as a white powder. MS ESI calc. for C₂₁H₂₃F₃N₅O₂ [M+H]⁺ 434. found 434. ¹H NMR (500 MHz, DMSO-d₆) δ 10.34 (s, 1H), 8.84 (d, J=4.9, 1H), 7.98 (s, 1H), 7.88 (s, 1H), 7.43 (s, 1H), 7.32 (d, J=0.6, 1H), 7.30 (d, J=4.9, 1H), 7.10 (s, 1H), 4.56 (s, 1H), 4.44 (d, J=4.4, 1H), 3.52-3.37 (m, 1H), 2.33 (s, 3H), 1.87-1.68 (m, 4H), 1.67-1.52 (m, 4H).

Example 38

Cis-1-(1-{3-methyl-5-[(4-methylpyrimidin-2-yl)amino]phenyl}-1H-imidazol-4-yl)cyclohexane-1,4-diol

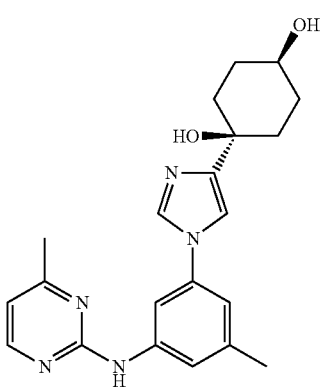 [SMILES: Cc1cc(Nc2nccc(C)n2)cc(-n2cnc([C@]3(O)CC[C@@H](O)CC3)c2)c1]

Step 1:

A vial was charged with 3-iodo-5-methylaniline (484 mg, 2.078 mmol), cis-4-hydroxy-4-(1H-imidazol-4-yl)cyclohexyl benzoate (595 mg, 2.078 mmol), CuI (119 mg, 0.623 mmol), $K_2CO_3$ (574 mg, 4.16 mmol), and proline (144 mg, 1.247 mmol), sealed, and purged with nitrogen (3×). DMSO (10 mL) was added, and the reaction was stirred at 110° C. in an oil bath for 2 h. The reaction was cooled to room temperature, diluted with water, and extracted with EtOAc (2×). The combined organic layers were washed with brine, dried ($MgSO_4$), and evaporated. Flash chromatography (dry load, 0-10% MeOH/EtOAc) afforded cis-4-[1-(3-amino-5-methylphenyl)-1H-imidazol-4-yl]-4-hydroxycyclohexyl benzoate as an off-white solid. MS ESI calc. for $C_{23}H_{26}N_3O_3$ [M+H]+ 392. found 392.

Step 2:

2-Chloro-4-methylpyrimidine (65.7 mg, 0.511 mmol), cis-4-[1-(3-amino-5-methylphenyl)-1H-imidazol-4-yl]-4-hydroxycyclohexyl benzoate (200 mg, 0.511 mmol), $Pd(OAc)_2$ (11.5 mg, 0.051 mmol), Xantphos (44.3 mg, 0.077 mmol), and $Cs_2CO_3$ (333 mg, 1.022 mmol) were combined in a 5 mL microwave vial, sealed, and purged with nitrogen (3×). Degassed dioxane (2.5 mL) was added, and the reaction was purged again with nitrogen (2×). The mixture was then heated to 100° C. and stirred for 1 h. The reaction was cooled to room temperature, diluted with water, and extracted with EtOAc (2×). The combined organic layers were washed with brine, dried ($MgSO_4$), and evaporated. Flash chromatography (0-5% MeOH/EtOAc) afforded cis-4-hydroxy-4-(1-{3-methyl-5-[(4-methylpyrimidin-2-yl)amino]phenyl}-1H-imidazol-4-yl)cyclohexyl benzoate as a white solid. MS ESI calc. for $C_{28}H_{29}N_5O_3$ [M+H]+ 484. found 484.

Step 3:

Cis-4-Hydroxy-4-(1-{3-methyl-5-[(4-methylpyrimidin-2-yl)amino]phenyl}-1H-imidazol-4-yl)cyclohexyl benzoate (115 mg, 0.238 mmol) was suspended in MeOH (2.0 mL) in a microwave vial, and 1 N NaOH (0.476 ml, 0.476 mmol) was added. The reaction was heated to 110° C. for 15 min in the microwave. The reaction mixture was diluted with water and extracted with EtOAc (2×). The combined organic layers were dried ($MgSO_4$) and evaporated. The residue was triturated with $CH_2Cl_2$/hexanes to precipitate a colorless solid that was isolated by filtration and dried, affording cis-1-(1-{3-methyl-5-[(4-methylpyrimidin-2-yl)amino]phenyl}-1H-imidazol-4-yl)cyclohexane-1,4-diol as a white powder. MS ESI calc. for $C_{21}H_{26}N_5O_2$ [M+H]+ 380. found 380. $^1$H NMR (500 MHz, DMSO-$d_6$) δ 9.67 (s, 1H), 8.35 (d, J=4.9, 1H), 7.96 (s, 1H), 7.92 (s, 1H), 7.47 (s, 1H), 7.29 (s, 1H), 6.97 (s, 1H), 6.76 (d, J=5.0, 1H), 4.57 (s, 1H), 4.44 (d, J=4.3, 1H), 3.42 (s, 1H), 2.36 (s, 3H), 2.31 (s, 3H), 1.87-1.67 (m, 4H), 1.67-1.53 (m, 4H). r The following examples were prepared in a manner analogous to that described in Examples 37 and 38.

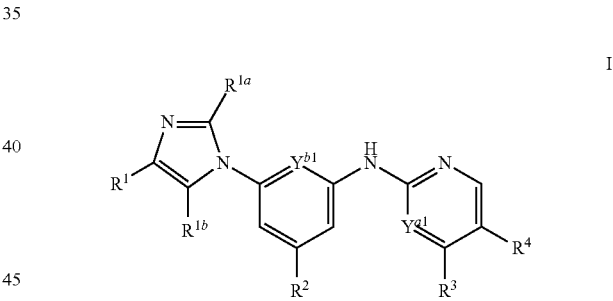

Formula Ia: ($Y^{b1}$=N, $Y^{a1}$=CH, $R^{1a}$=$R^{1b}$=$R^4$=H)
Formula Ib: ($Y^{b1}$=CH, $Y^{a1}$=N, $R^{1a}$=$R^{1b}$=$R^4$=H)

| Ex. | $R^1$ Form | $R^2$ Formula | $R^3$ | Chemical Name | [M + H]+ Calc'd | [M + H]+ Found |
|---|---|---|---|---|---|---|
| 39 | ![SYN Free Base] | $CH_3$ (Ib) | $OCH_3$ | cis-1-(1-{3-[(4-methoxypyrimidin-2-yl)amino]-5-methylphenyl}-1H-imidazol-4-yl)cyclohexane-1,4-diol | 396 | 396 |

-continued

| Ex. | R¹ Form | R² Formula | R³ | Chemical Name | [M + H]⁺ Calc'd | [M + H]⁺ Found |
|---|---|---|---|---|---|---|
| 40 | 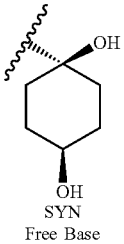<br>SYN<br>Free Base | CH₃ (Ib) | c-propyl | cis-1-(1-{3-[(4-cyclopropylpyrimidin-2-yl)amino]-5-methylphenyl}-1H-imidazol-4-yl)cyclohexane-1,4-diol | 406 | 406 |
| 41 | 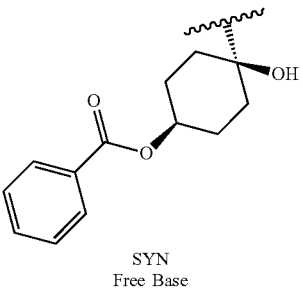<br>SYN<br>Free Base | CH₃ (Ib) | OCH₃ | cis-4-hydroxy-4-(1-{3-[(4-methoxypyrimidin-2-yl)amino]-5-methylphenyl}-1H-imidazol-4-yl)cyclohexyl benzoate | 500 | 500 |
| 42 | 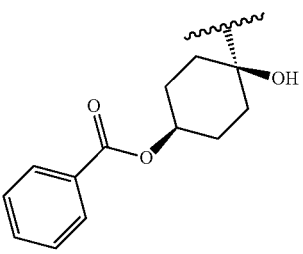 [SMILES: *[C@]1(O)CC[C@@H](OC(=O)c2ccccc2)CC1]<br>SYN<br>Free Base | CH₃ (Ib) | c-propyl | cis-4-(1-{3-[(4-cyclopropylpyrimidin-2-yl)amino]-5-methylphenyl}-1H-imidazol-4-yl)-4-hydroxycyclohexyl benzoate | 510 | 510 |
| 43 | 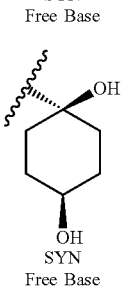<br>SYN<br>Free Base | CH₃ (Ia) | CH₃ R⁴=F | cis-1-(1-{6-[(5-fluoro-4-methylpyridin-2-yl)amino]-4-methylpyridin-2-yl}-1H-imidazol-4-yl)cyclohexane-1,4-diol | 398 | 398 |
| 44 | 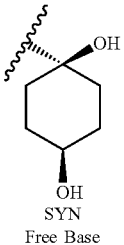<br>SYN<br>Free Base | CH₃ (Ia) | CH₃ R⁴=Cl | cis-1-(1-{6-[(5-chloro-4-methylpyridin-2-yl)amino]-4-methylpyridin-2-yl}-1H-imidazol-4-yl)cyclohexane-1,4-diol | 414 | 414 |
| 45 | 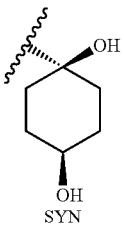<br>SYN | CH₃ (Ia) | c-propyl | cis-1-(1-{6-[(4-cyclopropylpyridin-2-yl)amino]-4-methylpyridin-2-yl}-1H-imidazol-4-yl)cyclohexane-1,4-diol | 406 | 406 |

| Ex. | R¹ Form | R² Formula | R³ | Chemical Name | [M + H]⁺ Calc'd | [M + H]⁺ Found |
|---|---|---|---|---|---|---|
| 46 | (cis cyclohexane-1,4-diol) SYN Free Base | CH₃ (Ia) | CH₃ | cis-1-(1-{4-methyl-6-[(4-methylpyridin-2-yl)amino]pyridin-2-yl}-1H-imidazol-4-yl)cyclohexane-1,4-diol | 380 | 380 |
| 47 | (cis cyclohexane-1,4-diol) SYN Free Base | CH₃ (Ia) | t-butyl | cis-1-(1-{6-[(4-tert-butylpyridin-2-yl)amino]-4-methylpyridin-2-yl}-1H-imidazol-4-yl)cyclohexane-1,4-diol | 422 | 422 |
| 48 | (cyclohexyl benzoate) SYN Free Base | CH₃ (Ia) R⁴=F | CH₃ | cis-4-(1-{6-[(5-fluoro-4-methylpyridin-2-yl)amino]-4-methylpyridin-2-yl}-1H-imidazol-4-yl)-4-hydroxycyclohexyl benzoate | 502 | 502 |
| 49 | (cyclohexyl benzoate) SYN Free Base | CH₃ (Ia) R⁴=Cl | CH₃ | cis-4-(1-{6-[(5-chloro-4-methylpyridin-2-yl)amino]-4-methylpyridin-2-yl}-1H-imidazol-4-yl)-4-hydroxycyclohexyl benzoate | 518 | 518 |
| 50 | (cyclohexyl benzoate) SYN Free Base | CH₃ (Ia) | c-propyl | cis-4-(1-{6-[(4-cyclopropylpyridin-2-yl)amino]-4-methylpyridin-2-yl}-1H-imidazol-4-yl)-4-hydroxycyclohexyl benzoate | 510 | 510 |

-continued

| Ex. | R¹ Form | R² Formula | R³ | Chemical Name | [M + H]⁺ Calc'd | [M + H]⁺ Found |
|---|---|---|---|---|---|---|
| 51 | SYN Free Base | CH₃ (Ia) | CH₃ | cis-4-hydroxy-4-(1-{4-methyl-6-[(4-methylpyridin-2-yl)amino]pyridin-2-yl}-1H-imidazol-4-yl)cyclohexyl benzoate | 484 | 484 |
| 52 | SYN Free Base | CH₃ (Ia) | t-butyl | cis-4-(1-{6-[(4-tert-butylpyridin-2-yl)amino]-4-methylpyridin-2-yl}-1H-imidazol-4-yl)-4-hydroxycyclohexyl benzoate | 526 | 526 |
| 53 | Free Base | CH₃ (Ib) | CF₃ | 4-hydroxy-4-[1-(3-methyl-5-{[4-(trifluoromethyl)pyrimidin-2-yl]amino}phenyl)-1H-imidazol-4-yl]cyclohexanone | 432 | 432 |
| 54 | TRANS Free Base | CH₃ (Ib) | CF₃ | (1S,3S,4S)-3-methyl-1-[1-(3-methyl-5-{[4-(trifluoromethyl)pyrimidin-2-yl]amino}phenyl)-1H-imidazol-4-yl]cyclohexane-1,4-diol | 448 | 448 |
| 55 | TRANS Free Base | CH₃ (Ib) | CF₃ | (1R,3S,4S)-3-methyl-1-[1-(3-methyl-5-{[4-(trifluoromethyl)pyrimidin-2-yl]amino}phenyl)-1H-imidazol-4-yl]cyclohexane-1,4-diol | 448 | 448 |
| 56 | CIS Free Base | CH₃ (Ib) | CF₃ | (1S,3S,4R)-3-methyl-1-[1-(3-methyl-5-{[4-(trifluoromethyl)pyrimidin-2-yl]amino}phenyl)-1H-imidazol-4-yl]cyclohexane-1,4-diol | 448 | 448 |
| 57 | SYN Free Base | CH₃ (Ib) | CH₃ R⁴=F | cis-1-(1-{3-[(5-fluoro-4-methylpyrimidin-2-yl)amino]-5-methylphenyl}-1H-imidazol-4-yl)cyclohexane-1,4-diol | 398 | 398 |

-continued

| Ex. | R¹ Form | R² Formula | R³ | Chemical Name | [M + H]⁺ Calc'd | [M + H]⁺ Found |
|---|---|---|---|---|---|---|
| 58 | SYN Free Base (4-hydroxycyclohexyl benzoate structure) | CH₃ (Ib) | CH₃ R⁴=F | cis-4-(1-{3-[(5-fluoro-4-methylpyrimidin-2-yl)amino]-5-methylphenyl}-1H-imidazol-4-yl)-4-hydroxycyclohexyl benzoate | 502 | 502 |
| 59 | SYN Free Base (cyclohexane-1,4-diol structure) | CH₃ (Ib) | c-propyl R⁴=F | cis-1-(1-{3-[(4-cyclopropyl-5-fluoropyrimidin-2-yl)amino]-5-methylphenyl}-1H-imidazol-4-yl)cyclohexane-1,4-diol | 424 | 424 |
| 60 | SYN Free Base (4-hydroxycyclohexyl benzoate structure) | CH₃ (Ib) | c-propyl R⁴=F | cis-4-(1-{3-[(4-cyclopropyl-5-fluoropyrimidin-2-yl)amino]-5-methylphenyl}-1H-imidazol-4-yl)-4-hydroxycyclohexyl benzoate | 528 | 528 |
| 61 | ANTI Free Base (cyclohexane-1,4-diol structure) | CH₃ (Ia) | CF₃ | trans-1-[1-(4-methyl-6-{[4-(trifluoromethyl)pyridin-2-yl]amino}pyridin-2-yl)-1H-imidazol-4-yl]cyclohexane-1,4-diol | 434 | 434 |
| 62 | SYN Free Base (cyclohexane-1,4-diol structure) | CH₃ (Ia) | CF₃ | cis-1-[1-(4-methyl-6-{[4-(trifluoromethyl)pyridin-2-yl]amino}pyridin-2-yl)-1H-imidazol-4-yl]cyclohexane-1,4-diol | 434 | 434 |

-continued

| Ex. | R¹ Form | R² Formula | R³ | Chemical Name | [M + H]⁺ Calc'd | [M + H]⁺ Found |
|---|---|---|---|---|---|---|
| 63 | ANTI Free Base | CH₃ (Ia) | CF₃ | trans-4-hydroxy-4-[1-(4-methyl-6-{[4-(trifluoromethyl)pyridin-2-yl]amino}pyridin-2-yl)-1H-imidazol-4-yl]cyclohexyl benzoate | 538 | 538 |
| 64 | SYN Free Base | CH₃ (Ia) | CF₃ | cis-4-hydroxy-4-[1-(4-methyl-6-{[4-(trifluoromethyl)pyridin-2-yl]amino}pyridin-2-yl)-1H-imidazol-4-yl]cyclohexyl benzoate | 538 | 538 |
| 65 | ANTI Free Base | CH₃ (Ib) | CF₃ | trans-1-[1-(3-methyl-5-{[4-(trifluoromethyl)pyrimidin-2-yl]amino}phenyl)-1H-imidazol-4-yl]cyclohexane-1,4-diol | 434 | 434 |
| 66 | ANTI Free Base | CH₃ (Ib) | CF₃ | trans-4-hydroxy-4-[1-(3-methyl-5-{[4-(trifluoromethyl)pyrimidin-2-yl]amino}phenyl)-1H-imidazol-4-yl]cyclohexyl benzoate | 538 | 538 |

Example 67

2-Methyl-1-(3-methyl-5-{[4-(trifluoromethyl)pyrimidin-2-yl]amino}phenyl)-1H-imidazole-4-carboxylic acid

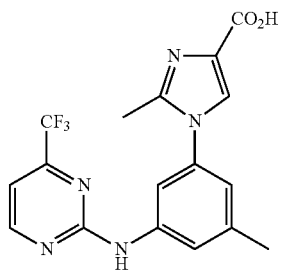 [SMILES: Cc1cc(Nc2nccc(C(F)(F)F)n2)cc(-n2cc(C(=O)O)nc2C)c1]

Step 1:

A vial was charged with N-(3-iodo-5-methylphenyl)-4-(trifluoromethyl)pyrimidin-2-amine (600 mg, 1.583 mmol), ethyl 2-methyl-1H-imidazole-4-carboxylate (244 mg, 1.583 mmol), CuI (90 mg, 0.475 mmol), K₂CO₃ (437 mg, 3.17 mmol), and proline (109 mg, 0.950 mmol), sealed, and purged with nitrogen (3×). DMSO (8 mL) was added, and the reaction was stirred at 120° C. in an oil bath overnight. Additional CuI (90 mg, 0.475 mmol) and proline (109 mg, 0.950 mmol) were added. After another 24 h at 120° C., the reaction was cooled to room temperature, diluted with water, and extracted with EtOAc (2×). The combined organic layers were washed with brine, dried (MgSO₄), and evaporated. Flash chromatography (dry load, 30-100% EtOAc/hexanes) afforded ethyl 2-methyl-1-(3-methyl-5-{[4-(trifluoromethyl)pyrimidin-2-yl]amino}phenyl)-1H-imidazole-4-carboxylate as an off-white foam MS ESI calc. for C₁₉H₁₉F₃N₅O₂ [M+H]⁺ 406. found 406. ¹H NMR (500 MHz, DMSO) δ 10.42 (s, 1H), 8.84 (d, J=4.9, 1H), 7.93 (s, 1H), 7.76 (s, 1H), 7.57 (s, 1H), 7.31 (d, J=4.9, 1H), 6.98 (s, 1H), 4.21 (q, J=7.1, 2H), 2.34 (s, 3H), 2.31 (s, 3H), 1.25 (t, J=7.1, 3H).

Step 2:

Ethyl 2-methyl-1-(3-methyl-5-{[4-(trifluoromethyl)pyrimidin-2-yl]amino}phenyl)-1H-imidazole-4-carboxylate (50 mg, 0.123 mmol) was suspended in MeOH (2.0 mL) in a microwave vial, and 1 N NaOH (0.247 ml, 0.247 mmol) was added. The reaction was heated to 100° C. for 10 min in the microwave. The reaction mixture was acidified to pH 3-4 with 1 N HCl, diluted with water, and extracted with 15% IPA/CHCl$_3$ (2×). The combined organic layers were dried (MgSO$_4$) and evaporated to give 2-methyl-1-(3-methyl-5-{[4-(trifluoromethyl)pyrimidin-2-yl]amino}phenyl)-1H-imidazole-4-carboxylic acid as an off-white solid. MS ESI calc. for $C_{12}H_{15}F_3N_5O_2$ [M+H]$^+$ 378. found 378. $^1$H NMR (500 MHz, DMSO-d$_6$) δ 12.28 (s, 1H), 10.42 (s, 1H), 8.84 (d, J=4.9, 1H), 7.85 (s, 1H), 7.75 (s, 1H), 7.57 (s, 1H), 7.31 (d, J=4.9, 1H), 6.97 (s, 1H), 2.34 (s, 3H), 2.31 (s, 3H).

Example 68

2-[2-Methyl-1-(3-methyl-5-{[4-(trifluoromethyl)pyrimidin-2-yl]amino}phenyl)-1H-imidazol-4-yl]propan-2-ol

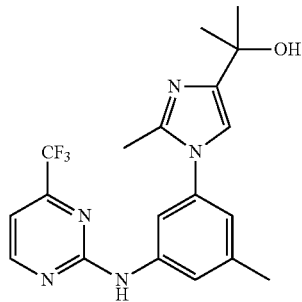 [SMILES: Cc1cc(Nc2nccc(C(F)(F)F)n2)cc(-n2cc(C(C)(C)O)nc2C)c1]

Step 1:

A solution of ethyl 2-methyl-1-(3-methyl-5-{[4-(trifluoromethyl)pyrimidin-2-yl]amino}phenyl)-1H-imidazole-4-carboxylate (74 mg, 0.183 mmol) in THF (4 mL) was cooled to −78° C., and methylmagnesium bromide (3.0 M in Et$_2$O, 0.243 ml, 0.730 mmol) was added. The dry ice bath was removed, and the reaction was warmed to room temperature. The reaction was quenched with saturated NH$_4$Cl and extracted with EtOAc (2×). The combined organic layers were washed with brine, dried (MgSO$_4$), and evaporated. Flash chromatography (25-100% EtOAc/hexanes then 0-10% MeOH/EtOAc) afforded 2-[2-methyl-1-(3-methyl-5-{[4-(trifluoromethyl)pyrimidin-2-yl]amino}phenyl)-1H-imidazol-4-yl]propan-2-ol as a white foam. MS ESI calc. for $C_{19}H_{21}F_3N_5O$ [M+H]$^+$ 392. found 392. $^1$H NMR (500 MHz, DMSO-d$_6$) δ 10.37 (s, 1H), 8.84 (d, J=4.9, 1H), 7.70 (s, 1H), 7.52 (s, 1H), 7.30 (d, J=4.9, 1H), 6.95 (s, 1H), 6.88 (s, 1H), 4.66 (s, 1H), 2.34 (s, 3H), 2.28 (s, 3H), 1.39 (s, 6H).

Example 69

Methyl 1-{6-[(4-chloropyridin-2-yl)amino]pyridin-2-yl}-1H-imidazole-4-carboxylate

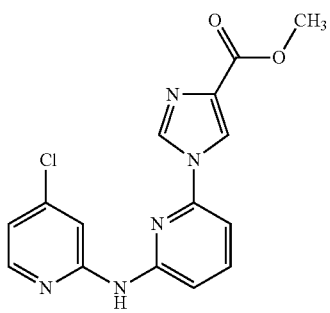 [SMILES: COC(=O)c1cn(-c2cccc(Nc3cc(Cl)ccn3)n2)cn1]

To a suspension of the 4-chloropyridin-2-amine (45.6 mg, 0.454 mmole), methyl 1-(6-bromopyridin-2-yl)-1H-imidazole-4-carboxylate (100 mg, 0.354 mmole), NaOtBu (34.1 mg, 0.354 mmole), DTBPF (16.82 mg, 0.035 mmole) and Pd$_2$ dba$_3$ (18.35 mg, 0.018 mmole) under nitrogen was added dixoane (1.7 mL) and the mixture heated to 100° C. for 18 hr. The reaction was cooled to room temperature and diluted with methyltetrahydrofuran (50 mL) and sat. NH$_4$Cl (aq) (5 mL). The reaction was filtered through CELITE in vacuo and the residue was purified by HPLC (Column Max-RP 100×21 mm, eluent: 25-50% CH$_3$CN/30 mM NH$_4$HCO$_3$(aq)) to afford methyl methyl 1-{6-[(4-chloropyridin-2-yl)amino]pyridin-2-yl}-1H-imidazole-4-carboxylate. MS ESI calcd. For $C_{15}H_{13}ClN_5O_2$ [M+H]$^+$ 330. found 330. $^1$H NMR (500 MHz, DMSO-d$_6$): δ δ 10.24 (S, 1H); 8.60 (m, 2H); 8.28 (m, 1H), 7.91 (m, 1H); 7.82 (m, 1H); 7.70 (m, 1H); 7.47 (m, 1H); 7.08 (m, 1H); 3.82 (s, 3H).

Example 70

Pyrrolidin-1-yl[1-(3-{[4-(trifluoromethyl)pyrimidin-2-yl]amino}phenyl)-1H-imidazol-4-yl]methanone

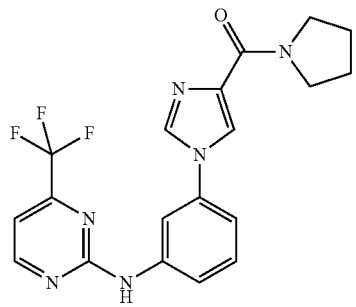 [SMILES: O=C(c1cn(-c2cccc(Nc3nccc(C(F)(F)F)n3)c2)cn1)N1CCCC1]

Step 1:

To a mixture of 2-chloro-4-(trifluoromethyl)pyrimidine (115 mg, 0.628 mmole), methyl 1-(3-aminophenyl)-1H-imidazole-4-carboxylate (130 mg, 0.598 mmole), Cs$_2$CO$_3$ (390 mg, 1.197 mmole), Pd(OAc)$_2$ (13 mg, 0.060 mmole), and Xanthphos (52 mg, 0.09 mmole) was added dixoane (3.99 mL) and the mixture was heated to 105° C. for 18 hr. The reaction was cooled to room temperature diluted with methyltetrahydrofuran (30 mL) and filtered through CELITE. The filtrate was concentrated in vacuo and the residue purified by chromatography on silica (24 g, 50:50 to 0:100 hexanes:EtOAc) to afford methyl 1-(3-{[4-(trifluoromethyl)pyrimidin-2-yl]amino}phenyl)-1H-imidazole-4-carboxylate as a light yellow solid. $^1$H NMR (400 MHz, CDCl$_3$): δ 8.72 (m, 1H); 8.23 (s, 1H); 8.04 (s, 1H); 7.97 (s, 1H); 7.78 (m, 1H); 7.48 (m, 2H); 7.14 (m, 2H); 3.95 (s, 3H).

Step 2:

To a solution of methyl 1-(3-{[4-(trifluoromethyl)pyrimidin-2-yl]amino}phenyl)-1H-imidazole-4-carboxylate in 1/1 THF/MeOH (2 mL) was added the LiOH (aq. 1M) (0.413 mL, 0.413 mmole). The mixture was heated to 50° C. for 2 hr allowed to cool to room temperature and acidified with HCl (aq. 1N, 0.5 mL). The mixture was diluted with EtOAc (30 mL) and brine (30 mL). The organic layer was removed, concentrated in vacuo, and flushed with methanol (2×20 mL) afford crude 1-(3-{[4-(trifluoromethyl)pyrimidin-2-yl]amino}phenyl)-1H-imidazole-4-carboxylic acid as a white solid. The solid was used without further purification. $^1$H NMR (500 MHz, DMSO-d$_6$): δ 10.50 (s, 1H); 9.88 (m, 1H); 8.25 (m, 2H), 8.17 (m, 1H); 7.71 (m, 1H); 7.45 (m, 1H); 7.36 (m, 2H); 6.84 (s, 1H).

Step 3:

To a solution of 1-(3-{[4-(trifluoromethyl)pyrimidin-2-yl]amino}phenyl)-1H-imidazole-4-carboxylic acid (24.1 mg, 0.069 mmole) in DMF (1 mL) at 0° C. was added pyrrolidine (8.56 uL, 0.104 mmole), HATU (39.4 mg, 0.104 mmole) and diisopropylethylamine (24 uL, 0.138 mmole). The mixture was stirred for 30 minutes at room temperature. The reaction was diluted with EtOAc (30 mL) and washed with sat. NaHCO$_3$ (aq) (30 mL) followed brine (2×10 mL). The aqueous extracts were washed with EtOAc (30 mL) and the combined organic layers were dried over Na$_2$SO$_4$, filtered and concentrated in vacuo. to an oil. The residue was purified by HPLC (Column: Max-RP 50×21 mm, eluent: 30-70% CH$_3$CN/0.6% Formic acid (aq) to afford pyrrolidin-1-yl[1-(3-{[4-(trifluoromethyl)-pyrimidin-2-yl]amino}phenyl)-1H-imidazol-4-yl]methanone. MS ESI calcd. For C$_{19}$H$_{18}$F$_3$N$_6$O [M+H]$^+$ 403. found 403. $^1$H NMR (500 MHz, DMSO-d$_6$): δ δ 10.50 (s, 1H); 8.88 (m, 1H); 8.24 (m, 1H), 8.16 (s, 1H); 8.10 (s, 1H); 7.72 (m, 1H); 7.50 (m, 1H); 7.35 (m, 2H); 4.0-3.9 (m, 2H); 3.5-3.3 (m, 2H); 2.0-1.7 (m, 4H).

The following examples were prepared in a manner analogous to that described in Examples 67-70.

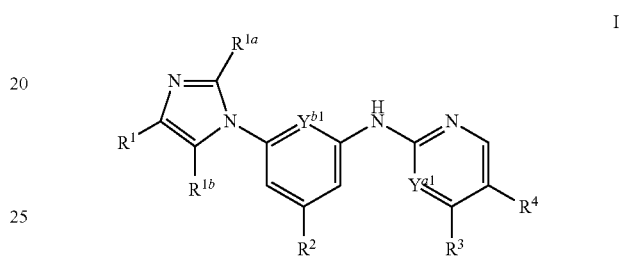

I

Formula Ia: ($Y^{b1}$=N, $Y^{a1}$=CH, $R^{1a}$=$R^{1b}$=$R^4$=H)
Formula Ib: ($Y^{b1}$=CH, $Y^{a1}$=N, $R^{1a}$=$R^{1b}$=$R^4$=H)

| Ex. | $R^1$ Form | $R^2$ Formula | $R^3$ | Chemical Name | [M + H]$^+$ Calc'd | [M + H]$^+$ Found |
|---|---|---|---|---|---|---|
| 71 | ![structure] TFA Salt | CH$_3$ (Ib) | CF$_3$ | 4-[1-(3-methyl-5-{[4-(trifluoromethyl)pyrimidin-2-yl]amino}-phenyl)-1H-imidazol-4-yl]benzoic acid | 440 | 440 |
| 74 | CH$_2$CH$_2$CO$_2$H Formate Salt | CH$_3$ (Ia) | CF$_3$ | 3-[1-(4-methyl-6-{[4-(trifluoromethyl)-pyridin-2-yl]amino}-pyridin-2-yl)-1H-imidazol-4-yl]-propanoic acid | 392 | 392 |
| 75 | CH$_2$CH$_2$CO$_2$H Formate Salt | CH$_3$ (Ib) | c-propyl | 3-(1-{3-[(4-cyclopropylpyrimidin-2-yl)amino]-5-methylphenyl}-1H-imidazol-4-yl)propanoic acid | 364 | 364 |
| 76 | CH$_2$CH$_2$CO$_2$H Free Base | CH$_3$ (Ib) | CF$_3$ | 3-[1-(3-methyl-5-{[4-(trifluoromethyl)pyrimidin-2-yl]amino}-phenyl)-1H-imidazol-4-yl]propanoic acid | 392 | 392 |
| 77 | CH$_2$CN Free Base | CH$_3$ (Ib) | CF$_3$ | [1-(3-methyl-5-{[4-(trifluoromethyl)pyrimidin-2-yl]amino}-phenyl)-1H-imidazol-4-yl]acetonitrile | 359 | 359 |
| 78 | CO$_2$H Free Base | CH$_3$ (Ib) | CF$_3$ | 1-(3-methyl-5-{[4-(trifluoromethyl)-pyrimidin-2-yl]amino}-phenyl)-1H-imidazole-4-carboxylic acid | 364 | 364 |

-continued

| Ex. | R¹ Form | R² Formula | R³ | Chemical Name | [M + H]⁺ Calc'd | [M + H]⁺ Found |
|---|---|---|---|---|---|---|
| 79 | 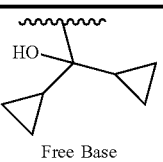<br>Free Base | NH₂<br>(Ia) | Cl | (1-{4-amino-6-[(4-chloropyridin-2-yl)amino}pyridin-2-yl}-1H-imidazol-4-yl)(dicyclopropyl)methanol | 397 | 397 |
| 80 | 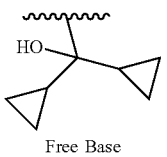<br>Free Base | CH₃<br>(Ia) | Cl | (1-{6-[(4-chloropyridin-2-yl)amino]-4-methylpyridin-2-yl}-1H-imidazol-4-yl)(dicyclopropyl)-methanol | 396 | 396 |
| 81 | 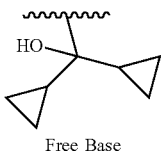<br>Free Base | H<br>(Ia) | Cl | (1-{6-[(4-chloropyridin-2-yl)amino]pyridin-2-yl}-1H-imidazol-4-yl)(dicyclopropyl)-methanol | 382 | 382 |
| 82 | 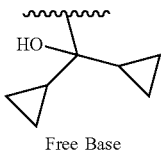<br>Free Base | H<br>(Ib) | CF₃ | dicyclopropyl[1-(3-{[4-(trifluoromethyl)-pyrimidin-2-yl]amino}phenyl)-1H-imidazol-4-yl]methanol | 416 | 416 |
| 83 | 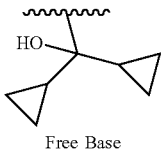<br>Free Base | H<br>(Ia) | CF₃ | dicyclopropyl[1-(6-{[4-(trifluoromethyl)-pyridin-2-yl]amino}pyridin-2-yl)-1H-imidazol-4-yl]methanol | 416 | 416 |
| 84 | 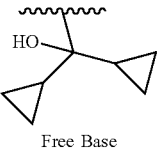<br>Free Base | NH₂<br>(Ia) | CF₃ | [1-(4-amino-6-{[4-(trifluoromethyl)pyridin-2-yl]amino[pyridin-2-yl)-1H-imidazol-4-yl](dicyclopropyl)-methanol | 431 | 431 |
| 85 | CO₂CH₃<br>Free Base | NH₂<br>(Ia) | CF₃ | Methyl 1-(4-amino-6-{[4-(trifluoromethyl)-pyridin-2-yl]amino}-pyridin-2-yl)-1H-imidazole-4-carboxylate | 379 | 379 |
| 86 | 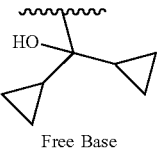<br>Free Base | CH₃<br>(Ia) | CH₃ | dicyclopropyl(1-{4-methyl-6-[(4-methylpyridin-2-yl)amino]pyridin-2-yl}-1H-imidazol-4-yl)methanol | 376 | 376 |
| 87 | C(CH₃)₂OH | CH₃<br>(Ia) | CH₃ | 2-(1-{4-methyl-6-[(4-methylpyridin-2-yl)amino]pyridin-2-yl}-1H-imidazol-4-yl)propan-2-ol | 324 | 324 |
| 88 | 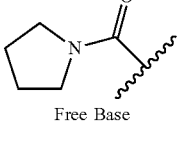<br>Free Base | CH₃<br>(Ib) | CF₃ | N-{3-methyl-5-[4-(pyrrolidin-1-ylcarbonyl)-1H-imidazol-1-yl]phenyl}-4-(trifluoromethyl)pyrimidin-2-amine | 417 | 417 |

-continued

| Ex. | R¹ Form | R² Formula | R³ | Chemical Name | [M + H]⁺ Calc'd | [M + H]⁺ Found |
|---|---|---|---|---|---|---|
| 89 | CONHCH(CH₃)₂ Free Base | CH₃ (Ib) | CF₃ | N-(1-methylethyl)-1-(3-methyl-5-{[4-(trifluoromethyl)pyrimidin-2-yl]amino}-phenyl)-1H-imidazole-4-carboxamide | 405 | 405 |
| 90 | C(CH₃)₂OH Free Base | Cl (Ia) | CF₃ | 2-[1-(4-chloro-6-{[4-(trifluoromethyl)pyridin-2-yl]amino}pyridin-2-yl)-1H-imidazol-4-yl]propan-2-ol | 398 | 398 |
| 91 | C(CH₃)₂OH Free Base | CF₃ (Ia) | CF₃ | 2-{1-[4-(trifluoro-methyl)-6-{[4-(trifluoromethyl)-pyridin-2-yl]amino}-pyridin-2-yl]-1H-imidazol-4-yl}propan-2-ol | 432 | 432 |
| 92 | C(CH₃)₂OH Free Base | CH₃ (Ia) | CF₃ | 2-[1-(4-methyl-6-{[4-(trifluoromethyl)pyridin-2-yl]amino}pyridin-2-yl)-1H-imidazol-4-yl]propan-2-ol | 378 | 378 |
| 93 | CO₂CH₃ Free Base | CH₃ (Ia) | CF₃ | Methyl 1-(4-methyl-6-{[4-(trifluoromethyl)-pyridin-2-yl]amino}-pyridin-2-yl)-1H-imidazole-4-carboxylate | 378 | 378 |
| 94 | C(CH₃)₂OH Free Base | H (Ia) | CF₃ | 2-[1-(6-{[4-(trifluoromethyl)-pyridin-2-yl]amino}-pyridin-2-yl)-1H-imidazol-4-yl]propan-2-ol | 364 | 364 |
| 95 | C(CH₃)₂OH Free Base | CH₃ (Ia) | Cl | 2-(1-{6-[(4-chloropyridin-2-yl)amino]-4-methylpyridin-2-yl}-1H-imidazol-4-yl)propan-2-ol | 344 | 344 |
| 96 | CO₂CH₃ Free Base | H (Ia) | CF₃ | Methyl 1-(6-{[4-(trifluoromethyl)pyridin-2-yl]amino}pyridin-2-yl)-1H-imidazole-4-carboxylate | 364 | 364 |
| 97 | CO₂CH₃ Free Base | CH₃ (Ia) | Cl | Methyl 1-{6-[(4-chloropyridin-2-yl)amino]-4-methylpyridin-2-yl}-1H-imidazole-4-carboxylate | 344 | 344 |
| 98 | CO₂CH₃ Free Base | CH₃ (Ib) | CF₃ | Methyl 1-(3-methyl-5-{[4-(trifluoromethyl)-pyrimidin-2-yl]amino}phenyl)-1H-imidazole-4-carboxylate | 378 | 378 |
| 99 | C(CH₃)₂OH Free Base | CH₃ | CF₃ | 2-[1-(3-methyl-5-{[4-(trifluoromethyl)pyrimidin-2-yl]amino}phenyl)-1H-imidazol-4-yl]propan-2-ol | 378 | 378 |
| 100 | C(CH₃)₂OH Free Base | H (Ia) | CH₃ | 2-(1-{6-[(4-methylpyridin-2-yl)amino]pyridin-2-yl}-1H-imidazol-4-yl)propan-2-ol | 310 | 310 |
| 101 | C(CH₃)₂OH Free Base | H (Ia) | Cl | 2-(1-{6-[(4-chloropyridin-2-yl)amino]pyridin-2-yl}-1H-imidazol-4-yl)propan-2-ol | 330 | 330 |

-continued

| Ex. | R1 Form | R2 Formula | R3 | Chemical Name | [M + H]+ Calc'd | [M + H]+ Found |
|---|---|---|---|---|---|---|
| 102 | CO2CH3 Free Base | H (Ia) | CH3 | Methyl 1-{6-[(4-methylpyridin-2-yl)amino]pyridin-2-yl}-1H-imidazole-4-carboxylate | 310 | 310 |
| 103 | CONHCH(CH3)2 Free Base | H (Ib) | CF3 | N-(1-methylethyl)-1-(3-{[4-(trifluoromethyl)pyrimidin-2-yl]amino}phenyl)-1H-imidazole-4-carboxamide | 391 | 391 |
| 104 | C(CH3)2OH Free Base | H (Ib) | CF3 | 2-[1-(3-{[4-(trifluoromethyl)pyrimidin-2-yl]amino}-phenyl)-1H-imidazol-4-yl]propan-2-ol | 364 | 364 |
| 105 | CH2CH2C(CH3)2OH Free Base | N-morpholinyl (Ib) | CF3 | 2-methyl-4-[1-(3-morpholin-4-yl-5-{[4-(trifluoromethyl)pyrimidin-2-yl]amino}-phenyl)-1H-imidazol-4-yl]butan-2-ol | 477 | 477 |
| 106 | CH2CH2CO2CH3 Free Base | N-morpholinyl (Ib) | CF3 | Methyl 3-[1-(3-morpholin-4-yl-5-{[4-(trifluoromethyl)pyrimidin-2-yl]amino}-phenyl)-1H-imidazol-4-yl]propanoate | 477 | 477 |
| 107 | C(CH3)2OH Free Base | N-morpholinyl (Ib) | CF3 | 2-[1-(3-morpholin-4-yl-5-{[4-(trifluoromethyl)pyrimidin-2-yl]amino}-phenyl)-1H-imidazol-4-yl]propan-2-ol | 449 | 449 |
| 108 | CO2CH3 Free Base | N-morpholinyl (Ib) | CF3 | Methyl 1-(3-morpholin-4-yl-5-{[4-(trifluoromethyl)-pyrimidin-2-yl]amino}-phenyl)-1H-imidazole-4-carboxylate | 449 | 449 |

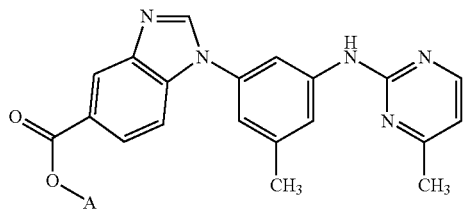

| Ex. | A | Form | Chemical Name | [M + H]+ Calc'd | [M + H]+ Found |
|---|---|---|---|---|---|
| 72 | H | Free base | 1-{3-methyl-5-[(4-methylpyrimidin-2-yl)amino]phenyl}-1H-benzimidazole-5-carboxylic acid | 360 | 360 |
| 73 | CH3 | Free base | Methyl 1-{3-methyl-5-[(4-methyl-pyrimidin-2-yl)amino]phenyl}-1H-benzimidazole-5-carboxylate | 374 | 374 |

Example 109

5-hydroxy-5-[1-(3-methyl-5-{[4-(trifluoromethyl)pyrimidin-2-yl]amino}phenyl)-1H-imidazol-4-yl]azepan-2-one

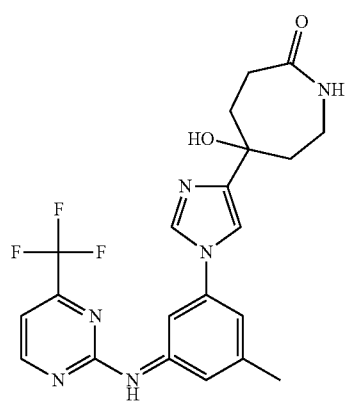

To 4-hydroxy-4-[1-(3-methyl-5-{[4-(trifluoromethyl)pyrimidin-2-yl]amino}phenyl)-1H-imidazol-4-yl]cyclohexanone (52.1 mg, 0.121 mmol) in an oven-dried, nitrogen cooled vial was added chloroform (0.6 mL), sodium azide (23.5 mg, 0.362 mmol), and methanesulfonic acid (0.094 mL, 1.45 mmol). The mixture was heated to 65° C. for 1.5 hours. The reaction was cooled to room temperature, diluted with water, and extracted with ethyl acetate. The combined organic layers were dried over sodium sulfate, filtered, and concentrated to find that the compound was actually in the aqueous layer. The residue was purified from the aqueous layer by reverse phase chromatography on C-18 to afford 5-hydroxy-5-[1-(3-methyl-5-{[4-(trifluoromethyl)pyrimidin-2-yl]amino}phenyl)-1H-imidazol-4-yl]azepan-2-one. MS ESI calcd. for $C_{21}H_{22}F_3N_6O_2$ $[M+H]^+$ 447. found 447. $^1H$ NMR (500 MHz, DMSO-$d_6$) δ 10.35 (s, 1H), 8.84 (d, J=4.9, 1H), 8.02 (t, J=3.3, 1H), 7.90 (s, 1H), 7.44 (m, 2H), 7.39 (s, 1H), 7.30 (d, J=4.9, 1H), 7.11 (s, 1H), 3.47-3.41 (m, 2H), 2.94-2.78 (m, 2H), 2.33 (s, 3H), 2.09-1.77 (m, 5H).

Example 110

2-Methyl-2-[1-(3-methyl-5-{[4-(trifluoromethyl)pyrimidin-2-yl]amino}phenyl)-1H-imidazol-4-yl]propanenitrile

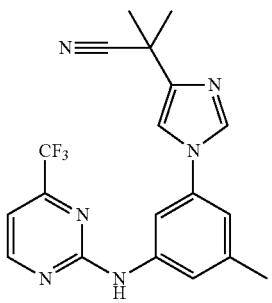 [SMILES: Cc1cc(Nc2nccc(C(F)(F)F)n2)cc(-n2cnc(C(C)(C)C#N)c2)c1]

To a flask were added [1-(3-methyl-5-{[4-(trifluoromethyl)pyrimidin-2-yl]amino}phenyl)-1H-imidazol-4-yl]acetonitrile (270 mg, 0.754 mmol) and THF (5400 μl) and the mixture cooled to −78° C. nBuLi (989 μl, 1.582 mmol) was added drop wise and the resulting mixture was stirred for 15 minutes. MeI (99 μl, 1.582 mmol) was added. Additional n-BuLi (250 uL) was added and the mixture was allowed to warm to room temperature and stir for 48 hrs. The reaction was diluted with EtOAc and washed with saturated NaHCO$_3$ and brine. The organic extract was dried over sodium sulfate, filtered and concentrated under reduced pressure. The residue was purified by reverse phase-HPLC (ACN/H$_2$O with 0.1% TFA) to afford 2-methyl-2-[1-(3-methyl-5-{[4-(trifluoromethyl)pyrimidin-2-yl]amino}phenyl)-1-imidazol-4-yl]propanenitrile. MS ESI calcd. for $C_{19}H_{18}F_3N_6$ $[M+H]^+$ 387 found 387. $^1H$ NMR (500 MHz, DMSO-$d_6$) δ 10.37 (s, 1H), 8.84 (d, J=4.8 Hz, 1H), 8.04 (s, 1H), 7.94 (s, 1H), 7.40 (m, 2H), 7.30 (d, J=4.9 Hz, 1H), 7.13 (s, 1H), 2.33 (m, 3H), 1.45 (s, 6H).

Example 111

2-Methyl-2-[1-(3-methyl-5-{[4-(trifluoromethyl)pyrimidin-2-yl]amino}phenyl)-1H-imidazol-4-yl]propanoic acid

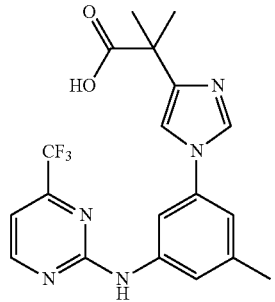 [SMILES: Cc1cc(Nc2nccc(C(F)(F)F)n2)cc(-n2cnc(C(C)(C)C(=O)O)c2)c1]

To a flask were added 2-methyl-2-[1-(3-methyl-5-{[4-(trifluoromethyl)pyrimidin-2-yl]amino}phenyl)-1-imidazol-4-yl]propanenitrile (10 mg, 0.026 mmol) and HCl (100 μl, 0.600 mmol) and the mixture stirred at 100° C. overnight. The reaction was diluted with EtOAc, washed with saturated NaHCO$_3$, then brine, dried over sodium sulfate, filtered and concentrated under reduced pressure to afford 2-methyl-2-[1-(3-methyl-5-{[4-(trifluoromethyl)pyrimidin-2-yl]amino}phenyl)-1-imidazol-4-yl]propanoic acid as a white powder. MS ESI calcd. for $C_{19}H_{19}F_3N_5O_2$ $[M+H]^+$ 406. found 406. $^1H$ NMR (500 MHz, DMSO-$d_6$) δ 10.38 (s, 1H), 8.68 (d, J=4.8, 1H), 8.25 (s, 1H), 7.73 (s, 1H), 7.55 (s, 1H), 7.41 (s, 1H), 7.24-7.10 (m, 2H), 2.35 (s, 6H), 2.48 (s, 3H).

Example 112

N-{3-Methyl-5-[4-(prop-1-en-2-yl)-1H-imidazol-1-yl]phenyl}-4-(trifluoromethyl)pyrimidin-2-amine

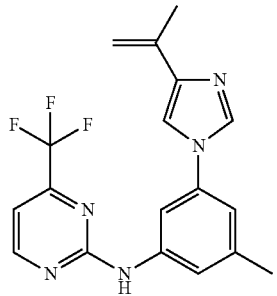 [SMILES: C=C(C)c1cn(-c2cc(C)cc(Nc3nccc(C(F)(F)F)n3)c2)cn1]

2-[1-(3-Methyl-5-{[4-(trifluoromethyl)pyrimidin-2-yl]amino}phenyl)-1H-imidazol-4-yl]propan-2-ol (442 mg, 1.17 mmol) was dissolved in CH$_2$Cl$_2$ (12 mL) and cooled to 0° C. Triethylamine (490 μL, 3.5 mmol) and methanesulfonyl chloride (137 μL, 1.76 mmol) were added sequentially. The solution was maintained 1 h at 0° C. Saturated aqueous ammonium chloride was added, and the solution was allowed to warm to rt. The layers were separated, and the aqueous portion was extracted with CH$_2$Cl$_2$ (2×). The combined organic fractions were dried over Na$_2$SO$_4$, filtered, and concentrated in vacuo. Purification via silica gel column chromatography (20%-50% EtOAc:Hex) gave N-{3- methyl-5-[4-(prop-1-en-2-yl)-1H-imidazol-1-yl]phenyl}-4-(trifluoromethyl)pyrimidin-2-amine as a white solid. MS ESI calcd. for $C_{18}H_{12}F_3N_5$ [M+H]+ 360. found 360. $^1$H NMR (500 MHz, CDCl$_3$) δ 8.68 (d, J=4.8 Hz, 1H), 8.01 (s, 1H), 7.89 (s, 1H), 7.43 (s, 1H), 7.28 (s, 1H), 7.11 (d, J=9.9 Hz, 1H), 7.10 (s, 1H), 6.93 (s, 1H), 5.80 (s, 1H), 5.02 (s, 1H), 2.43 (s, 3H), 2.12 (s, 3H).

Example 113

(rac)-2-[1-(3-Methyl-5-{[4-(trifluoromethyl)pyrimidin-2-yl]amino}phenyl)-1H-imidazol-4-yl]propane-1,2-diol

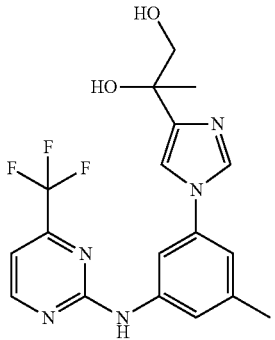 [SMILES: Cc1cc(Nc2nccc(C(F)(F)F)n2)cc(-n2cnc(C(C)(O)CO)c2)c1]

N-{3-Methyl-5-[4-(prop-1-en-2-yl)-1H-imidazol-1-yl]phenyl}-4-(trifluoromethyl)-pyrimidin-2-amine (51 mg, 0.14 mmol) and N-methylmorpholine-N-oxide (33 mg, 0.28 mmol) were dissolved in acetone:water (1.5 mL, 8:1). Osmium tetroxide (173 µL, 0.028 mmol, 4% in water) was added, and the suspension was stirred for 3 days at rt. N-methylmorpholine-N-oxide (33 mg, 0.28 mmol) and osmium tetroxide (173 µL, 0.028 mmol, 4% in water) were added to the mixture, and stirring was continued for 17 h at rt. Aqueous sodium thiosulfate (5%) was added, and the mixture was stirred 15 min at rt. The mixture was filtered through CELITE and cake washed with EtOAc. The filtrate was diluted with water and EtOAc, the layers were separated, and the aqueous portion extracted with EtOAc (2×). The combined organic extracts were dried over Na$_2$SO$_4$, filtered, and concentrated in vacuo. Purification via silica gel column chromatography (0%-40% MeOH:EtOAc) gave (rac)-2-[1-(3-methyl-5-{[4-(trifluoromethyl)pyrimidin-2-yl]amino}phenyl)-1H-imidazol-4-yl]propane-1,2-diol as a colorless oil. MS ESI calcd. for $C_{18}H_{19}F_3N_5O_2$ [M+H]+ 394. found 394. $^1$H NMR (500 MHz, DMSO-d$_6$) δ 10.34 (s, 1H), 8.84 (d, J=4.9 Hz, 1H), 8.00 (s, 1H), 7.90 (s, 1H), 7.43 (s, 1H), 7.35 (s, 1H), 7.30 (d, J=4.9 Hz, 1H), 7.10 (s, 1H), 4.66 (s, 1H), 3.56-3.38 (m, 2H), 3.15 (m, 1H), 2.33 (s, 3H), 1.37 (s, 3H).

Example 114

3-(1-(6-((4-(Trifluoromethyl)pyridin-2-yl)amino)pyridin-2-yl)-1H-imidazol-4-yl)propanoic acid

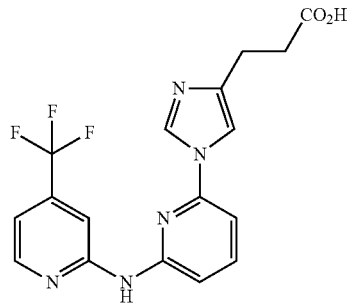 [SMILES: O=C(O)CCc1cn(-c2cccc(Nc3cc(C(F)(F)F)ccn3)n2)cn1]

To a sealed tube was added 6-bromo-N-(4-(trifluoromethyl)pyridin-2-yl)pyridin-2-amine (0.020 g, 0.063 mmol), 3-(1H-imidazol-4-yl)propanoic acid (0.009 g, 0.063 mmol), potassium phosphate tribasic (0.042 g, 0.20 mmol) and DMSO (0.60 mL). The reaction tube was sealed and heated to 130° C. for 12 hours. The reaction mixture was passed through a syringe filter, diluted with DMSO (0.40 mL) and purified by reverse phase preparative HPLC (0:100 to 95:5 acetonitrile:water: 0.1% v/v ammonium hydroxide modifier) to afford 3-(1-(6-((4-(trifluoromethyl)pyridin-2-yl)amino)pyridin-2-yl)-1H-imidazol-4-yl)propanoic acid. MS ESI calc. for $C_{17}H_{15}F_3N_5O_2$ [M+H]$^+$ 378. found 378. $^1$H NMR (600 MHz, DMSO-d$_6$) δ 10.36 (s, 1H), 8.49 (s, 1H), 8.32 (s, 1H), 8.24 (s, 1H), 7.82 (s, 1H), 7.56 (s, 1H), 7.44 (d, J=8.2, 1H), 7.22 (d, J=7.9, 2H), 2.70 (s, 2H).

Example 115

3-(1-(6-((4-cyclopropylpyridin-2-yl)amino)-4-methylpyridin-2-yl)-1H-imidazol-4-yl)propanoic acid

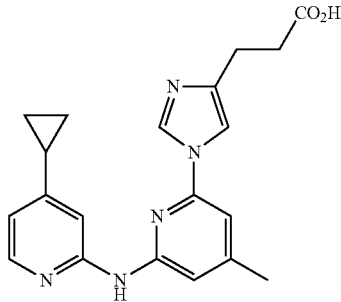 [SMILES: Cc1cc(Nc2cc(C3CC3)ccn2)nc(-n2cnc(CCC(=O)O)c2)c1]

To a sealed tube was added 6-bromo-N-(4-cyclopropylpyridin-2-yl)-4-methylpyridin-2-amine (0.020 g, 0.066 mmol), 3-(1H-imidazol-4-yl)propanoic acid (0.010 g, 0.066 mmol), potassium phosphate tribasic (0.042 g, 0.20 mmol) and DMSO (0.60 mL). The reaction tube was sealed and heated to 130° C. for 12 hours. The reaction mixture was passed through a syringe filter, the filtrate was diluted with DMSO (0.40 mL) and was purified by reverse phase preparative HPLC (0:100 to 95:5 acetonitrile:water: 0.1% v/v ammonium hydroxide modifier) to afford 3-(1-(6-((4-cyclopropylpyridin-2-yl)amino)-4-methylpyridin-2-yl)-1H-imidazol-4-yl)propanoic acid. MS ESI calc. for $C_{20}H_{22}N_5O_2$ [M+H]$^+$ 364. Found 364. $^1$H NMR (600 MHz, DMSO-d$_6$) δ 9.61 (s, 1H), 8.31 (d, J=1.2, 1H), 8.03 (d, J=5.2, 1H), 7.56 (s, 1H), 7.47 (s, 1H), 7.33 (s, 1H), 7.01 (s, 1H), 6.62 (d, J=5.3, 1H), 2.73 (t, J=7.5, 2H), 2.53 (t, J=7.5, 2H), 2.28 (s, 3H), 1.92-1.81 (m, 1H), 1.08-0.96 (m, 2H), 0.81-0.66 (m, 2H).

Example 116

4-Hydroxy-4-[1-(4-methyl-6-{[4-(trifluoromethyl)pyridin-2-yl]amino}pyridin-2-yl)-1H-imidazol-4-yl]piperidine-1-carboxamide

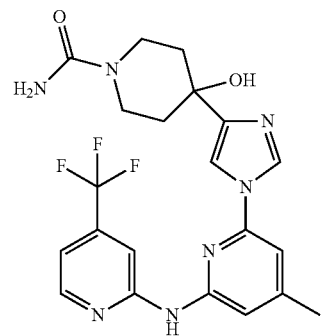 [SMILES: Cc1cc(Nc2cc(C(F)(F)F)ccn2)nc(-n2cnc(C3(O)CCN(C(N)=O)CC3)c2)c1]

Step 1:

A suspension of benzyl 4-hydroxy-4-(1H-imidazol-4-yl)piperidine-1-carboxylate (130 mg, 0.431 mmol), 6-bromo-4-methyl-N-[4-(trifluoromethyl)pyridin-2-yl]pyridin-2-amine (143 mg, 0.431 mmol), L-proline (14.90 mg, 0.129 mmol), copper (I) iodide (12.32 mg, 0.065 mmol), and potassium carbonate (119 mg, 0.863 mmol) in dimethylsulfoxide (1.25 ml) was stirred under an argon atmosphere at 120° C. for five hours. Upon cooling to room temperature, the reaction mixture was diluted with ethyl acetate (20 mL), water (5 mL), and saturated aqueous sodium bicarbonate (15 mL). The aqueous layer was extracted with ethyl acetate (2×20 mL). The combined organic layers were washed with water (3×15 mL) and brine (20 mL), dried over sodium sulfate, filtered, and concentrated. The residue was purified by chromatography on silica gel (1.5-10% methanol/dichloromethane) to give benzyl 4-hydroxy-4-[1-(4-methyl-6-{[4-(trifluoromethyl)pyridin-2-yl]amino}pyridin-2-yl)-1H-imidazol-4-yl]piperidine-1-carboxylate. MS ESI calc. for $C_{28}H_{28}F_3N_6O_3$ [M+H]+ 553. found 553.

Step 2:

To a solution of benzyl 4-hydroxy-4-[1-(4-methyl-6-{[4-(trifluoromethyl)pyridin-2-yl]amino}pyridin-2-yl)-1H-imidazol-4-yl]piperidine-1-carboxylate (140 mg, 0.253 mmol) in methanol (7 mL) was added palladium on carbon (5 wt %, 53.9 mg, 0.025 mmol) and the resulting suspension was placed under a hydrogen atmosphere using three vacuum/balloon hydrogen flush cycles. After three hours, the reaction mixture was filtered through CELITE and concentrated to afford 4-[1-(4-methyl-6-{[4-(trifluoromethyl)pyridin-2-yl]amino}pyridin-2-yl)-1H-imidazol-4-yl]piperidin-4-ol. MS ESI calc. for $C_{20}H_{21}F_3N_6O$ [M+H]+ 419. found 419.

Step 3:

To a suspension of 4-[1-(4-methyl-6-{[4-(trifluoromethyl)pyridin-2-yl]amino}pyridin-2-yl)-1H-imidazol-4-yl]piperidin-4-ol (39.1 mg, 0.093 mmol) and potassium cyanate (11.4 mg, 0.140 mmol) in tetrahydrofuran (0.6 mL) and water (1.2 mL) was added hydrochloric acid (2 M, 0.065 mL, 0.13 mmol). After 4 hours at 50° C., additional potassium cyanate (4.4 mg, 0.054 mmol) and hydrochloric acid (2 M, 0.024 mL, 0.048 mmol) was added. After an additional 2 hours, the reaction mixture was concentrated and purified by reverse phase liquid chromatography (acetonitrile/water containing 0.1% TFA). The fractions containing product were partitioned between 10% v/v isopropanol/chloroform (25 mL) and saturated aqueous sodium bicarbonate (25 mL). The aqueous layer was extracted with 10% v/v isopropanol/chloroform (2×25 mL) and then the combined organic extracts were washed with brine, dried over sodium sulfate, filtered, and concentrated under reduced pressure to give 4-hydroxy-4-[1-(4-methyl-6-{[4-(trifluoromethyl)pyridin-2-yl]amino}pyridin-2-yl)-1H-imidazol-4-yl]piperidine-1-carboxamide. MS ESI calc. for $C_{21}H_{23}F_3N_7O_2$ [M+H]+ 462. found 462.

$^1$H NMR (500 MHz, DMSO-d$_6$) δ 10.30 (s, 1H), 8.51 (s, 1H), 8.35 (s, 1H), 8.27 (s, 1H), 7.70 (s, 1H), 7.28 (s, 1H), 7.22 (s, 1H), 5.88 (s, 2H), 5.74 (s, 1H), 4.87 (s, 1H), 3.60-3.52 (m, 2H), 3.22-3.14 (m, 2H), 2.34 (s, 3H), 1.93-1.85 (m, 2H), 1.67-1.59 (m, 2H).

Example 117

4-Hydroxy-4-[1-(3-methyl-5-{[4-(trifluoromethyl)pyrimidin-2-yl]amino}phenyl)-1H-imidazol-4-yl]piperidine-1-carboxamide

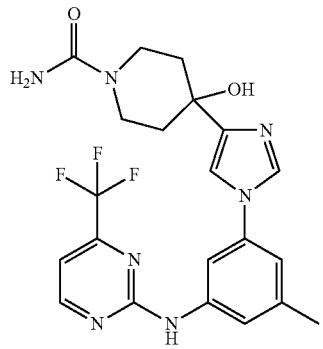 [SMILES: Cc1cc(Nc2nccc(C(F)(F)F)n2)cc(-n2cnc(C3(O)CCN(C(N)=O)CC3)c2)c1]

Step 1:

A suspension of 9H-fluoren-9-ylmethyl 4-hydroxy-4-(1H-imidazol-4-yl)piperidine-1-carboxylate (240 mg, 0.616 mmol), N-(3-iodo-5-methylphenyl)-4-(trifluoromethyl)pyrimidin-2-amine (234 mg, 0.616 mmol), L-proline (42.6 mg, 0.370 mmol), copper (I) iodide (35.2 mg, 0.185 mmol), and potassium carbonate (170 mg, 1.233 mmol) in dimethylsulfoxide (2.5 ml) was stirred under an argon atmosphere at 120° C. for four hours. Upon cooling to room temperature, the reaction mixture was diluted with ethyl acetate (20 mL), water (5 mL), and saturated aqueous sodium bicarbonate (15 mL). The aqueous layer was extracted with ethyl acetate (2×20 mL). The combined organic layers were washed with water (3×15 mL) and brine (20 mL), dried over sodium sulfate, filtered, and concentrated. The residue was purified by reverse phase liquid chromatography (acetonitrile/water containing 0.1% TFA). The fractions containing product were lyophilized and then partitioned between 10% v/v isopropanol/chloroform (25 mL) and saturated aqueous sodium bicarbonate (25 mL). The aqueous layer was extracted again with 10% v/v isopropanol/chloroform (2×20 mL) and the combined organic extracts were washed with brine, dried over sodium sulfate, filtered, and concentrated under reduced pressure to provide 4-[1-(3-methyl-5-{[4-(trifluoromethyl)pyrimidin-2-yl]amino}phenyl)-1H-imidazol-4-yl]piperidin-4-ol. MS ESI calc. for $C_{20}H_{22}F_3N_6O$ [M+H]+ 419. found 419.

Step 2:

To a suspension of 4-[1-(3-methyl-5-{[4-(trifluoromethyl)pyrimidin-2-yl]amino}phenyl)-1H-imidazol-4-yl]piperidin-4-ol (51.9 mg, 0.124 mmol) and potassium cyanate (15.09 mg, 0.186 mmol) in tetrahydrofuran (0.7 mL) and water (1.5 mL) was added hydrochloric acid (2 M, 0.087 mL, 0.174 mmol). After 5 hours at 50° C., the reaction mixture was concentrated and purified by reverse phase liquid chromatography (acetonitrile/water containing 0.1% TFA). The fractions containing product were partitioned between 10% v/v isopropanol/chloroform (25 mL) and saturated aqueous sodium bicarbonate (25 mL) followed by addition of solid sodium chloride until the aqueous layer was saturated. The layers were separated and the aqueous layer was extracted again with 10% v/v isopropanol/chloroform (20 mL). The combined organic extracts were washed with brine, dried over sodium sulfate, filtered, and concentrated under reduced pressure to give 4-hydroxy-4-[1-(3-methyl-5-{[4-(trifluoromethyl)pyrimidin-2-yl]amino}phenyl)-1H-imidazol-4-yl]piperidine-1-carboxamide. MS ESI calc. for $C_{21}H_{23}F_3N_7O_2$ [M+H]+ 462. found 462. $^1$H NMR (500 MHz, DMSO-$d_6$) δ 10.34 (s, 1H), 8.84 (d, J=4.9 Hz, 1H), 8.02 (d, J=1.4 Hz, 1H), 7.90 (s, 1H), 7.43 (s, 1H), 7.40 (d, J=1.4 Hz, 1H), 7.30 (d, J=4.9 Hz, 1H), 7.12 (s, 1H), 5.87 (s, 2H), 4.87 (s, 1H), 3.62-3.54 (m, 2H), 3.20-3.12 (m, 2H), 2.33 (s, 3H), 1.93-1.85 (m, 2H), 1.60 (d, J=13.0, 2H).

Example 118

General Procedure for a Compound of Formula (A)

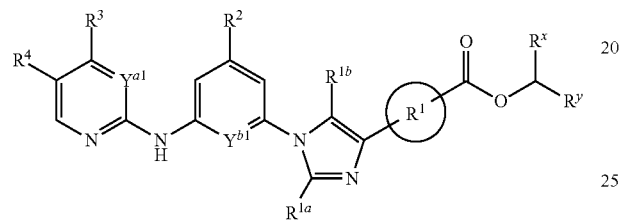

This general procedure describes the procedure for conversion of (A1) to (A) as shown in Scheme 16. To a mixture of compound of formula (A1) (1 mmol), 1° or 2° alcohol (5 mmol), and triphenylphosphine (resin-bound, 1.6 mmol/g loading, 2 mmol) in tetrahydrofuran is added di-tert-butyl azodicarboxylate (2 mmol) at 20° C. The reaction mixture is stirred at 20° C. for 16 hours. The reaction mixture is diluted with TFA (1 mL) and water (1 drop). The mixture is stirred for 30 minutes. The mixture is then filtered through CELITE, washing with dichloromethane (3×). The filtrate is concentrated under reduced pressure to afford the crude residue TFA salt. The residue is diluted carefully with saturated aqueous sodium bicarbonate solution and ethyl acetate. The organic layer is separated, washed with brine, dried over magnesium sulfate, filtered, and concentrated under reduced pressure to afford the crude residue free base. The residue is purified by silica gel chromatography (ethyl acetate/hexanes, linear gradient) to afford the product residue. The residue is lyophilized from acetonitrile and water to afford a compound of formula (A).

The following compounds could be prepared according to procedures which are analogous to those described in Example 118.

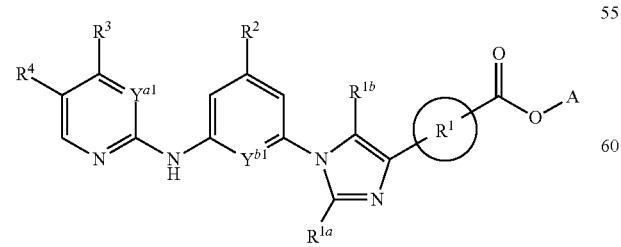

$Y^{a1}$=N and $Y^{b1}$=CH or $Y^{a1}$=CH and $Y^{b1}$=N

| Ex. | A |
|---|---|
| 118-1 | 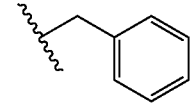 |
| 118-2 |  |
| 118-3 | 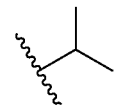 [SMILES: *C(C)C] |
| 118-4 | 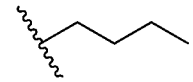 [SMILES: *CCCC] |
| 118-5 | 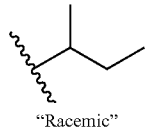<br>"Racemic" |
| 118-6 |  |
| 118-7 | 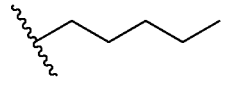 [SMILES: *CCCCC] |
| 118-8 |  |
| 118-9 | 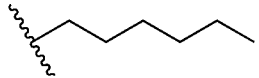 [SMILES: *CCCCCC] |
| 118-10 | 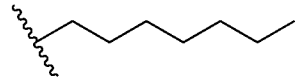 [SMILES: *CCCCCCC] |
| 118-11 | 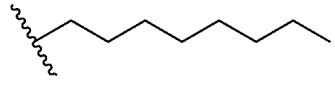 [SMILES: *CCCCCCCC] |
| 118-12 | 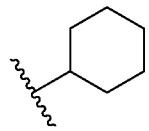 [SMILES: *C1CCCCC1] |
| 118-13 | 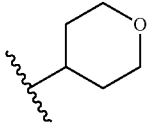 [SMILES: *C1CCOCC1] |
| 118-14 | 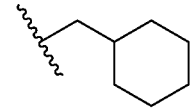 |

| Ex. | A |
|---|---|
| 118-15 | ~~~CH2CH2-O-CH3 |
| 118-16 | ~~~CH2CH2-O-CH2CH2-O-CH2CH3 |
| 118-17 | ~~~CH2-C(=O)-O-CH3 |
| 118-18 | ~~~CH2-C(=O)-N(CH3)2 |
| 118-19 | ~~~CH2CH2CH2-morpholine |
| 118-20 | ~~~CH2CH2-N(CH3)2 |
| 118-21 | ~~~CH2-(4-methyl-1,3-dioxol-2-one-5-yl) |

Example 119

General Procedure for the Compound of Formula (C)

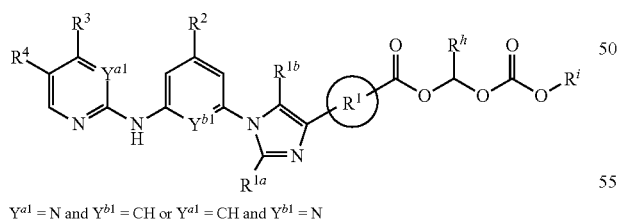

$Y^{a1}$ = N and $Y^{b1}$ = CH or $Y^{a1}$ = CH and $Y^{b1}$ = N

This general procedure describes the procedure for conversion of (A1) to (C) as shown in Scheme 16. A mixture of compound of formula (A1) (1.0 mmol), potassium carbonate (2.0 mmol), and sodium iodide (0.50 mmol) in DMF is stirred at 20° C. After 30 minutes, alkyl halide of formula (C1) (0.95 mmol) is added and the reaction mixture is stirred at 20° C. After 16 hours, the reaction mixture is diluted with ethyl acetate and washed with water (4×). The organic layer is separated, washed with brine, dried over magnesium sulfate, filtered, and concentrated under reduced pressure to afford the crude residue. The residue is purified by silica gel chromatography (ethyl acetate/hexanes, linear gradient) to afford the product residue. The residue is lyophilized from acetonitrile and water to afford a compound of formula (C).

The following compounds could be prepared according to procedures, which are analogous to those described in Example 119.

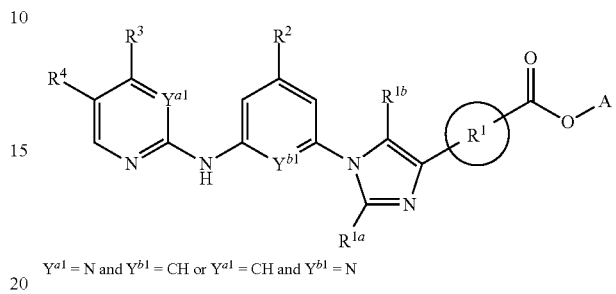

$Y^{a1}$ = N and $Y^{b1}$ = CH or $Y^{a1}$ = CH and $Y^{b1}$ = N

| Ex. No. | A |
|---|---|
| 119-1 | ~~~CH2-O-C(=O)-O-CH(CH3)2 |
| 119-2 | ~~~CH(CH3)-O-C(=O)-O-CH2CH3 "Racemic" |
| 119-3 | ~~~CH(CH3)-O-C(=O)-O-CH(CH3)2 "Racemic" |
| 119-4 | ~~~CH(CH3)-O-C(=O)-O-cyclohexyl "Racemic" |
| 119-5 | ~~~CH(CH3)-O-C(=O)-O-CH2CH3 "Isomer 1" |
| 119-6 | ~~~CH(CH3)-O-C(=O)-O-CH2CH3 "Isomer 2" |
| 119-7 | ~~~CH(CH3)-O-C(=O)-O-CH(CH3)2 "Isomer 1" |

-continued

| Ex. No. | A |
|---|---|
| 119-8 | "Isomer 2" |
| 119-9 | "Isomer 1" |
| 119-10 | "Isomer 2" |

Example 120

General Procedure for the Compound of Formula (B)

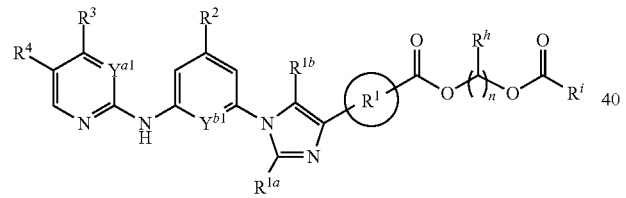

(n) = 1, 2

$Y^{a1}$ = N and $Y^{b1}$ = CH or $Y^{a1}$ = CH and $Y^{b1}$ = N

This general procedure describes the procedure for conversion of (A1) to (B) as shown in Scheme 16. To a solution of compound of formula (A1) (1.0 mmol) in DMF is added potassium carbonate (2.0 mmol) and sodium iodide (0.20 mmol). After 75 minutes, alkyl halide of formula (B1) (1.0 mmol) is added and the reaction mixture is stirred for an additional 4 hours. The reaction mixture is then partitioned between ethyl acetate and aqueous saturated sodium bicarbonate. The layers are separated, and then the organic layer is washed with water (3×) and brine, dried over sodium sulfate, filtered, and concentrated under reduced pressure. The resulting residue is purified by silica gel chromatography (ethyl acetate/hexanes, linear gradient) to afford the product residue. The residue is lyophilized from acetonitrile and water to afford a compound of formula (B).

The following compounds could be prepared according to procedures which are analogous to those described in Example 120.

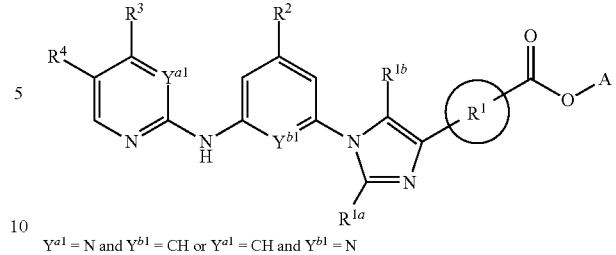

$Y^{a1}$ = N and $Y^{b1}$ = CH or $Y^{a1}$ = CH and $Y^{b1}$ = N

| Ex. No. | A |
|---|---|
| 120-1 | |
| 120-2 | "Isomer 1" |
| 120-3 | "Isomer 2" |
| 120-4 | "Isomer 1" |
| 120-5 | "Isomer 2" |
| 120-6 | |

What is claimed is:
1. A compound of Formula I:

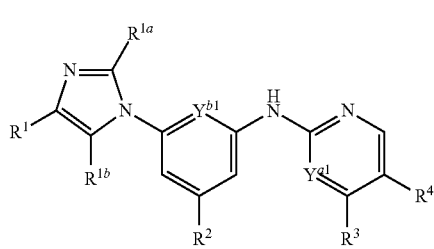

or a pharmaceutically acceptable salt thereof, wherein:
$Y^{a1}$ is CH or N;
$Y^{b1}$ is CH or N, such that $Y^{b1}$ and $Y^{a1}$ cannot both simultaneously be C or N;

$R^{1a}$ and $R^{1b}$ are independently H or $C_1$-$C_3$-alkyl;

$R^1$ is:
  ($CR^aR^b$)$_n$-cyclohexyl, wherein said cyclohexyl may optionally be substituted with one to four substituents selected from hydroxyl, $C_1$-$C_3$-alkyl, $C_1$-$C_3$-alkoxyl, ($CR^aR^b$)$_n$$CO_2R^c$, ($CR^aR^b$)$_n$$CONR^dR^e$, and a spiro-linked —$OCH_2CH_2O$—;

$R^a$ and $R^b$ are independently: H, OH, or $C_1$-$C_3$-alkyl optionally substituted with 1-3 hydroxyl;

$R^c$ is: H or $C_{1-4}$alkyl;

$R^d$ and $R^e$ are independently: H, $C_1$-$C_3$-alkoxyl or $C_1$-$C_6$-alkyl, optionally substituted with 1-4 substituents selected from: CN, OH, oxo; $NH_2$, halogen, $CO_2R^c$, $CONH_2$, $C_1$-$C_3$-alkoxyl, $CO_2R^c$; aryl, carbocyclyl, and heterocyclyl, as defined below;

or alternatively, $R^d$ and $R^e$ taken together with the nitrogen to which they are attached form a heterocyclic 5- to 6-membered monocyclic ring containing 0-2 additional heteroatoms selected from O, N, or S, the ring may be saturated, unsaturated or aromatic; the heterocyclic ring is optionally substituted with 1-2 substituents selected from CN; OH; oxo; $NH_2$; halogen; $COCH_3$, $CO_2R^c$; $CONH_2$; $C_1$-$C_3$-alkyl; $C_1$-$C_3$-haloalkyl; $C_1$-$C_3$-alkoxyl optionally substituted with OH; aryl optionally substituted with $C_1$-$C_3$-alkoxyl; $CH_2$aryl; Oaryl optionally substituted with halogen; and heterocyclyl, wherein aryl and heterocyclyl are as defined below;

wherein said heterocyclyl, carbocyclyl and aryl of $R^d$ and $R^e$ are as follows:
  heterocyclyl is a 4-, 5-, 6-, or 7-membered monocyclic ring or 8-, 9-, 10-membered bicyclic ring, or 13- or 14-membered tricyclic ring; the monocyclic, bicyclic or tricyclic ring can be saturated, unsaturated or aromatic, containing 1, 2, 3 or 4 heteroatoms selected from O, N, or S, the heterocyclyl may optionally be substituted with one to four substituents selected from oxo, halo, hydroxyl, $C_1$-$C_3$-alkyl, $C_2$-$C_6$-alkenyl, $C_1$-$C_3$-alkoxyl, ($CR^aR^b$)$_n$$CO_2R^c$, ($CR^aR^b$)$_n$$CONR^dR^e$; ($CHR^a$)$_n$$NHCONR^dR^e$; and ($CHR^a$)$_p$—C(O)-heterocyclyl;

carbocyclyl is a 4-, 5-, 6-, 7- or 8-membered monocyclic ring or 8-, 9-, 10-membered bicyclic ring, or 13- or 14-membered tricyclic ring, in which all ring atoms are carbon, at least one ring is saturated or partially unsaturated and that ring being isolated or fused to one or two such rings or to a benzene ring; the carbocyclyl may optionally be substituted with one to four substituents selected from hydroxyl, $C_1$-$C_3$-alkyl, $C_1$-$C_3$-alkoxyl, ($CR^aR^b$)$_n$$CO_2R^c$, ($CR^aR^b$)$_n$$CONR^dR^e$, and a spiro-linked —$OCH_2CH_2O$—;

aryl is a 6-membered monocyclic or 10-membered bicyclic aromatic carbon ring, the aryl may optionally be substituted with one to four substituents selected from hydroxyl, $C_1$-$C_3$-alkyl, $C_1$-$C_3$-alkoxyl, ($CR^aR^b$)$_n$$CO_2R^c$, and ($CR^aR^b$)$_n$$CONR^dR^e$;

n is 0, 1, 2, 3 or 4;
p is 0 or 1;
$R^2$ is H or $CH_3$;
$R^3$ is H, $CF_3$, $CH_3$, or $CF_2$H; and
$R^4$ is H, Cl or F.

2. The compound of claim 1, wherein the compound of Formula I has the Formula Ia

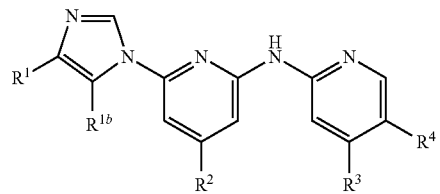

or a pharmaceutically acceptable salt thereof.

3. The compound of claim 1, wherein the compound of Formula I has the Formula Ib

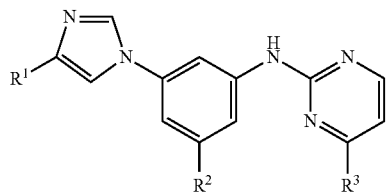

or a pharmaceutically acceptable salt thereof.

4. The compound of claim 1 or a pharmaceutically acceptable salt thereof, wherein $R^3$ is $CF_3$ and $R^2$ is methyl.

5. The compound of claim 1, or a pharmaceutically acceptable salt thereof selected from:
  Cis-4-hydroxy-N-methyl-4-[1-(3-methyl-5-{[4-(trifluoromethyl)pyrimidin-2-yl]amino}phenyl)-1H-imidazol-4-yl]cyclohexanecarboxamide;
  Trans-4-[1-(3-methyl-5-{[4-(trifluoromethyl)pyrimidin-2-yl]amino}phenyl)-1H-imidazol-4-yl]cyclohexanecarboxylic acid;
  Cis-4-[1-(3-methyl-5-{[4-(trifluoromethyl)pyrimidin-2-yl]amino}phenyl)-1H-imidazol-4-yl]cyclohexanecarboxylic acid;
  Rac-(1R,3S,4S)-3,4-dihydroxy-1-methyl-4-[1-(3-methyl-5-{[4-(trifluoromethyl)pyrimidin-2-yl]amino}phenyl)-1H-imidazol-4-yl]cyclohexanecarboxylic acid;
  Rac-(1R,3R,4R)-3,4-dihydroxy-1-methyl-4-[1-(3-methyl-5-{[4-(trifluoromethyl)pyrimidin-2-yl]amino}phenyl)-1H-imidazol-4-yl]cyclohexanecarboxylic acid;
  2-{Cis-4-hydroxy-4-[1-(3-methyl-5-{[4-(trifluoromethyl)pyrimidin-2-yl]amino}phenyl)-1H-imidazol-4-yl]cyclohexyl}acetamide;
  Trans-4-{1-hydroxy-1-[1-(3-methyl-5-{[4-(trifluoromethyl)pyrimidin-2-yl]amino}phenyl)-1H-imidazol-4-yl]ethyl}cyclohexanecarboxamide;
  Trans-4-[1-hydroxy-1-(1-{3-methyl-5-[(4-methyl-pyrimidin-2-yl)amino]-phenyl}-1H-imidazol-4-yl)ethyl]cyclohexane-carboxylic acid;
  Trans-4-{1-hydroxy-1-[1-(3-methyl-5-{[4-(trifluoromethyl)pyrimidin-2-yl]amino}phenyl)-1H-imidazol-4-yl]ethyl}-cyclohexanecarboxylic acid;
  Butyl Trans-4-[1-hydroxy-1-(1-{3-methyl-5-[(4-methyl-pyrimidin-2-yl)amino]phenyl}-1H-imidazol-4-yl)ethyl]-cyclohexanecarboxylate;
  Butyl Trans-4-{1-hydroxy-1-[1-(3-methyl-5-{[4-(trifluoromethyl)pyrimidin-2-yl]amino}phenyl)-1H-imidazol-4-yl]ethyl}cyclohexanecarboxylate;
  {Trans-4-hydroxy-4-[1-(4-methyl-6-{[4-(trifluoromethyl)pyridin-2-yl]amino}pyridin-2-yl)-1H-imidazol-4-yl]cyclohexyl}acetic acid;

{Cis-4-hydroxy-4-[1-(4-methyl-6-{[4-(trifluoromethyl)pyridin-2-yl]amino}pyridin-2-yl)-1H-imidazol-4-yl]cyclohexyl}acetic acid;
{Trans-4-hydroxy-4-[1-(3-methyl-5-{[4-(trifluoromethyl)pyrimidin-2-yl]amino}phenyl)-1H-imidazol-4-yl]cyclohexyl}acetic acid;
{Cis-4-hydroxy-4-[1-(3-methyl-5-{[4-(trifluoromethyl)pyrimidin-2-yl]amino}phenyl)-1H-imidazol-4-yl]cyclohexyl}acetic acid;
Methyl {Trans-4-hydroxy-4-[1-(3-methyl-5-{[4-(trifluoromethyl)pyrimidin-2-yl]amino}phenyl)-1H-imidazol-4-yl]cyclohexyl}acetate;
Methyl {Cis-4-hydroxy-4-[1-(3-methyl-5-{[4-(trifluoromethyl)pyrimidin-2-yl]amino}phenyl)-1H-imidazol-4-yl]cyclohexyl}acetate;
Trans-4-hydroxy-1-methyl-4-[1-(3-methyl-5-{[4-(trifluoromethyl)pyrimidin-2-yl]amino}phenyl)-1H-imidazol-4-yl]cyclohexanecarboxylic acid;
Ethyl Trans-4-hydroxy-1-methyl-4-[1-(3-methyl-5-{[4-(trifluoromethyl)pyrimidin-2-yl]amino}phenyl)-1H-imidazol-4-yl]cyclohexanecarboxylate;
Ethyl 2-{Cis-4-hydroxy-4-[1-(4-methyl-6-{[4-(trifluoromethyl)pyridin-2-yl]amino}pyridin-2-yl)-1H-imidazol-4-yl]cyclohexyl}-2-methylpropanoate;
Ethyl 2-{Trans-4-hydroxy-4-[1-(4-methyl-6-{[4-(trifluoromethyl)pyridin-2-yl]amino}pyridin-2-yl)-1H-imidazol-4-yl]cyclohexyl}-2-methylpropanoate;
4-Hydroxy-2,2-dimethyl-4-[1-(3-methyl-5-{[4-(trifluoromethyl)pyrimidin-2-yl]amino}phenyl)-1H-imidazol-4-yl]cyclohexanecarboxylic acid;
Trans-4-hydroxy-4-[1-(4-methyl-6-{[4-(trifluoromethyl)pyridin-2-yl]amino}pyridin-2-yl)-1H-imidazol-4-yl]cyclohexanecarboxylic acid;
Cis-4-hydroxy-4-[1-(4-methyl-6-{[4-(trifluoromethyl)pyridin-2-yl]amino}pyridin-2-yl)-1H-imidazol-4-yl]cyclohexanecarboxylic acid;
Ethyl Trans-4-hydroxy-4-[1-(4-methyl-6-{[4-(trifluoromethyl)pyridin-2-yl]amino}pyridin-2-yl)-1H-imidazol-4-yl]cyclohexanecarboxylate;
Ethyl Cis-4-hydroxy-4-[1-(4-methyl-6-{[4-(trifluoromethyl)pyridin-2-yl]amino}pyridin-2-yl)-1H-imidazol-4-yl]cyclohexanecarboxylate;
Cis-1-[1-(3-methyl-5-{[4-(trifluoromethyl)pyrimidin-2-yl]amino}phenyl)-1H-imidazol-4-yl]-4-(morpholin-4-ylcarbonyl)cyclohexanol;
Cis-1-[1-(3-methyl-5-{[4-(trifluoromethyl)pyrimidin-2-yl]amino}phenyl)-1H-imidazol-4-yl]-4-(pyrrolidin-1-ylcarbonyl)cyclohexanol;
Cis-4-hydroxy-N,N-dimethyl-4-[1-(3-methyl-5-{[4-(trifluoromethyl)pyrimidin-2-yl]amino}phenyl)-1H-imidazol-4-yl]cyclohexanecarboxamide;
Trans-4-hydroxy-4-[1-(3-methyl-5-{[4-(trifluoromethyl)pyrimidin-2-yl]amino}phenyl)-1H-imidazol-4-yl]cyclohexanecarboxamide;
Cis-4-hydroxy-4-[1-(3-methyl-5-{[4-(trifluoromethyl)pyrimidin-2-yl]amino}phenyl)-1H-imidazol-4-yl]cyclohexanecarboxamide;
Trans-4-hydroxy-4-[1-(3-methyl-5-{[4-(trifluoromethyl)pyrimidin-2-yl]amino}phenyl)-1H-imidazol-4-yl]cyclohexanecarboxylic acid;
Ethyl Trans-4-hydroxy-4-[1-(3-methyl-5-{[4-(trifluoromethyl)pyrimidin-2-yl]amino}phenyl)-1H-imidazol-4-yl]cyclohexanecarboxylate;
Cis-1-[1-(3-methyl-5-{[4-(trifluoromethyl)pyrimidin-2-yl]amino}phenyl)-1H-imidazol-4-yl]cyclohexane-1,4-diol;
Cis-1-(1-{3-methyl-5-[(4-methylpyrimidin-2-yl)amino]phenyl}-1H-imidazol-4-yl)cyclohexane-1,4-diol;
Cis-1-(1-{6-[(5-fluoro-4-methylpyridin-2-yl)amino]-4-methylpyridin-2-yl}-1H-imidazol-4-yl)cyclohexane-1,4-diol;
Cis-1-(1-{6-[(5-chloro-4-methylpyridin-2-yl)amino]-4-methylpyridin-2-yl}-1H-imidazol-4-yl)cyclohexane-1,4-diol;
Cis-1-(1-{4-methyl-6-[(4-methylpyridin-2-yl)amino]pyridin-2-yl}-1H-imidazol-4-yl)cyclohexane-1,4-diol;
Cis-4-(1-{6-[(5-fluoro-4-methylpyridin-2-yl)amino]-4-methylpyridin-2-yl}-1H-imidazol-4-yl)-4-hydroxycyclohexyl benzoate;
Cis-4-(1-{6-[(5-chloro-4-methylpyridin-2-yl)amino]-4-methylpyridin-2-yl}-1H-imidazol-4-yl)-4-hydroxycyclohexyl benzoate;
Cis-4-hydroxy-4-(1-{4-methyl-6-[(4-methylpyridin-2-yl)amino]pyridin-2-yl}-1H-imidazol-4-yl)cyclohexyl benzoate;
4-Hydroxy-4-[1-(3-methyl-5-{[4-(trifluoromethyl)pyrimidin-2-yl]amino}phenyl)-1H-imidazol-4-yl]cyclohexanone;
(1S,3S,4S)-3-Methyl-1-[1-(3-methyl-5-{[4-(trifluoromethyl)pyrimidin-2-yl]amino}phenyl)-1H-imidazol-4-yl]cyclohexane-1,4-diol;
(1R,3S,4S)-3-Methyl-1-[1-(3-methyl-5-{[4-(trifluoromethyl)pyrimidin-2-yl]amino}phenyl)-1H-imidazol-4-yl]cyclohexane-1,4-diol;
(1S,3S,4R)-3-Methyl-1-[1-(3-methyl-5-{[4-(trifluoromethyl)pyrimidin-2-yl]amino}phenyl)-1H-imidazol-4-yl]cyclohexane-1,4-diol;
Cis-1-(1-{3-[(5-fluoro-4-methylpyrimidin-2-yl)amino]-5-methylphenyl}-1H-imidazol-4-yl)cyclohexane-1,4-diol;
Cis-4-(1-{3-[(5-fluoro-4-methylpyrimidin-2-yl)amino]-5-methylphenyl}-1H-imidazol-4-yl)-4-hydroxycyclohexyl benzoate;
Trans-1-[1-(4-methyl-6-{[4-(trifluoromethyl)pyridin-2-yl]amino}pyridin-2-yl)-1H-imidazol-4-yl]cyclohexane-1,4-diol;
Cis-1-[1-(4-methyl-6-{[4-(trifluoromethyl)pyridin-2-yl]amino}pyridin-2-yl)-1H-imidazol-4-yl]cyclohexane-1,4-diol;
Trans-4-hydroxy-4-[1-(4-methyl-6-{[4-(trifluoromethyl)pyridin-2-yl]amino}pyridin-2-yl)-1H-imidazol-4-yl]cyclohexyl benzoate;
Cis-4-hydroxy-4-[1-(4-methyl-6-{[4-(trifluoromethyl)pyridin-2-yl]amino}pyridin-2-yl)-1H-imidazol-4-yl]cyclohexyl benzoate;
Trans-1-[1-(3-methyl-5-{[4-(trifluoromethyl)pyrimidin-2-yl]amino}phenyl)-1H-imidazol-4-yl]cyclohexane-1,4-diol;
Trans-4-hydroxy-4-[1-(3-methyl-5-{[4-(trifluoromethyl)pyrimidin-2-yl]amino}phenyl)-1H-imidazol-4-yl]cyclohexyl benzoate;
Ethyl cis-4-hydroxy-4-[1-(3-methyl-5-{[4-(trifluoromethyl)pyrimidin-2-yl]amino}phenyl)-1H-imidazol-4-yl]cyclohexanecarboxylate; and
Cis-4-hydroxy-4-[1-(3-methyl-5-{[4-(trifluoromethyl)pyrimidin-2-yl]amino}phenyl)-1H-imidazol-4-yl]cyclohexanecarboxylic acid.

6. The compound of claim 1, or a pharmaceutically acceptable salt thereof selected from:
Cis-4-hydroxy-N-methyl-4-[1-(3-methyl-5-{[4-(trifluoromethyl)pyrimidin-2-yl]amino}phenyl)-1H-imidazol-4-yl]cyclohexanecarboxamide;

Trans-4-[1-(3-methyl-5-{[4-(trifluoromethyl)pyrimidin-2-yl]amino}phenyl)-1H-imidazol-4-yl]cyclohexanecarboxylic acid;

Cis-4-[1-(3-methyl-5-{[4-(trifluoromethyl)pyrimidin-2-yl]amino}phenyl)-1H-imidazol-4-yl]cyclohexanecarboxylic acid;

Trans-4-[1-hydroxy-1-(1-{3-methyl-5-[(4-methyl-pyrimidin-2-yl)amino]-phenyl}-1H-imidazol-4-yl)ethyl]cyclohexane-carboxylic acid;

Trans-4-{1-hydroxy-1-[1-(3-methyl-5-{[4-(trifluoromethyl)pyrimidin-2-yl]amino}phenyl)-1H-imidazol-4-yl]ethyl}-cyclohexanecarboxylic acid;

{Cis-4-hydroxy-4-[1-(4-methyl-6-{[4-(trifluoromethyl)pyridin-2-yl]amino}pyridin-2-yl)-1H-imidazol-4-yl]cyclohexyl}acetic acid;

{Cis-4-hydroxy-4-[1-(3-methyl-5-{[4-(trifluoromethyl)pyrimidin-2-yl]amino}phenyl)-1H-imidazol-4-yl]cyclohexyl}acetic acid;

Cis-4-hydroxy-4-[1-(4-methyl-6-{[4-(trifluoromethyl)pyridin-2-yl]amino}pyridin-2-yl)-1H-imidazol-4-yl]cyclohexanecarboxylic acid;

Cis-1-[1-(3-methyl-5-{[4-(trifluoromethyl)pyrimidin-2-yl]amino}phenyl)-1H-imidazol-4-yl]cyclohexane-1,4-diol;

Cis-1-[1-(4-methyl-6-{[4-(trifluoromethyl)pyridin-2-yl]amino}pyridin-2-yl)-1H-imidazol-4-yl]cyclohexane-1,4-diol; and Cis-4-hydroxy-4-[1-(3-methyl-5-{[4-(trifluoromethyl)pyrimidin-2-yl]amino}phenyl)-1H-imidazol-4-yl]cyclohexanecarboxylic acid.

7. A pharmaceutical composition comprising a therapeutically effective amount of a compound of claim 1 or a pharmaceutically acceptable salt thereof, and a pharmaceutically acceptable carrier.

* * * * *